(12) United States Patent
Charmot et al.

(10) Patent No.: US 8,445,014 B2
(45) Date of Patent: *May 21, 2013

(54) ION BINDING COMPOSITIONS

(75) Inventors: Dominique Charmot, Campbell, CA (US); Han-Ting Chang, Livermore, CA (US); Eric Connor, Los Gatos, CA (US); Mingjun Liu, Campbell, CA (US); Gerrit Klaerner, San Jose, CA (US)

(73) Assignee: Relypsa, Inc., Redwood City, CA (US)

( * ) Notice: Subject to any disclaimer, the term of this patent is extended or adjusted under 35 U.S.C. 154(b) by 803 days.

This patent is subject to a terminal disclaimer.

(21) Appl. No.: 12/238,844

(22) Filed: Sep. 26, 2008

(65) Prior Publication Data

US 2009/0148533 A1 Jun. 11, 2009

Related U.S. Application Data

(63) Continuation of application No. 11/095,918, filed on Mar. 30, 2005, now Pat. No. 7,429,394, which is a continuation-in-part of application No. 10/965,274, filed on Oct. 13, 2004, now Pat. No. 7,488,495, which is a continuation-in-part of application No. 10/814,527, filed on Mar. 30, 2004, now Pat. No. 7,854,924, and a continuation-in-part of application No. 10/814,749, filed on Mar. 30, 2004, now Pat. No. 8,192,758, and a continuation-in-part of application No. 10/813,872, filed on Mar. 30, 2004, now Pat. No. 8,282,960.

(51) Int. Cl.
*A61K 9/14* (2006.01)

(52) U.S. Cl.
USPC ............................ 424/483; 424/489; 424/490

(58) Field of Classification Search
USPC .......................................... 424/483, 489, 490
See application file for complete search history.

(56) References Cited

U.S. PATENT DOCUMENTS

| | | | |
|---|---|---|---|
| 2,611,730 | A | 9/1952 | Heming |
| 2,909,462 | A | 10/1959 | Warfield et al. |
| 3,499,960 | A | 3/1970 | Macek et al. |
| 3,874,907 | A | 4/1975 | Gardon et al. |
| 3,974,272 | A | 8/1976 | Polli et al. |

(Continued)

FOREIGN PATENT DOCUMENTS

| | | |
|---|---|---|
| EP | 0349453 A1 | 1/1990 |
| EP | 0730494 A1 | 9/1996 |

(Continued)

OTHER PUBLICATIONS

Johnson et al. "Sodium polystyrene sulfonate resin candy for control of potassium in chronic dialysis patients" Jun. 1976, Clinical Nephrology, vol. 5 iss. 6, abstract.*

(Continued)

*Primary Examiner* — Ali Soroush
(74) *Attorney, Agent, or Firm* — Senniger Powers LLP

(57) ABSTRACT

The present invention provides methods and compositions for the treatment of ion imbalances. In particular, the invention provides core-shell compositions and pharmaceutical compositions thereof. Methods of use of the core-shell compositions for therapeutic and/or prophylactic benefits are disclosed herein. Examples of these methods include the treatment of phosphate imbalance disorders, hypertension, chronic heart failure, end stage renal disease, liver cirrhosis, chronic renal insufficiency, fluid overload, or sodium overload.

22 Claims, 13 Drawing Sheets

U.S. PATENT DOCUMENTS

| | | | |
|---|---|---|---|
| 4,143,130 | A | 3/1979 | Imondi et al. |
| 4,470,975 | A | 9/1984 | Berger et al. |
| 4,605,701 | A | 8/1986 | Harada et al. |
| 4,747,881 | A | 5/1988 | Shaw et al. |
| 4,837,015 | A | 6/1989 | Olsen |
| 4,902,501 | A | 2/1990 | Bandi et al. |
| 4,942,205 | A | 7/1990 | Ohmori et al. |
| 5,051,253 | A | 9/1991 | Lloyd-Jones et al. |
| 5,091,175 | A | 2/1992 | Imondi et al. |
| 5,141,927 | A | 8/1992 | Krotkiewski |
| 5,186,937 | A | 2/1993 | Sparks et al. |
| 5,281,631 | A | 1/1994 | Horwitz et al. |
| 5,374,422 | A | 12/1994 | St. Pierre et al. |
| 5,401,498 | A * | 3/1995 | Kesseler et al. ............ 424/78.11 |
| 5,413,782 | A | 5/1995 | Warchol et al. |
| 5,487,888 | A | 1/1996 | Mandeville, III et al. |
| 5,607,669 | A | 3/1997 | Mandeville, III et al. |
| 5,618,530 | A | 4/1997 | Mandeville, III et al. |
| 5,633,344 | A | 5/1997 | Figuly |
| 5,667,775 | A | 9/1997 | Holmes-Farley et al. |
| 5,679,717 | A | 10/1997 | Mandeville, III et al. |
| 5,693,675 | A | 12/1997 | Mandeville, III et al. |
| 5,702,696 | A | 12/1997 | Mandeville, III et al. |
| 5,718,920 | A | 2/1998 | Notenbomer |
| 5,846,990 | A | 12/1998 | Murugesan et al. |
| 5,935,599 | A | 8/1999 | Dadey |
| 6,280,717 | B1 | 8/2001 | Kamakura et al. |
| 6,294,163 | B1 | 9/2001 | Dhal et al. |
| 6,881,484 | B2 | 4/2005 | Kataoka et al. |
| 2002/0054903 | A1 | 5/2002 | Tyler et al. |
| 2002/0054913 | A1 | 5/2002 | Heese et al. |
| 2002/0146386 | A1 | 10/2002 | Simon et al. |
| 2003/0027789 | A1 | 2/2003 | Yamaoka et al. |
| 2003/0065090 | A1 | 4/2003 | Kelly et al. |
| 2004/0166156 | A1 | 8/2004 | Tyler et al. |
| 2004/0251204 | A1 | 12/2004 | Paananen et al. |
| 2005/0036983 | A1 | 2/2005 | Simon et al. |
| 2005/0220751 | A1 | 10/2005 | Charmot et al. |
| 2005/0220752 | A1 | 10/2005 | Charmot et al. |
| 2005/0220889 | A1 | 10/2005 | Charmot et al. |
| 2005/0220890 | A1 | 10/2005 | Charmot et al. |
| 2006/0024336 | A1 | 2/2006 | Charmot et al. |

FOREIGN PATENT DOCUMENTS

| | | | |
|---|---|---|---|
| EP | 0730494 | B1 * | 9/1996 |
| JP | 1998-059851 | A | 3/1998 |
| JP | 1998-130154 | A | 5/1998 |
| JP | 2004-149525 | A | 5/2004 |
| WO | 82/00257 | A1 | 2/1982 |
| WO | 92/10522 | A1 | 6/1992 |
| WO | 94/27619 | A1 | 12/1994 |
| WO | 95/14531 | A1 | 6/1995 |
| WO | 97/49387 | A1 | 12/1997 |
| WO | 97/49736 | A2 | 12/1997 |
| WO | 00/40224 | A1 | 7/2000 |
| WO | 01/51063 | A1 | 7/2001 |
| WO | 02/12160 | A1 | 2/2002 |
| WO | 02/40039 | A2 | 5/2002 |
| WO | 02/062356 | A2 | 8/2002 |
| WO | 2005/065291 | A2 | 7/2005 |

OTHER PUBLICATIONS

Moberly et al. "Alterations in lipoprotein compositions in peritoneal dialysis patients" Mar. 2002, Peritoneal Dialysis International, vol. 22, pp. 220-228.*

Agarwal, et al., "Pathophysiology of Potassium Absorption and Secretion by the Human Intestine", Gastroenterology, 1994, pp. 548-571, vol. 107, American Gastroenterological Association.

Berlyne, G. M., et al., "Cation Exchange Resins in Hyperkalaemic Renal Failure", Israel J. Med Sci., 1967, pp. 45-52, vol. 3, No. 1.

Blake, J., M.D., et al., "Differential Effects of Direct Antagonism of All Compared to ACE Inhibitors on Serum Potassium Levels and Azotemia in Patients with Severe Congestive Heart Failure," Congestive Heart Failure, Jul./Aug. 2000, pp. 193-196, vol. 6, No. 4, CHF, Inc., Darien, Connecticut.

Chourasia, M. K., et al., "Pharmaceutical Approaches to Colon Targeted Drug Delivery Systems", J. Pharm Pharm Sci., 2003, pp. 33-66, vol. 6, No. 1.

Coli, L., et al., "Phosphate Removal by Resin Hemoperfusion Efficacy and Biocompatibility of a New Exchange Resin", Biomaterials, Artificial Cells, and Immobilization Biotechnology, 1992, pp. 1153-1163, vol. 20, No. 5.

Corcoran, A. C., et al., "Controlled Observations on the Effect of Low Sodium Dietotherapy in Essential Hypertension", Circulation, 1951, pp. 1-16, vol. 3, No. 1.

Cuna, M. et al., "Controlled-Release Liquid Suspensions Based on Ion-Exchange Particles Entrapped Within Acrylic Microcapusles", International Journal of Pharmaceutics, 2000, pp. 151-158, vol. 199, Elsevier Science.

Dai, et al., "Controlling Ion Transport through Mulitlayer Polyelectrolyte Membranes by Derivatization with Photolabile Functional Groups", Macromolecules, 2002, pp. 3164-3170, vol. 35, American Chemical Society.

Danowski, T. S., et al., "Changes in Fecal and Serum Constituents During Ingestion of Cation and Anion Exchangers", Ann N Y Acad. Sci., 1953, pp. 273-279, vol. 57, No. 3.

Emerson Jr., K., et al., "The Role of the Gastro-Intestinal Tract in the Adaptation of the Body to the Prevention of Sodium Depletion by Cation Exchange Resins", Ann N Y Acad Sci., 1953, pp. 280-290, vol. 57, No. 3.

Emmett, M., et al., "Effect of Three Laxatives and a Cation Exchange Resin on Fecal Sodium and Potassium Excretion", Gastroenterology, 1995, pp. 752-760, vol. 108, No. 3.

EP Search Report for counterpart foreign Application No. 05731099 dated May 8, 2007, 3 pages.

EP Search Report for counterpart foreign Application No. 05732849 dated May 8, 2007.

Estrela-Lopis, et al., "SANS Studies of Polyelectrolyte Multilayers on Colloidal Templates", Langmuir, 2002, pp. 7861-7866, vol. 18, American Chemical Society.

Evans, B. M., et al., "Ion-Exchange Resins in the Treatment of Anuria", Lancet, 1953, pp. 791-795, vol. 265, No. 6790.

Field, Jr., H., et al., "Electrolyte Changes in Ileal Contents and in Feces During Restriction of Dietary Sodium With and Without the Administration of Cation-Exchange Resin", Circulation, 1955, pp. 625-629, vol. 12, No. 4.

Field, Jr., H., et al., "Mechanisms Regulating the Retention of Sodium in the Feces by Cation-Exchange Resin: Release of Base from the Resin by Bacterial Fermentation in the Terminal Ileum", J. Lab Clin Med., 1958, pp. 178-184, vol. 51, No. 2.

Forrest, M. L., et al., "A Degradable Polyethylenimine Derivative with Low Toxicity for Highly Efficient Gene Delivery", Bioconjugate Chem., 2003, pp. 934-940, vol. 14, No. 5.

Fourman, P., "Capacity of a Cationic Exchange Resin (zeo-karb 225) In Vivo" British Medical Journal, 1953, pp. 544-546, vol. 1, No. 4809.

Friedman, E. A., "Clinical Aspects of Uremia and Dialysis/Sorbent Therapy in Uremia", 1976, pp. 671-687.

Friedman, E. A., et al., "Combined Oxystarch-Charcoal Trial in Uremia: Sorbent-induced Reduction in Serum Cholesterol", Kidney International, 1976, pp. S273-S276, vol. 10.

Gerstman, et al., "Use of Sodium Polystyrene Sulfonate in Sorbitol in the United States", American Journal of Kidney Diseases, Nov. 1991, pp. 619-621, vol. XVIII, No. 5.

Greenman, L., et al., "Biochemical Changes Accompanying the Ingestion of a Carboxylic Cation Exchanger in the Hydrogen, Ammonium, Sodium, Potassium, or Calcium Form", J. Clin Invest., 1951, pp. 995-1008, vol. 30, No. 9.

Gruy-Kapral, C., et al., "Effect of Single Dose Resin-Cathartic Therapy on Serum Potassium Concentration in Patients With End-Stage Renal Disease", J. Am. Soc. Nephrol, 1998, pp. 1924-1930, vol. 9, No. 10.

Harthon, J. G. L., et al., "A Case of Uremia and Hyperpotassemia Treated With Sulphonic Cation-Exchange Resin", Acta Med. Scan, 1952, pp. 230-236, vol. 144, No. 3.

Heming, A. E., et al., "Considerations in the Selection of Cation Exchange Resins for Therapeutic Use", Ann N Y Acad Sci., 1953, pp. 239-251, vol. 57, No. 3.

Ichikawa, H. et al., "Use of Ion-Exchange Resins to Prepare 100 μm-sized Microcapsules with Prolonged Drug-Release by the Wurster Process", International Journal of Pharmaceutics, 2001, pp. 67-76, vol. 216, Elsevier Science.

Imondi, A. R., et al., "Gastrointestinal Sorbents for the Treatment of Uremia I. Lightly Cross-Linked Carboxyvinyl Polymers", Ann Nutr Metabol., 1981, pp. 311-319, vol. 25, No. 5.

Irwin, L., et al., "The Effect of a Cation Exchange Resin on Electrolyte Balance and Its Use in Edematous States", J. Clin Invest., 1949, pp. 1403-1411, vol. 28, No. 6, Part 2.

Johnson, K., et al., "Sodium Polystyrene Sulfonate Resin Candy for Control of Potassium in Chronic Dialysis Patients," Clinical Nephrology, 1976, pp. 266-268, vol. 5, No. 6.

Kim, et al., "Therapeutic Approach to Hyperkalemia", Nephron, 2002, pp. 33-40, vol. 92, Supplement 1, Division of Nephrology, Department of Internal Medicine, Hanyang University Kuri Hospital, Kuri, Korea.

Kohlstaedt, K. G., et al., "Clinical Experience With Mixtures of Anion and Cation Exchange Resins", Ann N Y Acad Sci., 1953, pp. 260-272, vol. 57, No. 3.

Koping-Hoggard, M., et al., "Chitosan as a Nonviral Gene Delivery System. Structure-Property Relationships and Characteristics Compared with Polyethylenimine In Vitro and After Lung Administration In Vivo", Gene Therapy, 2001, pp. 1108-1121, vol. 8.

Mason, N. S., et al., "A New Ion Exchanger With High In Vivo Sodium Capacity" Kidney Int. Suppl., 1985, pp. S178-S182, vol. 28, No. 17.

Mateer, F. M., et al., "Sodium Restriction and Cation Exchange Resin Therapy in Nephrotic Children", J Clin Invest, 1951, pp. 1018-1026, vol. 30, No. 9.

McChesney, E.W., "Effects of Long-Term Feeding of Sulfonic Ion Exchange Resin on the Growth and Mineral Metabolism of Rats", Am. J. Physiol., 1954, pp. 395-400, vol. 177, No. 3.

McChesney, E. W., et al., "Some Aspects of Cation Exchange Resins as Therapeutic Agents for Sodium Removal", Ann N Y Acad Sci., 1953, pp. 252-259, vol. 57, No. 3.

Meszaros, et al., "Adsorption of Poly(ethyleneimine) on Silica Surfaces: Effect of pH on the Reversibility of Adsorption", Langmuir, 2004, pp. 5026-5029, vol. 20, American Chemical Society.

Moustafine, R. I., et al., "Characteristics of Interpolyelectrolyte Complexes of Eudragit E 100 With Sodium Alginate", Int. J. Pharm., 2005, pp. 113-120, vol. 294, Nos. 1-2.

Picart, et al., "Microinterferometric Study of the Structure, Interfacial Potential, and Viscoelastic Properties of Polyelectrolyte Multilayer Films on a Planar Substrate", J. Phys. Chem. B, 2004, pp. 7196-7205, vol. 108, American Chemical Society.

Root, M. A., "Comparison of the In Vivo Sodium-Removing Activity of Various Types of Ion Exchange Resins in Rats", J. Lab. Clin. Med., 1953, pp. 430-437, vol. 42, No. 3.

Ross, E. J., et al., "Observations on Cation Exchange Resins in the Small and Large Intestines", 1954, pp. 555-566, Medical Unit, University College Hospital Medical School, London, W.C.1.

Salas-Coll, et al., "Potassium Transport Across the Distal Colon in Man", Clinical Science and Molecular Medicine, 1976, pp. 287-296, vol. 51.

Spencer, et al., "Cation Exchange in the Gastrointestinal Tract", 1954, pp. 603-606, Medical Unit, University College Hospital Medical School, London, W.C.1.

Thies, C., "Microcapsules as Drug Delivery Devices," Crit Rev Biomed Eng., 1982, pp. 335-383, vol. 8, No. 4.

Thomas, M., et al., "Cross-Linked Small Polyethylenimines: While Still Nontoxic, Deliver DNA Efficiently to Mammalian Cells In Vitro and In Vivo", Pharmaceutical Research, 2005, pp. 373-380, vol. 22, No. 3.

Tust, R. H., et al., "The Effects of Malethamer on the Excretion and Plasma Levels of Sodium, Potassium, and Chloride (34990)", Proc. Soc. Exp. Biol. Med., 1970, pp. 72-76, vol. 135, No. 1.

Wrong, O., et al., "The Electrolyte Content Faeces", Proc. R. Soc. Med., 1965, pp. 1007-1009, vol. 58, No. 12.

Wrong, O.M., "Role of the Human Colon in Homeostasis," Scientific Basis of Medicine Annual Reviews, 1971, pp. 192-215.

Wrong, et al., "In Vivo Dialysis of Feces as a Method of Stool Analysis", Clinical Science, 1965, pp. 357-375, vol. 28.

\* cited by examiner

ION BINDING COMPOSITIONS

CROSS-REFERENCE

This application is a continuation of U.S. application Ser. No. 11/095,918, filed Mar. 30, 2005, which is a continuation-in-part of U.S. application Ser. No. 10/965,274, filed Oct. 13, 2004 which is a continuation-in-part application of U.S. application Ser. No. 10/814,527, filed Mar. 30, 2004; U.S. application Ser. No. 10/814,749, filed Mar. 30, 2004; and U.S. application Ser. No. 10/813,872, filed Mar. 30, 2004 which are incorporated herein by reference in their entirety.

INTRODUCTION

Ion selective sorbents have been used in human therapy to correct disorders in electrolyte balance, in conditions such as hyperphosphatemia, hyperoxaluria, hypercalcemia, and hyperkalemia. Hyperphosphatemia occurs in patients with renal failure, whose kidneys no longer excrete enough phosphate ions to compensate exogenous phosphate uptake in the diet. This condition leads to high serum phosphate concentration and high calcium×phosphate product. Although the etiology is not fully demonstrated, high calcium×phosphate product has been held responsible for soft tissue calcification and cardiovascular disease. Cardiovascular disease is the cause of death in almost half of all dialysis patients.

Aluminum, calcium, and, more recently, lanthanum salts have been prescribed to control phosphate ion absorption in the gastrointestinal (GI) tract and restore systemic phosphate levels back to normal. However these salts liberate soluble aluminum and calcium cations in the GI tract, which are then partially absorbed into the blood stream. Aluminum absorption can cause serious side effects such as aluminum bone disease and dementia; high calcium uptake leads to hypercalcemia and puts patients at risk for coronary calcification.

Metal-free phosphate binders such as strong base ion-exchanger materials, Dowex and Cholestyramine resins, have been suggested for use as phosphate binders. However, their low capacity of binding requires high dosage that is not well tolerated by patients.

Amine functional polymers have been described as phosphate or oxalate binders. For example, see U.S. Pat. Nos. 5,985,938; 5,980,881; 6,180,094; 6,423,754; and PCT publication WO 95/05184. Renagel, a crosslinked polyallylamine resin, is a phosphate sequestering material introduced in the market as a metal-free phosphate binder. In vitro phosphate binding of Renagel is approximately 6 mmol/gm in water and 2.5 mmol/gm when measured in 100 mM sodium chloride solution. The recommended dosage for the targeted patient population is typically between 5 gms/day to 15 gms/day to keep the phosphate concentration below 6 mg/dL. Published phase I clinical trials on Renagel, performed on healthy volunteers, indicate that 15 gms of Renagel decrease the phosphate urinary excretion from a baseline of 25 mmole to 17 mmole, the difference being excreted in the feces as free and polymer-bound phosphate. From these data, the in vivo capacity range can be established at 0.5-1 mmol/gm, which is much less than the in vitro capacity of 2.5 mmol/gr measured in saline. Considering only the in vitro binding capacity of Renagel measured in saline, a dosage of 15 gm of the 2.5 mmol/gm phosphate binder would bind the entire phosphorous content of the average American diet, i.e. 37 mmol/day. The discrepancy between the in vitro binding capacity and the documented low in vivo binding capacity has a negative impact on the therapeutic benefit of the drug since more resin is needed to bring the serum phosphate to a safe range.

This loss of capacity of ion-exchange resins is not limited to Renagel when used in the complex environment of the GI tract environment. For example, cation exchange resins in the sodium or ammonium form have been administered to patients with hyperkalemia. The exchange capacity of these resins were measured from isolated feces and found to be about 20% of the in vitro capacity (Agarwal, R., Gastroenterology, 1994, 107, 548-571).

Although generally safe from a toxicological perspective, the large dose and inconvenience associated with taking multigram amounts of resin (e.g., up to 15 gms/day for Renagel and considerably higher in the cases of sodium-binding resins) argues for the need to improve resin capacity. As an example, even in reported safety studies of the Renagel binder, patients have noted gastrointestinal discomfort at doses as low as 1.2-2.0 gm/day for an 8 week treatment period. Patients receiving 5.4 gm of Renagel/day were discontinued from treatment due to adverse events such as GI discomfort in 8.9% of the cases (Slatapolsky, et al Kidney Int. 55:299-307, 1999; Chertow, et al Nephrol Dial Transplant 14:2907-2914, 1999). Thus, an improvement in in vivo binding capacity that translates to lower, better tolerated dosing would be a welcome improvement in resin-based therapies.

As a result of these considerations there is still a great need for safe, high-capacity binders that selectively remove ions from the body with a lower drug dosage and a better patient compliance profile.

SUMMARY OF THE INVENTION

In one aspect, the present invention provides core-shell compositions and pharmaceutical compositions thereof. The core-shell compositions of the present invention comprise of a core component and a shell component. In a preferred embodiment, the core of the core-shell composition is a polymer and can preferentially bind one or more target solutes, e.g., in the gastrointestinal (GI) tract of an animal. In another preferred embodiment, the permeability of the shell component is modified based on the external environment.

Another aspect of the invention provides methods for treatment of patients using the core-shell compositions described herein. In a preferred embodiment, the core-shell compositions are used to remove target solutes from the GI tract. Examples of target solutes that can be removed from the GI tract include, but are not limited to, phosphate, oxalate, sodium, chloride, protons, potassium, iron, calcium, ammonium, magnesium, urea, and creatinine. In another preferred embodiment, the compositions described herein are used in the treatment of hyperphosphatemia, hypocalcemia, hyperparathyroidism, depressed renal synthesis of calcitriol, tetany due to hypocalcemia, renal insufficiency, ecotopic calcification in soft tissues, hypertension, chronic heart failure, end stage renal disease, liver cirrhosis, fluid overload, sodium overload, hyperkalemia, metabolic acidosis, renal insufficiency, and anabolic metabolism.

DETAILED DESCRIPTION OF THE INVENTION

The present invention provides core-shell polymeric compositions. Also, methods and kits for using these compositions are described herein.

Core Shell Compositions

One aspect of the invention is a core-shell composition comprising a core component and a shell component. In a preferred embodiment, the core-shell composition is a polymeric composition and the core component can preferentially bind one or more target solutes, e.g., in the gastrointestinal (GI) tract of an animal. The term "animal" and "animal subject" as used herein includes humans as well as other mammals.

Figure 1:
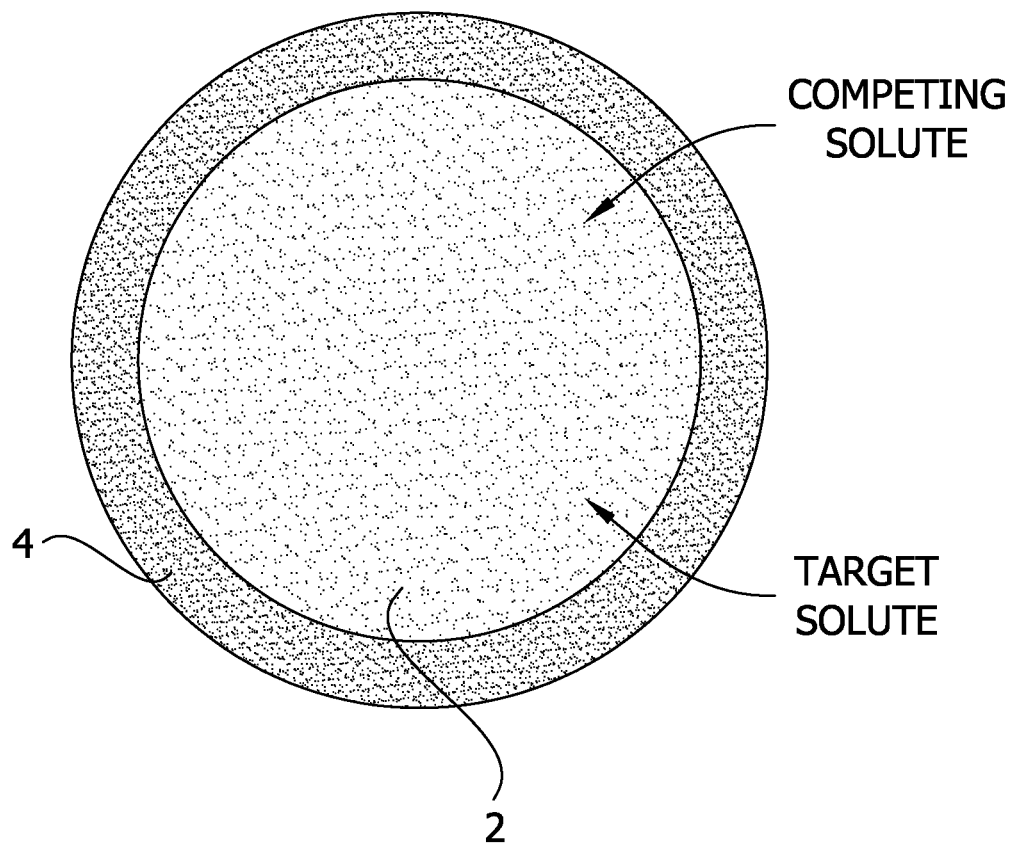
FIG. 1 is a schematic representation of one embodiment of a core-shell composition.

As shown in FIG. 1, in one embodiment, the core-shell composition comprises core-shell particles with a core component 2 and a shell component 4. The core component is capable of preferentially binding one or more target solutes and the shell component has a higher permeability for the target solutes compared to the permeability for one or more competing solutes. The size of the arrows in FIG. 1 corresponds to the magnitude of the permeability of the solutes. In preferred embodiments, the size of the core-shell composition is essentially not disintegrated during the period of residence and passage through the gastro-intestinal tract.

The term "target solute" as used herein means a solute that is preferentially bound and/or retained by the core component of the core-shell composition. It is preferred that the target solute has a higher permeability across the shell compared to one or more competing solutes. In preferred embodiments, the shell preferentially allows contact of the target solute with the core. Target solutes include both ions and non-ionic molecules. The ions include both organic and inorganic ions. The ions also include hydrophilic ions, hydrophobic ions, hydrophilic neutral molecules, and hydrophobic neutral molecules. Examples of anionic target solutes include phosphate, chloride, bicarbonate, and oxalate ions. Examples of cationic target solutes include protons, sodium, potassium, magnesium, calcium, ammonium, and other heavy metal ions. Target solutes also include toxins such as uremic toxins. Examples of uremic toxins include urea, creatinine, and classes of compounds such as ribonucleosides, guanidines, polyols, peptides, purines, pyrimidines. See Vanholder et al., Kidney International, vol. 63, (2003), 1934-1943.

In one embodiment, the target solutes excludes high molecular weight molecules like proteins, polysaccharides, and cell debris whose molecular weight are greater than about 50,000 daltons, preferably greater than 5000 daltons. Target solutes also include non-ionic molecules such as organic and inorganic neutral molecules, as well as hydrophilic and hydrophobic neutral molecules. For example, the non-ionic molecules include biological toxins, enzymes, metabolites, drugs, bodily secretions, hormones, etc. Typically, the toxins bound by the compositions disclosed herein are less than about 10,000 daltons, preferably less than 5000 daltons, and even more preferably less than 2000 daltons. The compositions disclosed herein with suitable properties could be used to treat toxicities caused by uremia, drug overdoses or exposure to toxins such as biological toxins or chemical contaminants.

In one embodiment, the core-shell particle preferably binds target solutes, excluding bile acids. In another embodiment, the core-shell particle preferably binds a bile acid and one additional target solute which is not a bile acid.

The term "competing solute" as used herein means solutes that compete with the target solute for binding to a core component, but that are not desired to be contacted and/or bound to the core component. Typically, the competing solute for a core-shell composition depends on the binding characteristics of the core and/or the permeability characteristics of the shell component. A competing solute can be prevented from contacting and/or binding to a core-shell particle due to the preferential binding characteristics of the core component and/or the decreased permeability of the shell component for the competing solute from the external environment. Typically, the competing solute has a lower permeability from the external environment across the shell compared to that of the target solute. For example, for a core-shell composition with a core component that preferably binds phosphate ions, an example of a competing solute is bile acids and fatty acids. The bile acids and fatty acids can be kept away from the core and not be allowed to bind to the core due to the permeability barrier created by the shell component that is more permeable to phosphate ions than bile acids.

In one embodiment, the target solute is hydrophilic ions. The core-shell polymeric compositions which have hydrophilic ions as target solutes are preferably used to remove hydrophilic ions from physiological fluids. More preferably, such core-shell compositions have utility in selectively removing phosphate, oxalate and/or chloride anions. In another embodiment, the hydrophilic ions removed are sodium and/or potassium ions.

It is preferred that the core component of the core-shell particles preferentially binds at least one target solute. The term "preferential binding" and its grammatical equivalents are used herein to describe the favored binding of the target solute to the core component and/or core-shell particles compared to the binding of competing solutes. The preferential binding of target solute can be due to a higher binding affinity for target solutes compared to competing solutes. Preferential binding also encompasses an increased amount of binding of target solutes by the core component, compared to the binding of competing solutes. In some of the preferred embodiments, the core-shell particles bind a greater amount of target solute compared to the core by itself in the absence of the shell. The increased amount of binding can be from about 5% to 100%. It is preferred that the increase in binding of target solute in the presence of the shell compared to the amount bound in the absence of the shell is about 10% or greater, more preferred is about 25% or greater, even more preferred is about 50% or greater, and most preferred is about 95% or greater.

It is also preferred that the core-shell particles retain a significant amount of the bound target solute. The term "significant amount" as used herein is not intended to mean that the entire amount of the bound target solute is retained. It is preferred that at least some of the bound solute is retained, such that a therapeutic and/or prophylactic benefit is obtained. Preferred amounts of bound target solutes that are retained range from about 5% to about 100%. It is preferred that the core-shell compositions retain about 50% of the bound target solute, more preferred is about 75%, and even more preferred is greater than 95%. The period of retention of the bound sodium is preferred to be during the time that the core-shell composition is being used therapeutically and/or prophylactically. In the embodiment in which the core-shell composition is used to bind and remove target solutes from the gastro-intestinal tract, the retention period is preferred to be during the time of residence of the composition in the gastro-intestinal tract. For a topical preparation or a core-shell composition used for a local effect, the retention time is typically the period the composition is present on the topical location or the location that the local effect is desired.

In one embodiment, the core component is composed of polymers containing functional groups with specific binding properties for a given solute, i.e. the target solute. The functional groups with the desired binding properties can be incorporated in the polymer backbone or pendant to the backbone. The binding interactions between the target solutes and the functional groups of the binding core can be of various kinds including, but not limited to, acid-base, coulombic, dipolar, hydrogen bonding, covalent binding, $P_i$ interaction, and combinations thereof.

In different embodiments of the invention, the preferential binding between the target solute and the competing solutes can be controlled by the rate of sorption of solutes within the core material or by the rate of permeation of the solutes across the shell component. That is, it is possible to modify the affinity of a target solute for the core component by modifying the overall permeation rate across the particle while keeping the binding core characteristics constant. Also, it is possible to reverse the selectivity for a set of solutes for a given binding core, by creating a permeability coefficient difference in the shell.

Some of the characteristics of the shell membrane and the solutes that influence the permeation of solutes across the core-shell particles are:
- size and shape of the hydrated solute;
- degree of association/aggregation of the solute (e.g., when micelles are formed);
- charge of the solutes;
- hydration ratio of the shell;
- mesh size of the shell; and
- interaction between shell and solutes.

Other parameters also influence the overall mass transfer of solutes to the interior of the core-shell particles:
- specific surface area (i.e. particle diameter);
- thickness of the shell; and
- convection current at the outside of the particles.

When there are no chemical interactions between the polymeric composition and the solute, the diffusion can be described by Fick's first law:

$$J_s = \frac{P}{l_s}(C_o - C_i)$$

where $J_s$ is the solute flux in $g/cm^2/s$;
L is the membrane thickness (cm);
P is the permeability coefficient in $cm^2/s$; and
$C_0$-$C_i$ is the concentration gradient across the membrane.
The permeability coefficient is expressed as:

P=KD where K is a dimension-less parameter (assimilated to the solute partition coefficient between the membrane and the solution) and
D is the solute coefficient in the aqueous solution.

Several models are known to express the permeability coefficient P, such as the capillary pore model (Renkin equation) and the free volume model, among others.

In the free volume model, the polymeric composition that makes up the core and/or shell component is considered to be a homogenously hydrated network. The diffusion transport of solutes is considered to occur through fluctuating water-filled spaces within the polymeric network. The free volume diffusion model predicts that D scales with the fraction of polymer in the membrane, $\phi$, and the radius of the hydrated solute, $r_s$. A refinement has been proposed (Peppas et al., J. Appl. Polym. Sci., 36,735-747, 1988) as the hydrodynamic model:

$$\frac{D}{D_0} = k_1 \exp\left[-k' r_s^2 \left(\frac{\phi}{1-\phi}\right)\right] \text{ diffusion model}$$

$$\frac{D}{D_0} = \exp[-k_c r_s \phi^{3/4}] \text{ hydrodynamic model}$$

where D and $D_0$ are the diffusion coefficients in the membrane and the aqueous solution, respectively and
$k_1$ is related to the sieving factor, when the geometry of the solute is the critical parameter that dictates the solute progression in the core-shell composition and k' and $k_c$ are undefined structural factors.

For a target solute such as phosphate ions, a typical value of self-diffusion coefficient is $10^{-5}$ $cm^2/s$. Based on certain diffusion models, the permeation rate across a micron thick shell membrane is estimated to be extremely fast with respect to the time of use of the resin, typically hours.

If bile acid or fatty acid molecules, as the competing solutes, compete for the same core binding sites as phosphate ions, their self-diffusion coefficient is inversely proportional to their size in solution, which is not so different from one of small ions. Thus, this self-diffusion coefficient may not be enough to create a permeability barrier, if the diffusion is unhindered. Accordingly, in some embodiments, several characteristics of the shell component are tuned so that a permeation difference is established. For example, when the mesh size of the shell material is in the same size range as the solute dimensions, the random walk of the bulkier solute through the shell component is significantly slowed down. For example, experimental studies (Krajewska, B., Reactive and Functional polymers 47, 2001, 37-47) report permeation coefficients in cellulose ester or crosslinked chitosan gel membranes for both ionic and non-ionic solutes shows slowing down of bulkier solutes when mesh size nears solute dimensions. Accordingly, D values can decrease several orders of magnitude depending on the molecular size of the solutes and the polymer volume fraction in the core-shell compositions, the polymer volume fraction in the swollen resin being a good indicator of the mesh size within the composition. Theoretical studies have shown, for example, that mesh size usually scales with $\phi^{-3/4}$, $\phi$ being the polymer volume fraction in the shell component when swollen in a solution.

In some embodiments, the permeability of the solute is modulated by the degree of interaction between the solute and the shell material. A strong interaction can trap the solute inside the shell component, almost shutting down the migration across the shell. Examples of types of interaction include ionic, covalent, polar, hydrogen bonding, van der Waals, and hydrophobic interactions.

In some embodiments, depending upon the conditions of use and the type of solutes, the ratio between the diffusion coefficient of the target solute and the competing solutes through the shell, is between about 1.1:1 to about $10^9$:1, preferably between about 2:1 to about $10^6$:1.

Figure 2:
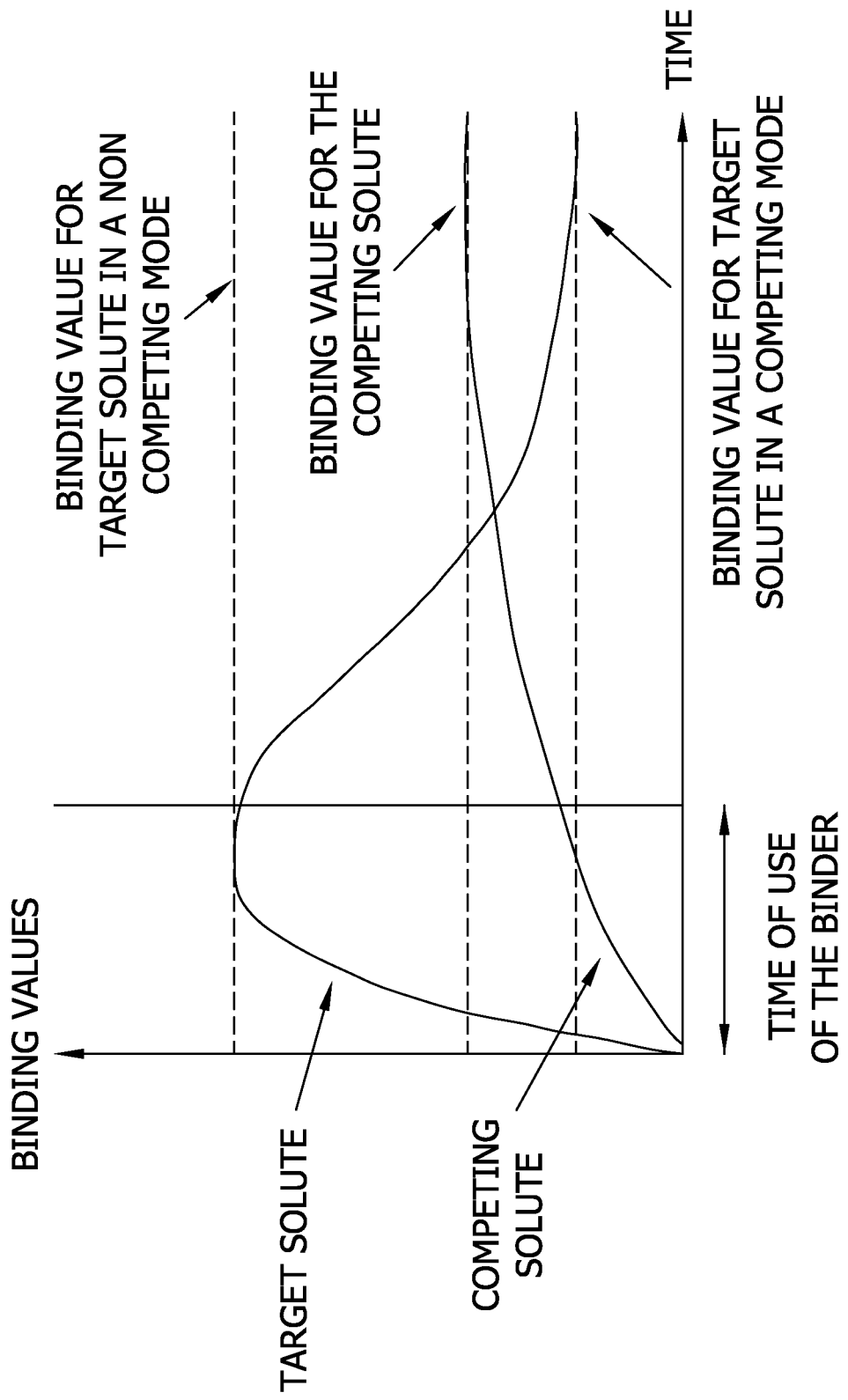
FIG. 2 depicts the solute binding profile as a function of time for some embodiments of the invention.

When the core-shell particles of the invention are used, the solute binding profile as a function of time, of some embodiments, can be schematically represented as depicted in FIG. 2. In a preferred embodiment, the target solute migrates quickly through the shell to be bound to the core material quickly attaining its binding value corresponding to a non-competing mode. In contrast, the competing solute slowly progresses through the shell as a result of its lower permeation rate; it eventually reaches its binding equilibrium value later in time and then displaces the target solute, causing a drop in the target solute binding curve. Preferably the ratio of diffusion coefficients is adjusted so that, at the end of the time of use of the binder (which may correspond to mean residence time of the resin in the GI) is less than about 10% to about 100% of the competing solutes have reached their binding equilibrium value. Preferably less than about 10%, more preferably less than about 50%, and even more preferably less than about 75% of the competing solutes have reached their binding equilibrium value. For the target solutes more than about 10% to about 100% has reached its binding equilibrium value in a non-competing mode. Preferably more than about 25%, more preferably more than about 50%, even more preferably more than about 75% of the target solute has reached its binding equilibrium.

Methods for determining diffusion coefficients are known. For example, see, W. Jost, *Diffusion in Solids, Liquids and Gases*, Acad. Press, New-York, 1960). For example, the diffusion coefficient of a shell polymer can be measured by casting it as a membrane over a solid porous material, which is then contacted with a physiological solution containing the solutes of interest, and measuring steady state permeation rates of said solutes. Membrane characteristics can then be optimized to achieve the best cooperation in terms of selectivity and permeation rate kinetics. Structural characteristics of the membrane can be varied by modifying, for example, the polymer volume fraction (in the swollen membrane), the chemical nature of the polymer(s), the polymer blend composition (if more than one polymer is used), the formulation with additives such as wetting agents, plasticizers, and the manufacturing process.

Alternatively, if the shell membrane is applied to the core material in a separate coating process, then the selectivity effect provided by the shell can be obtained by measuring the binding capacity for the target solute using the core particles with and without the shell. The increase in selectivity, SI, can be simply expressed as the ratio of those two values, i.e. $SI = CB_{core-shell}/CB_{core}$, where CB represent the capacity of binding (i.e mole of solute per unit weight of particle). Preferably, SI is between about 1.05 to about $10^4$, even more preferably from about 1.1 to about $10^2$.

In some embodiments, the shell is a film-forming polymer. In another embodiment, the shell polymer forms a crosslinked gel with a three-dimensional network structure where chains are crosslinked through covalent bonds, ionic or other bonds. In yet another embodiment, the shell material is chemically identical to the binding core material, but the crosslink density increases outward from core to shell. In another embodiment, the shell material adopts a "brush" configuration, wherein individual polymer strands are covalently attached to the core material at their termini. In this embodiment, the mesh size can be dictated by the density of chains anchored onto the surface and by the chain molecular weight. The polymer brush design variables that control the permeability of polymer brushes to solutes of various sizes and/or weights are known in the art. For example, see WO 0102452 (and references therein).

Permeability is also controlled by the interaction of the solute with the shell. A strong and, preferably, irreversible interaction of the shell with the competing solutes can trap the competing solutes within the encapsulating shell, slowing down their progression inward. One means of quantifying the degree of interaction between a solute and the shell is the free energy of mixing, particularly the free enthalpy of mixing, which can be predicted by solubility parameters. Solubility parameters provide a numerical method of predicting the extent of interaction between materials, particularly liquids and polymers. This model predicts that compounds with dissimilar solubility parameters will not co-dissolve and consequently can go through the membrane unhindered in the absence of size sieving effect. Conversely, compounds with similar solubility parameters may form a molecular solution and can be retained. Further, while solubility parameters poorly describe ionic interactions, charged solutes generally are retained by shell material of opposite charge. Also, the combination of hydrophobic and ionic interactions can be used to provide strong, often irreversible, interactions with competing solutes, resulting in higher sorption selectivity for the target solutes which display neither a hydrophobic or an ionic character.

The shell material can be chosen from natural or synthetic polymers, optionally crosslinked, alone or in combination with small molecules functional additives such as wetting agents, plasticizers, permeability enhancers, solvents, moisturizing agents, pigment, and/or dyes.

Naturally-occurring or semi-synthetic polymers include: cellulose ethers (ethyl cellulose, methyl cellulose and their copolymers), cellulose esters (cellulose acetate, cellulose propionate, cellulose phthalate, and their copolymers), hydroxypropyl cellulose, hydroxyl ethyl cellulose, chitosan, deacetylated chitosan, and the like. Other examples of possible shell materials are listed in the table below:

TABLE 1

Acrylics
AQUACOAT ® aqueous dispersions
AQUATERIC ® enteric coatings
Cellulose Acetate
Cellulose Acetate Butyrate
Cellulose Acetate Phthalate
Caseinates
Chlorinated rubber
COATERIC ® coatings
Coating butters
DARAN ® latex
Dextrins
Ethyl Cellulose
Enterics
EUDRAGITS ® polymethacrylates
Ethylene Vinyl Acetate
Fats
Fatty Acids
Gelatin
Glycerides
Gums, vegetable TABLE 1-continued Gums, vegetable
Halocarbon
Hydrocarbon resins
Hydroxy Propyl Cellulose
Hydroxy Propyl Methyl Cellulose
Hydroxy Propyl Methyl Cellulose Phthalate
KYNAR ® fluoroplastics
Maltodextrins
Methyl Cellulose
Microcrystalline wax
Milk solids
Molasses
Nylon
OPADRY ® coating systems
Paraffin wax
Phenolics
Polylactides
Polyamino acids
Polyethylene
Polyethylene glycol
Polyvinyl acetate
Polyvinyl pyrrolidone
Polyvinyl alcohol
Polyvinyl chloride
Polyvinylacetate phthalate
Polyvinylidene chloride
Proteins
Rubber, synthetic
Shellac
Silicone
Starches
Stearines
Sucrose
Surfactants
SURELEASE ® coating systems
TEFLON ® fluorocarbons
Waxes
Zein Examples of suitable synthetic polymers that can be used in the shell component include polymers produced by free radical polymerization of ethylenic monomers (acrylic and methacrylic, styrenic, dienic, vinylic), polycondensates (polyester, polyamides, polycarbonate, polysulfone), polyisocyanate, polyurea, epoxy resins, and the like.

Shell deposition over the core material can be carried out using coating techniques such as spraying, pan coating, fluidized bed (Wurster coating units), dipping, solvent coacervation, polyelectrolyte inter-complex layers, and the "layer by layer" encapsulation process. Other encapsulation processes are also applicable. For example, see Encapsulation and Controlled Release by R. A. Stephenson (Editor), David R. Karsa (Editor), 1993.

The shell can comprise several layers of distinct composition, of which one can be an enteric coating (e.g. EUDRAGIT acrylic polymers) that disintegrates and/or solubilizes at a specific location of the GI tract. Examples of suitable enteric coatings are known in the art, for example see Remington: The Science and Practice of Pharmacy by A. R. Gennaro (Editor), 20$^{th}$ Edition, 2000.

The shell can also be grown on the core component through chemical means, for example by:
chemical grafting of shell polymer to the core using living polymerization from active sites anchored onto the core polymer;
interfacial reaction, i.e., a chemical reaction located at the core particle surface, such as interfacial polycondensation; and
using block copolymers as suspending agents during the core particle synthesis.

The interfacial reaction and use of block polymers are preferred techniques when chemical methods are used. In the interfacial reaction pathway, typically, the periphery of the core particle is chemically modified by reacting small molecules or macromolecules on the core interface. For example, an amine containing ion-binding core particle is reacted with a polymer containing amine reactive groups such as epoxy, isocyanate, activated esters, halide groups to form a crosslinked shell around the core.

In another embodiment, the shell is first prepared using interfacial polycondensation or solvent coacervation to produce capsules. The interior of the capsule is then filled up with core-forming precursors to build the core within the shell capsule.

Solvent coacervation is described in the art. For example, see Leach, K. et al., J. Microencapsulation, 1999, 16(2), 153-167. In this process, typically two polymers, core polymer and shell polymer are dissolved in a solvent which is further emulsified as droplets in an aqueous phase. The droplet interior is typically a homogeneous binary polymer solution. The solvent is then slowly driven off by careful distillation. The polymer solution in each droplet undergoes a phase separation as the volume fraction of polymer increases. One of the polymer migrates to the water/droplet interface and forms a more-or less perfect core-shell particle (or double-walled microsphere).

Solvent coacervation is one of the preferred methods to deposit a controlled film of shell polymer onto the core. In one embodiment, the coacervation technique consists in dispersing the core beads in a continuous liquid phase containing the shell material in a soluble form. The coacervation process then consists of gradually changing the solvency of the continuous phase so that the shell material becomes increasingly insoluble. At the onset of precipitation some of the shell material ends up as a fine precipitate or film at the bead surface. The change in solvency can be triggered by a variety of physical chemistry means such as, but not limited to, changes in pH, ionic strength (i.e. osmolality), solvent composition (through addition of solvent or distillation), temperature (e.g when a shell polymer with a LCST (lower critical solution temperature) is used), pressure (particularly when supercritical fluids are used). More preferred are solvent coacervation processes when the trigger is either pH or solvent composition. Typically when a pH trigger event is used and when the polymer is selected from an amine type material, the shell polymer is first solubilized at low pH. In a second step the pH is gradually increased to reach the insolubility limit and induce shell deposition; the pH change is often produced by adding a base under strong agitation. Another alternative is to generate a base by thermal hydrolysis of a precursor (e.g. thermal treatment of urea to generate ammonia). The most preferred coacervation process is when a ternary system is used comprising the shell material and a solvent/non-solvent mixture of the shell material. The core beads are dispersed in that homogeneous solution and the solvent is gradually driven off by distillation. The extent of shell coating can be controlled by on-line or off-line monitoring of the shell polymer concentration in the continuous phase. In the most common case where some shell material precipitates out of the core surface either in a colloidal form or as discrete particle, the core-shell particles are conveniently isolated by simple filtration and sieving. The shell thickness is typically controlled by the initial core to shell weight ratio as well as the extent of shell polymer coacervation described earlier. The core-shell beads can then be annealed to improve the integrity of the outer membrane as measured by competitive binding.

In some embodiments, using the block copolymer approach, an amphiphilic block copolymer can be used as a suspending agent to form the core particle in an inverse or direct suspension particle forming process. When an inverse water-in-oil suspension process is used, then the block copolymer comprises a first block soluble in the continuous oil phase and another hydrophilic block contains functional groups that can react with the core polymer. When added to the aqueous phase, along with core-forming precursor, and the oil phase, the block copolymer locates to the water-in-oil interface and acts as a suspending agent. The hydrophilic block reacts with the core material, or co-reacts with the core-forming precursors. After the particles are isolated from the oil phase, the block copolymers form a thin shell covalently attached to the core surface. The chemical nature and length of the blocks can be varied to vary the permeation characteristics of the shell towards solutes of interest.

In systems which combine positive charges and hydrophobicity, preferred shell polymers include amine functional polymers, such as those disclosed above, which are optionally alkylated with hydrophobic agents.

Alkylation involves reaction between the nitrogen atoms of the polymer and the alkylating agent (usually an alkyl, alkylaryl group carrying an amine-reactive electrophile). In addition, the nitrogen atoms which do react with the alkylating agent(s) resist multiple alkylation to form quaternary ammonium ions such that less than 10 mol % of the nitrogen atoms form quaternary ammonium ions at the conclusion of alkylation.

Preferred alkylating agents are electrophiles such as compounds bearing functional groups such as halides, epoxides, esters, anhydrides, isocyanate, or αβ-unsaturated carbonyls. They have the formula Rx where R is a C1-C20 alkyl (preferably C4-C20), C1-C20 hydroxy-alkyl (preferably C4-C20 hydroxyalkyl), C6-C20 aralkyl, C1-C20 alkylammonium (preferably C4-C20 alkyl ammonium), or C1-C20 alkylamido (preferably C4-C20 alkyl amido) group and X includes one or more electrophilic groups. By "electrophilic group" it is meant a group which is displaced or reacted by a nitrogen atom in the polymer during the alkylation reaction. Examples of preferred electrophilic groups, X, include halide, epoxy, tosylate, and mesylate group. In the case of, e.g., epoxy groups, the alkylation reaction causes opening of the three-membered epoxy ring.

Examples of preferred alkylating agents include a C3-C20 alkyl halide (e.g., an n-butyl halide, n-hexyl halide, n-octyl halide, n-decyl halide, n-dodecyl halide, n-tetradecyl halide, n-octadecyl halide, and combinations thereof); a C1-C20 hydroxyalkyl halide (e.g., an 11-halo-1-undecanol); a C1-C20 aralkyl halide (e.g., a benzyl halide); a C1-C20 alkyl halide ammonium salt (e.g., a (4-halobutyl) trimethylammonium salt, (6-halohexyl)trimethyl-ammonium salt, (8-halooctyl)trimethylammonium salt, (10-halodecyl)trimethylammonium salt, (12-halododecyl)-trimethylammonium salts and combinations thereof); a C1-C20 alkyl epoxy ammonium salt (e.g., a (glycidylpropyl)-trimethylammonium salt); and a C1-C20 epoxy alkylamide (e.g., an N-(2,3-epoxypropane)butyramide, N-(2,3-epoxypropane) hexanamide, and combinations thereof). Benzyl halide and dodecyl halide are more preferred.

The alkylation step on the polyamine shell precursor can be carried out in a separate reaction, prior to the application of the shell onto the core beads. Alternatively the alkylation can be done once the polyamine shell precursor is deposited onto the core beads. In the latter case, the alkylation is preferably performed with an alkylating agent that includes at least two electrophilic groups X so that the alkylation also induces crosslinking within the shell layer. Preferred polyfunctional alkylation agents include di-halo alkane, dihalo polyethylene glycol, and epichlorohydrine. Other crosslinkers containing acyl chlorides, isocyanate, thiocyanate, chlorosulfonyl, activated esters (N-hydroxysuccinimide), carbodiimide intermediates, are also suitable.

Typically, the level of alkylation is adjusted depending upon the nature of the polyamine precursor and the size of the alkyl groups used on alkylation. Some factors that play a role in the level of alkylation include:

(a) Insolubility of the shell polymer under conditions of the GI tract. In particular, the low pH's prevailing in the stomach tend to solubilize alkylated polyamine polymers whose pH of ionization is 5 and above. For that purpose higher rate of alkylation and higher chain length alkyl are preferred. As an alternative, one may use an enteric coating to protect the shell material against acidic pH's, said enteric coating is released when the core-shell beads are progressing in the lower intestine.

(b) The permselectivity profile: When the alkylation ratio is low the persistence of the permselectivity for competing ions (e.g. $Mg^{2+}$, $Ca^{2+}$) can be shorter than the typical residence time in the colon. Conversely when the alkylation ratio (or the weight fraction of hydrophobes) is high then the material becomes almost impermeable to most inorganic cations, and thus, the rate of equilibration for $K^+$ becomes long.

Preferably, the degree of alkylation is selected by an iterative approach monitoring the two variables mentioned above.

In a preferred embodiment, the shell is formed with EUDRAGIT, for example EUDRAGIT RL 100 or RS 100 or a combination thereof, or with polyethyleneimine (PEI). These shells maybe applied by solvent coacervation technique. The PEI may be optionally benzylated and also optionally cross-linked. Examples of suitable cross-linkers include, but are not limited to,

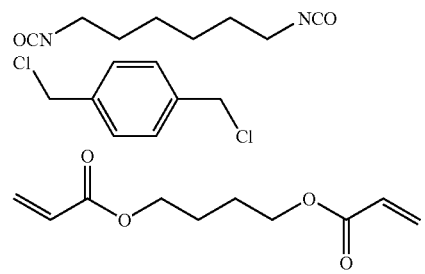

In some embodiments, the shell thickness can be between about 0.002 micron to about 50 micron, preferably about 0.005 micron to about 20 microns. Preferably the shell thickness is more than about 1 micron, more preferred is more than about 10 micron, even more preferred is more than about 20 micron, and most preferred is more than about 40 micron. Preferably the shell thickness is less than about 50 micron, more preferred is less than about 40 micron, even more preferred is less than about 20 micron, and most preferred is less than about 10 micron.

In another embodiment, the shell to core weight ratio comprises between about 0.01% to about 50%, preferably between about 0.2% to about 10%. The size of the core-shell particles typically range from about 200 nm to about 2 mm, preferably being about 500 μm. Preferably the size of the core-shell particles are more than about 1 μm, more preferred is more than about 100 μm, even more preferred is more than about 200 µm, and most preferred is more than about 400 µm. Preferably the size of the core-shell particles are less than about 500 µm, more preferred is less than about 400 µm, even more preferred is less than about 200 µm, and most preferred is less than about 100 µm.

The binding selectivity of the core can be assessed by standard methods. One method consists of measuring the binding capacity of the target solute in a simple model solution with non interfering species, Cm, and in a simulant medium (Cs), and calculating a selectivity index as SI=Cs/Cm. The core-shell particles of the invention are expected to have selectivity indexes SI significantly higher than those reported for known prior-art sorbent resins.

In one embodiment, the permeability of the shell changes as a function of time. In particular, the permeability of the shell may change over time when used in vivo. For example, in certain applications it is preferable to either diminish or conversely increase the permeability to target solutes over time during residence in a GI tract. For example, the resin could bind a hydrophilic ionic solute at a certain location of the GI tract at a rate controlled by the solute concentration in equilibrium with the resin at that location. As the resin travels down the GI tract, the local target solute concentration may vary as a result of dilution or solute transport across the gut membrane. In this embodiment, the shell material is engineered to respond to such concentration or other physiological changes in the GI, so that its permeability is altered; more specifically, the permeability of the shell maybe decreased during its journey through the GI so that hydrophilic ions are no longer able to cross the shell membrane, during the later period of the core-shell composition's residence in the GI tract. This embodiment also applies to more hydrophobic solutes such as bile acids. In the case of bile acid sequesterants, studies have shown that the poor binding rate in vivo is caused by the release of bile acids past the ileum segment of the gut. At that point, bile acids are almost quantitatively reabsorbed by the mucosa, so that the binding equilibrium is shifted and the sequestering capacity is lowered. In this embodiment, the shell component has a permeability trigger that decreases the permeability of the shell to bile acids, when the core-shell resin passes the ileum so that the overall capacity is conserved.

One manner of achieving this loss of permeability to hydrophilic ions involves decreasing or even eliminating the free volume of permeation of the shell membrane. The free volume of permeation of the membrane can be modified by controlling the hydration rate of the shell. In this manner, it is possible to almost shut down the rate of permeation by inducing a shell collapse. While there are many ways to induce such a phase change, the preferred approach consists of rendering the membrane material increasingly hydrophobic so that the hydration rate decreases almost to zero. This can be accomplished through several ways depending upon the type of triggering mechanism. For example the triggering mechanism can be by pH change. The pH profile of the gastrointestinal tract presents several domains which may change as a function of time, but show some invariants indicated below (Fallinborg et al. *Aliment. Pharm. Therap.* (1989), 3,605-613):

TABLE 2

| GI tract segment | Ph range |
| --- | --- |
| Stomach | 1-2 |
| Duodenum-distal small intestine | 6-7 |
| Ceacum-ascending colon | 7-5.5 |

TABLE 2-continued

| GI tract segment | Ph range |
| --- | --- |
| Transverse-descending colon | 5.5-6 |
| Feces | 6.5 |

Shell polymers exhibiting a chain collapse in any of these pH regions would be prone to permeability changes. For instance, core-shell particles suitable for binding a solute selectively in the stomach and keeping it in the particle core while the particles are moving down the small and large intestine, would display high permeability to solutes at low pH and very low permeability at neutral pH. This can be done by having a shell polymer with hydrophobic groups and groups that ionize subject to pH change. For example, polymers built from hydrophobic monomers (e.g. long chain alcohol (meth)arylates, Nalkyl(meth)acrylamide), and basic monomers that ionize at low pH and remain neutral beyond their pKa (e.g. vinyl-pyridine, dialkylaminoethyl (meth)acrylamide) can be used. The relationship between pH and shell swelling ratio, and hence permeability, can be controlled by the balance of hydrophobic monomers and ionizable monomers. Examples of such systems are reported in the literature. For example, see Batich et al, *Macromolecules,* 26, 4675-4680.

A further drop in permeability may be desirable when pH increases (e.g. from ileum to colon) to prevent bound electrolytes being released as the resin environment changes. This can be achieved where the shell material switches from a hydrated state to a collapsed, impermeable state as the pH gets slightly basic. In such embodiments, shell polymers typically contain a balanced amount of hydrophobic and acidic monomers. Such systems are extensively described in the literature. For example, see Kraft et al. *Langmuir,* 2003, 19, 910-915; Ito et al, *Macromolecule*, (1992), 25, 7313-7316.

Another means of changing shell permeability is by passive absorption. As described above, components present in the GI tract, whether coming from the diet, produced as diet digest metabolites, from secretion, etc. are susceptible to adsorption on and within the shell in a quasi-irreversible manner and this adsorption may modify the permeability pattern by inducing membrane collapse. The vast majority of these GI tract components is negatively charged and shows various levels of hydrophobicity. Some of these species have an amphiphilic character, such as fatty acids, bile acids, phospholipids, and biliary salts and behave as surfactants. Surfactants can adsorb non-specifically to surfaces through hydrophobic interactions, ionic interaction and combinations thereof. In the context of the present invention, this phenomenon can be used to change the permeability of the resin upon the course of binding to these surfactants during the resin's residence in the GI tract.

For example, fatty acids and bile acids both form insoluble complexes when mixed with positively charged polymers. For example, see Kaneko et al, *Macromolecular Rapid* Communications, 2003, 24(13), 789-792). Both types of molecules present similarities with synthetic anionic surfactants, and numerous studies report the formation of insoluble complexes between anionic surfactants and cationically charged polymers. For example, see Chen, L. et al, *Macromolecules* (1998), 31(3), 787-794. In this embodiment, the shell material is selected from copolymers containing both hydrophobic and cationic groups, so that the shell forms a complex, preferably a tight complex, with anionically charged hydrophobes typically found in the GI tract, such as bile acids, fatty acids, bilirubin and related compounds. Suitable compositions also include polymeric materials described as bile acids sequestering agents, such as those reported in U.S. Pat. No. 5,607,669, U.S. Pat. No. 6,294,163, U.S. Pat. No. 5,374,422, Figuly et al, *Macromolecules,* 1997, 30, 6174-6184. The formation of this complex induces a shell membrane collapse which in turn lowers or shuts down the permeation rate across the said membrane.

The shell permeability may also be modulated by enzymatic transformation. In one embodiment the shell comprises a hydrophobic backbone with pendant hydrophilic entities that are cleaved off via an enzymatic reaction in the gut. As the enzymatic reaction proceeds, the polymer membrane becomes more and more hydrophobic, and turns from a high swollen, high permeability material to a fully collapsed low hydration membrane with minimal permeability. Hydrophilic entities can be chosen amongst natural substrates of enzymes commonly secreted in the GI tract. Such entities include amino acids, peptides, carbohydrates, esters, phosphate esters, oxyphosphate monoesters, O- and S-phosphorothioates, phosphoramidates, thiophosphate, azo groups and other similar entities. Examples of enteric enzymes which can be used to chemically alter the shell polymer include, but are not limited to, lipases, phospholipases, carboxylesterase, glycosidases, azoreductases, phosphatases, amidases and proteases.

In some embodiments, the core material is chosen from polymer compositions with the desired ion binding properties. Examples of suitable polymers material include, but are not limited to:
 1) anion binding materials such as amine functional polymers such as those described in U.S. Pat. Nos. 5,985,938; 5,980,881; 6,180,094; 6,423,754; and PCT publication WO 95/05184 and
 2) cation exchange polymers, such as those with acid functional groups such as carboxylate, phosphonate, sulfate, sulfonate, sulfamate functional polymers and combinations thereof.

Core-shell compositions that include anion binding materials are useful for the binding and removal from GI tract of phosphate, chloride, bicarbonate, and oxalate ions. The cation exchange polymers have utility in binding and removal of physiologically important cations such as protons, sodium, potassium, magnesium, calcium, ammonium, and the like or heavy metals which cause poisoning.

Examples of other suitable polymers for the core component are described in the following co-pending patent applications: 1) Polyamine Polymers, filed on Nov. 3, 2003, application Ser. No. 10/701,385 and 2) Crosslinked Amine Polymers, filed on Mar. 22, 2004, application Ser. No. 10/806,495.

Further examples of compositions that can be used in the core component include the phosphate binders in PCT publications WO 94/19379, WO 96/25440, WO 01/28527, WO 02/85378, WO 96/39156, WO 98/42355, WO 99/22743, WO 95/05184, WO 96/21454, and WO 98/17707; U.S. Pat. Nos. 5,698,190; 5,851,518; 5,496,545; 5,667,775; 6,083,495; and 6,509,013; and European Patent Application 01200604.5.

Aluminum, calcium, and lanthanum salts are used as phosphate binders. Examples of inorganic metal salts used as phosphate binders include aluminum carbonate, aluminum hydroxide gel (Amphojel®), calcium carbonate, calcium acetate (PhosLo), and lanthanum carbonate (Fosrenol). In one embodiment, the core-shell particle comprises of a core component comprising of a metal phosphate binder, such as aluminum carbonate, aluminum hydroxide gel, calcium carbonate, calcium acetate, and lanthanum carbonate.

In one embodiment, the core component has sodium ion binding properties. Suitable polymers that can be used in the core so as to impart the core sodium-binding properties include crown ethers. Crown ethers exhibit selectivity for certain alkali metals over others, based mainly on the hole-size of the crown ether size and the size of the metal. Crown ethers of the type 15-18 are preferred for use in sodium ion binding core components. Also, other suitable compositions for sodium binding properties are described in co-pending patent application entitled "Methods and Compositions for Treatment of Ion Imbalances," filed on Mar. 30, 2004, application Ser. No. 10/814,527.

Uses of the Core-Shell Compositions

In one aspect, the invention provides methods of preferentially binding solutes in a mammal, comprising the step of administering to the mammal a therapeutically effective amount of core-shell compositions. Core shell compositions that bind hydrophillic cations and/or anions can be used to control ion homeostasis and treat electrolyte balance disorders in phosphate (hyperphosphatemia), oxalate (calcium oxalate kidney stones, oxaluria), sodium (hypertension), potassium (hyperkalemia), chloride (acidosis), or to remove toxic metals or oxidative anions in cases of poisoning.

The core-shell compositions with anion exchange resins are particularly useful in the binding and excretion of negatively charged ions from the body. Core-shell compositions can also be used to bind metallic ions. These compositions can be administered orally to bind and remove from an animal various negatively charged entities and metallic species from the gastro-intestinal tract. In one embodiment, the core-shell compositions of the present invention are used to remove phosphate, oxalate, bile acids, small molecules, proteins, metallic ions such as those comprised within the 6th and the 11th groups and 4th and 6th periods of the Periodic Table, also including the Lanthanoids and the Actanoids.

In some embodiments, the core-shell compositions with polyvicinalamines, such as those described in co-pending U.S. patent application Ser. No. 10/701,385; entitled Polyamine Polymers, filed on Nov. 3, 2003 are useful in the treatment of renal diseases, hyperphosphatemia, and the removal of bile acids, oxalates and iron from the gastrointestinal tract.

In some embodiments, the core-shell compositions are used in the treatment of phosphate imbalance disorders. The term "phosphate imbalance disorder" as used herein refers to conditions in which the level of phosphorus present in the body is abnormal. One example of a phosphate imbalance disorder includes hyperphosphatemia. The term "hyperphosphatemia" as used herein refers to a condition in which the element phosphorus is present in the body at an elevated level. Typically, a patient is often diagnosed with hyperphosphatemia if the blood phosphate level is, for example, above 4.5 milligrams per deciliter of blood and/or glomerular filtration rate is reduced to, for example, more than about 20%

Other diseases that can be treated with the methods and compositions of the present invention include hypocalcemia, hyperparathyroidism, depressed renal synthesis of calcitriol, tetany due to hypocalcemia, renal insufficiency, and ecotopic calcification in soft tissues including calcifications in joints, lungs, kidney, conjuctiva, and myocardial tissues. Also, the present invention can be used to treat ESRD and dialysis patients. In one embodiment, the core-shell compositions are used for prophylactic treatment of diseases.

The core-shell compositions described herein can also be used to treat diseases wherein a reduction in physiological levels of salt is desired. The core-shell compositions, depending on the ion binding properties of the core component, can be used to remove cations such as sodium and/or anions such as chloride.

In one embodiment, the core-shell compositions of the present invention are used to treat metallic poisoning, like iron poisoning. Iron poisoning typically is a result of children inadvertently taking iron supplement tablets. In iron overdose, binding of iron to oral charcoal, bicarbonate, deferoxamine, or magnesium hydroxide are typical treatments. Gastric lavage and profuse oral fluids are used to try to flush out the iron tablets. Non-absorbable core-shell compositions with iron chelating properties can be used for removal of metallic iron.

Depending on the properties of the core and/or shell components, the core-shell compositions of the present invention also show utility in binding dietary oxalate in patients who suffer from hyperoxaluria, i.e. abnormally high levels of oxalate in the urine. Elevated urine oxalate levels are one of the causes of calcium-stone formation (i.e., kidney stones). Most calcium stones are composed of calcium oxalate, either alone or in combination with calcium phosphate or calcium urate. Elevated urinary oxalate levels can result from excessive dietary intake of oxalate (dietary oxaluria), gastrointestinal disorders that lead to malabsorption of oxalate (enteric oxaluria), or an inherited enzyme deficiency that results in excessive metabolism of oxalate (primary hyperoxaluria or PH). Dietary and enteric oxaluria can be treated with diet restriction or modifications to restrict intake of foods with high oxalate content. However patient compliance is often difficult owing to the wide distribution of oxalate and purine derivatives in many foods. Calcium carbonate tablets (500-650 mg/tablet; 3 tablets per meal) can also be taken to bind and remove intestinal oxalate, but again patient compliance is difficult owing to the amount of calcium carbonate needed. Core components made of polyvicinalamines, such as those described co-pending U.S. patent application Ser. No. 10/701,385; entitled Polyamine Polymers, filed on Nov. 3, 2003, have high binding constants for oxalate and can be used to remove oxalate from the gastro-intestinal tract and subsequently lower the risk of kidney stone formation.

In the present invention, the core-shell compositions can be co-administered with other active pharmaceutical agents depending on the condition being treated. This co-administration can include simultaneous administration of the two agents in the same dosage form, simultaneous administration in separate dosage forms, and separate administration. For example, for the treatment of hyperphosphatemia, the core-shell compositions can be co-administered with calcium salts which are used to treat hypocalcemia resulting from hyperphosphatemia. The calcium salt and core-shell composition can be formulated together in the same dosage form and administered simultaneously. Alternatively, the calcium salt and core-shell composition can be simultaneously administered, wherein both the agents are present in separate formulations. In another alternative, the calcium salt can be administered just followed by the core-shell composition, or vice versa. In the separate administration protocol, the core-shell composition and calcium salt may be administered a few minutes apart, or a few hours apart, or a few days apart.

The term "treating" as used herein includes achieving a therapeutic benefit and/or a prophylactic benefit. By therapeutic benefit is meant eradication, amelioration, or prevention of the underlying disorder being treated. For example, in a hyperphosphatemia patient, therapeutic benefit includes eradication or amelioration of the underlying hyperphosphatemia. Also, a therapeutic benefit is achieved with the eradication, amelioration, or prevention of one or more of the physiological symptoms associated with the underlying disorder such that an improvement is observed in the patient, notwithstanding that the patient may still be afflicted with the underlying disorder. For example, administration of core-shell compositions to a patient suffering from renal insufficiency and/or hyperphosphatemia provides therapeutic benefit not only when the patient's serum phosphate level is decreased, but also when an improvement is observed in the patient with respect to other disorders that accompany renal failure and/or hyperphosphatemia like ectopic calcification and renal osteodistrophy. For prophylactic benefit, the core-shell compositions may be administered to a patient at risk of developing hyperphosphatemia or to a patient reporting one or more of the physiological symptoms of hyperphosphatemia, even though a diagnosis of hyperphosphatemia may not have been made.

The pharmaceutical compositions of the present invention include compositions wherein the core-shell compositions are present in an effective amount, i.e., in an amount effective to achieve therapeutic or prophylactic benefit. The actual amount effective for a particular application will depend on the patient (e.g., age, weight, etc.), the condition being treated, and the route of administration. Determination of an effective amount is well within the capabilities of those skilled in the art, especially in light of the disclosure herein.

The effective amount for use in humans can be determined from animal models. For example, a dose for humans can be formulated to achieve circulating and/or gastrointestinal concentrations that have been found to be effective in animals.

The dosages of the core-shell compositions in animals will depend on the disease being, treated, the route of administration, the physical characteristics of the patient being treated, and the composition of the core and shell components. Dosage levels of the core-shell compositions for therapeutic and/or prophylactic uses can be from about 0.5 gm/day to about 30 gm/day. It is preferred that these polymers are administered along with meals. The compositions may be administered one time a day, two times a day, or three times a day. Most preferred dose is about 15 gm/day or less. A preferred dose range is about 5 gm/day to about 20 gm/day, more preferred is about 5 gm/day to about 15 gm/day, even more preferred is about 10 gm/day to about 20 gm/day, and most preferred is about 10 gm/day to about 15 gm/day.

In some embodiments, the amount of target solute bound and/or retained by the core-shell particles is greater than the amount if the core component is used in the absence of the shell. Hence, the dosage of the core component in some embodiments is lower when used in combination with a shell compared to when the core is used without the shell. Hence, in some embodiments of the core-shell pharmaceutical compositions, the amount of core component present in the core-shell pharmaceutical composition is less than the amount that is administered to an animal in the absence of the shell component.

Preferably, the core-shell compositions used for therapeutic and/or prophylactic benefits can be administered alone or in the form of a pharmaceutical composition. The pharmaceutical compositions comprise of the core-shell compositions, one or more pharmaceutically acceptable carriers, diluents or excipients, and optionally additional therapeutic agents. The compositions can be administered by injection, topically, orally, transdermally, or rectally. Preferably, the core-shell composition or the pharmaceutical composition comprising the core-shell composition is administered orally. The oral form in which the core-shell composition is administered can include powder, tablet, capsule, solution, or emulsion. The therapeutically effective amount can be administered in a single dose or in a series of doses separated by appropriate time intervals, such as hours.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Suitable techniques for preparing pharmaceutical compositions of the core-shell compositions are well known in the art.

In addition to the uses of the core-shell compositions described herein in the gastro-intestinal tract, these compositions can also be used for producing local effects in other parts of the body, for example in topical formulations for local effects on the skin or in systemic formulations for producing local effects in particular organs, like the liver or the heart.

In some embodiments the polymers of the invention are provided as pharmaceutical compositions in the form of chewable tablets. In addition to the active ingredient, the following types of excipients are commonly used: a sweetening agent to provide the necessary palatability, plus a binder where the former is inadequate in providing sufficient tablet hardness; a lubricant to minimize frictional effects at the die wall and facilitate tablet ejection; and, in some formulations a small amount of a disintegrant is added to facilitate mastication. In general excipient levels in currently-available chewable tablets are on the order of 3-5 fold of active ingredient(s) whereas sweetening agents make up the bulk of the inactive ingredients.

The present invention provides chewable tablets that contain a polymer or polymers of the invention and one or more pharmaceutical excipients suitable for formulation of a chewable tablet. The polymer used in chewable tablets of the invention preferably has a swelling ratio while transiting the oral cavity and in the esophagus of less than about 5, preferably less than about 4, more preferably less than about 3, more preferably less than 2.5, and most preferably less than about 2. The tablet comprising the polymer, combined with suitable excipients, provides acceptable organoleptic properties such as mouthfeel, taste, and tooth packing, and at the same time does not pose a risk to obstruct the esophagus after chewing and contact with saliva.

In some aspects of the invention, the polymer(s) provide mechanical and thermal properties that are usually performed by excipients, thus decreasing the amount of such excipients required for the formulation. In some embodiments the active ingredient (e.g., polymer) constitutes over about 30%, more preferably over about 40%, even more preferably over about 50%, and most preferably more than about 60% by weight of the chewable tablet, the remainder comprising suitable excipient(s). In some embodiments the polymer comprises about 0.6 gm to about 2.0 gm of the total weight of the tablet, preferably about 0.8 gm to about 1.6 gm. In some embodiments the polymer comprises more than about 0.8 gm of the tablet, preferably more than about 1.2 gm of the tablet, and most preferably more than about 1.6 gm of the tablet. The polymer is produced to have appropriate strength/friability and particle size to provide the same qualities for which excipients are often used, e.g., proper hardness, good mouth feel, compressibility, and the like. Unswelled particle size for polymers used in chewable tablets of the invention is less than about 80, 70, 60, 50, 40, 30, or 20 microns mean diameter. In preferred embodiments, the unswelled particle size is less than about 80, more preferably less than about 60, and most preferably less than about 40 microns.

Pharmaceutical excipients useful in the chewable tablets of the invention include a binder, such as microcrystalline cellulose, colloidal silica and combinations thereof (Prosolv 90), carbopol, providone and xanthan gum; a flavoring agent, such as sucrose, mannitol, xylitol, maltodextrin, fructose, or sorbitol; a lubricant, such as magnesium stearate, stearic acid, sodium stearyl fumurate and vegetable based fatty acids; and, optionally, a disintegrant, such as croscarmellose sodium, gellan gum, low-substituted hydroxypropyl ether of cellulose, sodium starch glycolate. Other additives may include plasticizers, pigments, talc, and the like. Such additives and other suitable ingredients are well-known in the art; see, e.g., Gennaro A R (ed), *Remington's Pharmaceutical Sciences*, 20th Edition.

In some embodiments the invention provides a pharmaceutical composition formulated as a chewable tablet, comprising a polymer described herein and a suitable excipient. In some embodiments the invention provides a pharmaceutical composition formulated as a chewable tablet, comprising a polymer described herein, a filler, and a lubricant. In some embodiments the invention provides a pharmaceutical composition formulated as a chewable tablet, comprising a polymer described herein, a filler, and a lubricant, wherein the filler is chosen from the group consisting of sucrose, mannitol, xylitol, maltodextrin, fructose, and sorbitol, and wherein the lubricant is a magnesium fatty acid salt, such as magnesium stearate.

The tablet may be of any size and shape compatible with chewability and mouth disintegration, preferably of a cylindrical shape, with a diameter of about 10 mm to about 40 mm and a height of about 2 mm to about 10 mm, most preferably a diameter of about 22 mm and a height of about 6 mm.

In one embodiment, the polymer is pre-formulated with a high Tg/high melting point low molecular weight excipient such as mannitol, sorbose, sucrose in order to form a solid solution wherein the polymer and the excipient are intimately mixed. Method of mixing such as extrusion, spray-drying, chill drying, lyophilization, or wet granulation are useful. Indication of the level of mixing is given by known physical methods such as differential scanning calorimetry or dynamic mechanical analysis.

Methods of making chewable tablets containing pharmaceutical ingredients, including polymers, are known in the art. See, e.g., European Patent Application No. EP373852A2 and U.S. Pat. No. 6,475,510, and Remington's Pharmaceutical Sciences, which are hereby incorporated by reference in their entirety.

In some embodiments the polymers of the invention are provided as pharmaceutical compositions in the form of liquid formulations. In some embodiments the pharmaceutical composition contains an ion-binding polymer dispersed in a suitable liquid excipient. Suitable liquid excipients are known in the art; see, e.g., *Remington's Pharmaceutical Sciences*.

EXAMPLES

Example 1

Synthesis of Core-Shell Crosslinked Polyallylamine Particles

In this process, spherical particles were formed by an inverse suspension procedure wherein a prepolymer (polyallylamine) is crosslinked with epichlorohydrine. A block copolymer was used to impart mechanical stability to the droplets during the crosslinking reaction and provide a shell membrane chemically anchored to the core particle.

General Procedure for Block Copolymers Synthesis

The block copolymers were prepared by RAFT living free radical polymerization method, using a dithiocarbazide compound as a reversible chain transfer agent (CTA) and a diazonitrile free radical initiator (AMVN) indicated below:

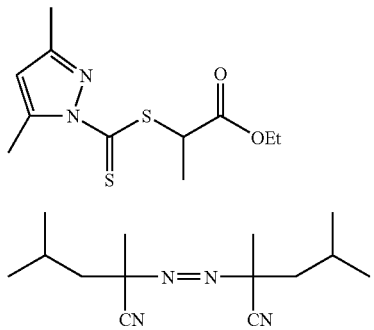

CTA

AMVN

Synthesis of Poly(n-butyl acrylate-co-t-butyl acrylate) First Block n-Butyl acrylate (25 g, 195 mmol) and t-butyl acrylate (25 g, 195 mmol) were combined with the CTA (173:1 Monomer: CTA, 616 mg, 2.26 mmol)) and AIBN (18.6 mg, 0.113 mmol). The monomer to CTA ratio is fixed so that the theoretical number average molecular weight (Mn) is 20,000 g.mol at 90% conversion. The solution was stirred while purging with Ar for 20 minutes at room temperature. After this time, it was heated to 65° C. under Ar while stirring for 3 hours and then cooled to room temperature. $^1$H NMR in CDCl$_3$ showed 87% conversion based on disappearance of monomer. The crude polymer was dissolved in 50 ml of acetone and precipitated into 900 ml of a 9:1 (v/v) methanol: water solution. After several hours, the polymeric oil had separated to the bottom and the top layer was discarded. The polymeric oil was dried in vacuum to yield 44 g (88% yield) of extremely thick yellow oil. $^1$H NMR (300 MHz, CDCl$_3$): δ=4.15-3.95 (2H, bm), 2.45-2.05 (2H, bm). 1.95-1.75 (1H, bm), 1.60-1.5 (5H, bm), 1.5-1.3 (I 1H, bm), 0.93 (3H, t). GPC (THF, polystyrene standards): Mn=25900; PDI=1.13. GPC (DMF, polyethyleneglycol standards): Mn=6600; PDI=1.58.

Following this procedure, 4 different first blocks were prepared, which are listed in TABLE 3 as Example 1-1 to 1-4.

TABLE 3

| Example | Identification | Composition | Molecular weight (g/mol) |
|---|---|---|---|
| 1-1 | nBA1tBA1_20k | n-butyl acrylate-co-t-butyl acrylate 50/50 mol-% | 20,000 |
| 1-2 | nDiBA1tBA1_20k | N,N-di-n-butyl acrylamide-co-t-butyl acrylate 50/50 mol-% | 20,000 |
| 1-3 | nBA1tBA1_50k | n-butyl acrylate-co-t-butyl acrylate 50/50 mol-% | 50,000 |
| 1-4 | nDiBA1tBA1_50k | N,N-di-n-butyl acrylamide-co-t-butyl acrylate 50/50 mol-% | 50,000 |

Synthesis of Poly[(n-butyl acrylate-co-t-butyl acrylate)-b-(N,N-dimethylacrylamide-co-glycidyl methacrylate)]

Theoretical Mn=20,000 $1^{st}$ block and Mn=5000 $2^{nd}$ block at 80% con. A solution of poly(n-butyl acrylate-co-t-butyl acrylate) terminated with the CTA (2.53 ml, 40 wt % in DMF) and a solution of AMVN (48.1 µl, 0.00736 mmol, 4 wt % in DMF) were combined manually. The mixture was then purged with Ar for 20 minutes. While stirring at room temperature, N,N-dimethylacrylamide (27.5 µl, 0.267 mmol) and a solution of glycidyl methacrylate (14.3 µl, 0.0296 mmol, 30 wt % in DMF) were added. The solution temperature was then raised to 55° C. over 30 minutes while stirring. At this time, N,N-dimethylacrylamide (10.3 µl, 0.100 mmol) and a solution of glycidyl methacrylate (5.4 µl, 0.0111 mmol, 30 wt % in DMF) were added via a robot. Every 10 minutes for the next 4 hours N,N-dimethylacrylamide (10.3 µl, 0.100 mmol) and a solution of glycidyl methacrylate (5.4 µl, 0.0111 mmol, 30 wt % in DMF) were added while the solution stirred under Ar at 55° C. After all additions had been completed, the solution was stirred for an additional 2 hours under Ar at 55° C. and then cooled to room temperature. The crude polymer was dissolved in 2 ml acetone and precipitated into 30 ml water. The resulting mixture was centrifuged at 1000 rpm for 60 minutes and the upper water layer then removed. The polymeric powder was washed with an additional 10 ml of water, centrifuged, and the water layer removed. The resulting wet powder was dried under vacuum at 30° C. to give a viscous liquid. Subsequent lyophilization provided 1.19 g (92% yield) of a sticky solid. GPC (DMF, polyethyleneglycol standards): Mn=8500; PDI=2.10.

Similar procedures were used to make block copolymers of various length and chemical compositions which are reported in the following tables, TABLES 4 and 5.

TABLE 4

| Library: Plate1 (ID: 100436) Unit: mg | | | | | | | | |
|---|---|---|---|---|---|---|---|---|
| Row | Col | nDiBA1tBA1 20k | nDiBA1tBA1 50k | DMF | THF | AMVN | GMA | DMA |
| A | 1 | 1065.7 | 0.0 | 754.2 | 707.3 | 2.0 | 45.8 | 287.3 |
| A | 2 | 915.9 | 0.0 | 709.1 | 665.0 | 1.7 | 78.7 | 493.8 |
| A | 3 | 714.9 | 0.0 | 648.6 | 608.2 | 1.3 | 122.8 | 770.8 |
| A | 4 | 1065.7 | 0.0 | 754.2 | 707.3 | 2.0 | 45.8 | 287.3 |
| A | 5 | 915.9 | 0.0 | 709.1 | 665.0 | 1.7 | 78.7 | 493.8 |
| A | 6 | 714.9 | 0.0 | 648.6 | 608.2 | 1.3 | 122.8 | 770.8 |
| B | 1 | 982.0 | 0.0 | 810.5 | 760.1 | 1.8 | 116.8 | 190.1 |
| B | 2 | 798.9 | 0.0 | 806.5 | 756.3 | 1.5 | 190.1 | 309.2 |
| B | 3 | 581.8 | 0.0 | 801.7 | 751.8 | 1.1 | 276.8 | 450.4 |
| B | 4 | 982.0 | 0.0 | 810.5 | 760.1 | 1.8 | 116.8 | 190.1 |
| B | 5 | 798.9 | 0.0 | 806.5 | 756.3 | 1.5 | 190.1 | 309.2 |
| B | 6 | 581.8 | 0.0 | 801.7 | 751.8 | 1.1 | 276.8 | 450.4 |
| C | 1 | 0.0 | 897.8 | 622.9 | 584.1 | 0.7 | 38.6 | 242.0 |
| C | 2 | 0.0 | 770.4 | 585.8 | 549.3 | 0.6 | 66.2 | 415.3 |
| C | 3 | 0.0 | 600.1 | 536.1 | 502.7 | 0.4 | 103.1 | 647.0 |

TABLE 4-continued

| | | | | | | | | |
|---|---|---|---|---|---|---|---|---|
| C | 4 | 0.0 | 897.8 | 622.9 | 584.1 | 0.7 | 38.6 | 242.0 |
| C | 5 | 0.0 | 770.4 | 585.8 | 549.3 | 0.6 | 66.2 | 415.3 |
| C | 6 | 0.0 | 600.1 | 536.1 | 502.7 | 0.4 | 103.1 | 647.0 |
| D | 1 | 0.0 | 826.5 | 670.8 | 629.0 | 0.6 | 98.3 | 160.0 |
| D | 2 | 0.0 | 671.1 | 668.2 | 626.7 | 0.5 | 159.7 | 259.8 |
| D | 3 | 0.0 | 487.7 | 665.3 | 623.9 | 0.4 | 232.1 | 377.6 |
| D | 4 | 0.0 | 826.5 | 670.8 | 629.0 | 0.6 | 98.3 | 160.0 |
| D | 5 | 0.0 | 671.1 | 668.2 | 626.7 | 0.5 | 159.7 | 259.8 |
| D | 6 | 0.0 | 487.7 | 665.3 | 623.9 | 0.4 | 232.1 | 377.6 |

General Design and Variations from Example(mol:mol ratios)
Starting Block (45.5 wt % solns): Rows A, B = 20 k 1:1 N,N-di-n-Butyl Acrylamide:t-Butyl Acylate
Rows C, D = 50 k 1:1 N,N-di-n-Butyl Acrylamide:t-Butyl Acylate
Initiator: AMVN
Temperature: 60 C.
2nd Block Compostion: Rows A, C = 1:9 GMA:DMA
Rows B, D = 3:7 GMA:DMA
Block Target Mn: A1, B1, A4, B4 = 5k
A2, B2, A5, B5 = 10k
A3, B3, A6, B6 = 20k
C1, D1, C4, D4 = 12.5k
C2, D2, C5, D5 = 25k
C3, D3, C6, D6 = 50k
2nd Block Method: Columns 1, 2, 3 = Batch Addition
Columns 4, 5, 6 = Spot Addition

TABLE 5

Library: Plate1 (ID: 100369) Unit: mg

| Row | Col | GMA | DMF | nBA1tBA1 20k | DMA | AIBN |
|---|---|---|---|---|---|---|
| A | 1 | 39.8 | 1566.0 | 963.2 | 249.2 | 1.2 |
| A | 2 | 72.5 | 1458.0 | 842.7 | 454.2 | 1.0 |
| A | 3 | 116.8 | 1311.6 | 679.3 | 732.2 | 0.8 |
| A | 4 | 39.8 | 1566.0 | 963.2 | 249.2 | 1.2 |
| A | 5 | 72.5 | 1458.0 | 842.7 | 454.2 | 1.0 |
| A | 6 | 116.8 | 1311.6 | 679.3 | 732.2 | 0.8 |
| B | 1 | 74.2 | 1604.6 | 935.9 | 206.6 | 1.2 |
| B | 2 | 132.1 | 1532.2 | 800.2 | 368.0 | 1.0 |
| B | 3 | 206.6 | 1439.1 | 625.7 | 575.5 | 0.8 |
| B | 4 | 74.2 | 1604.6 | 935.9 | 206.6 | 1.2 |
| B | 5 | 132.1 | 1532.2 | 800.2 | 368.0 | 1.0 |
| B | 6 | 206.6 | 1439.1 | 625.7 | 575.5 | 0.8 |

General Design (mol:mol ratios)
Starting Block: 20 k 1:1 n-Butyl Acrylate:t-Butyl Acylate
Initiator: AIBN
Temperature: 65 C.
2nd Block Compostion: Row A = 1:9 GMA:DMA
Row B = 2:8 GMA:DMA
2nd Block Target Mn: Columns 1, 4 = 5k
Columns 2, 5 = 10k
Columns 3, 6 = 20k
2nd Block Method: Columns 1, 2, 3 = Batch Addition
Columns 4, 5, 6 = Spot Addition General Procedure for the Synthesis of Core/Shell Crosslinked Polyallylamine Particles:

Preparation of polyallylamine (PAA) solution: Polyallylamine hydrochloride (Mw 15,000) was dissolved in water, and NaOH was added to neutralize 25 mol % of hydrochloride. The concentration of polyallyamine hydrochloride in solution was 33 wt. %.

Preparation of diblock copolymer solution: diblock copolymer was dissolved in toluene at 5 wt. %.

Preparation of core/shell particles: To 15 ml glass reactor was charged PAA solution, diblock copolymer solution, and toluene, and some typical solution compositions as shown in Tables 4-9. The mixture was emulsified with an Ultra-Turrax for 30 seconds and a magnetic stir bar was put into the suspension. The suspension was stirred and heated at 60° C. for 30 minutes and epichlorohydrin (10 mol % based on amine groups) was added. The suspension was further stirred at 60° C. for 8 hours and then cooled to room temperature.

Purification of core/shell particles: To the reaction mixture above, methanol (10 mL) was added and white particles precipitated out. The mixture was shaken for 30 minutes and centrifuged. The white particles separated from supernatant solution and collected. The white particles were further washed with methanol (10 mL×2) and water (10 mL×3) by repeating the same shake/centrifuge procedure. Finally the particles were freeze-dried for three days.

Example 2

Synthesis of 1,3-Diaminopropane/Epichlorohydrin Crosslinked Beads (Referred to Herein as: Bead-Pi-4-s)

The reaction vessel used was a 3-liter, three necked round bottom flask with four side baffles, equipped with an oil heating bath, cold-water reflux condenser, and mechanical stirrer with a 3 inch propeller. To this reaction vessel is introduced a solution of 1,3-diaminopropane (90.2 g, 1.21 mole) dissolved in 90.2 g of water, surfactant (branched dodecylbenzene sulfonic acid sodium salt, 6.4 g dissolved in 100 g of water), and 1 Kg of toluene. This initial charge is agitated to 600 rpm for 2 minutes and then lowered to 300 rpm for 10 minutes before the first addition of epichlorohydrin. This speed is maintained through out the experiment. The solution was heated to 80° C. and maintained at this temperature throughout the experiment.

Into a separate vessel, a 40 mass % solution of epichlorohydrin in toluene was prepared. Using a syringe pump, 1.2 equivalents of epichlorohydrin (134.7 g, (1.45 mole)) was added over a 3 hour period. The reaction was continued for an additional 2 hours before adding 0.75 equivalents of sodium hydroxide (36.5 g (0.91 mole)) in a 40 weight % solution. The sodium hydroxide solution was added to the reaction via a syringe pump over a 2.5-hour period. The reaction was maintained at 80° C. for a further 8 hours. The beads were purified by removing the toluene, washing with 1000 ml of acetone, followed by methanol, and then a 20% solution of NaOH (to remove the surfactant), and twice more with deionized water. The beads were freeze dried for 3 days to give a fine white powder weighing at 160 g (92% yield), and having a mean diameter of 93 μm.

Synthesis of 1,3-Diaminopropane/Epichlorohydrin Crosslinked Beads (Referred to Herein as: Bead-Pi-3-s)

The procedure described above was used with 1 equivalent of epichlorohydrin.

Synthesis of Water Swollen Crosslinked Beads Prepared with 1,3-Diaminopropane/Epichlorohydrin in the Presence of Surfactant (Referred to Herein as: Bead-Pi-5-s)

The procedure described above for the preparation of beads from 1,3-diaminopropane/epichlorohydrin was reproduced exactly up to stage 2. After the reaction flask had cooled to room temperature, the stirring was stopped. The beads settle to the bottom of the flask. The clear toluene layer was decanted from the reaction and replaced by fresh toluene to remove unreacted epichlorohydrin. This procedure was repeated 4 times and washing with a total of 3000 ml of toluene. Through out this process the beads were not allowed to dry out. The total weight of the solution was made to 756 g by adding toluene to give a 21 wt-% solution of bead suspended in toluene.

Example 3

Preparation of Ethyl Cellulose Shell/1,3 Di-Amino Propane Epichlorohydrine Crosslinked Core Particle The beads obtained from Example 2 are spray-coated with an ethyl cellulose polymer shell using a Wurster fluid bed coater 2"-4"/6" Portable Unit. The fluidized bed unit is operated so that an average 5 microns thick coating is deposited on the core particles, using a 30 wt-% solid aqueous emulsion (AQUACOAT® ECD, FMC corp.).

Example 4

Binding Capacity in a Digestion Mimic

This procedure was used to mimic the conditions of use of a phosphate binder drug and measure the binding characteristics of the polymer for phosphate (target solute) in the presence of other metabolites (competing solutes). A liquid meal was prepared and the meal was artificially digested in the presence of pepsin and pancreatic juice. The sequence of addition of enzymes and the pH profile were controlled so that the digestion process was simulated down to the jejunum level. An aliquot of the digested meal mimic is centrifuged and the supernatant assayed for phosphate.

An aliquot of dried resin of weight P(gr), was mixed under gentle agitation with a fixed volume, V(ml), of a meal digest solution with a phosphate ion concentration of $C_{start}$(mM). After resin equilibration, the solution was decanted by centrifugation and the supernatant analyzed for residual phosphate concentration by ionic chromatography, $C_{eq}$(mM). The binding capacity was calculated as BC (mmol/gr)=V. $(C_{start}-C_{eq})$/P.

A. Core/Shell Crosslinked Polyallylamine Particles

Procedures described in Example 1 were implemented in a library format of 4×6 reactors, where the nature of the block copolymer was varied from well to well, as indicated in Tables 6-9. Entries correspond to the weight of chemicals used in each reaction well and to the phosphate binding capacity measured in the meal digest fluid. A Selectivity Index (SI) was computed to measure the phosphate binding relative to the core material (i.e. crosslinked polyallylamine, Renagel). When SI was greater than 1, the core-shell material bound more phosphate than the corresponding core polymer on a weight basis. The SI values for the polymers are included in Tables 6-9.

Results are shown in Tables 6-9. Results collated in this series of examples show that the core-shell particles of the invention display higher binding for phosphate over bare, non-encapsulated particles in simulated fluid representative of the real conditions of use. Some of the best performing core-shell materials are then assessed in binding phosphate in the ex-vivo aspirates from human intestinal content.

TABLE 6

Library 100411
Library: Plate1 Unit: ul

| Row | Col | toluene | di-block s | PAA s | ECH | di-block | Pstart (mM) | Peq (mM) | BC (mmol/gr) | SI(—) |
|---|---|---|---|---|---|---|---|---|---|---|
| 1 | 1 | 281 | 1860 | 750 | 22.6 | 369_A1 | 7.6 | 2.98 | 1.85 | 1.09 |
| 1 | 2 | 281 | 1860 | 750 | 22.6 | 369_A2 | 7.6 | 2.41 | 2.08 | 1.22 |
| 1 | 3 | 281 | 1860 | 750 | 22.6 | 369_A4 | 7.6 | 2.99 | 1.84 | 1.08 |
| 1 | 4 | 281 | 1860 | 750 | 22.6 | 369_A5 | 7.6 | 2.85 | 1.90 | 1.12 |
| 2 | 1 | 281 | 1860 | 750 | 22.6 | 369_B1 | 7.6 | 3.15 | 1.78 | 1.05 |
| 2 | 2 | 281 | 1860 | 750 | 22.6 | 369_B2 | 7.6 | 2.35 | 2.10 | 1.23 |
| 2 | 3 | 281 | 1860 | 750 | 22.6 | 369_B4 | 7.6 | 2.76 | 1.94 | 1.14 |
| 2 | 4 | 281 | 1860 | 750 | 22.6 | 369_B5 | 7.6 | 2.86 | 1.90 | 1.12 |
| Polyallylamine core | | | | | | | 7.6 | 3.35 | 1.70 | 1.00 |

Diblock is dispensed as a 5 wt-% solution in toluene

TABLE 7

Library: Plate1 (ID: 100482) Unit: mg
Block copolymers

| Row | Col | 436 B4 | 436 B5 | 436 B6 | 436 D4 | 436 D5 | 436 D6 | Pstart m (M) | Peq (mM) | BC (mmol/gr) | SI (—) |
|---|---|---|---|---|---|---|---|---|---|---|---|
| 1 | 1 | 81.00 | 0.00 | 0.00 | 0.00 | 0.00 | 0.00 | | | | |
| 1 | 2 | 0.00 | 81.00 | 0.00 | 0.00 | 0.00 | 0.00 | 13.41 | 6.32 | 2.84 | 1.02 |
| 1 | 3 | 0.00 | 0.00 | 81.00 | 0.00 | 0.00 | 0.00 | 13.41 | 6.05 | 2.94 | 1.06 |
| 1 | 4 | 0.00 | 0.00 | 0.00 | 81.00 | 0.00 | 0.00 | 13.41 | 5.53 | 3.16 | 1.14 |

TABLE 7-continued

| | | | | | | | | | | |
|---|---|---|---|---|---|---|---|---|---|---|
| 1 | 5 | 0.00 | 0.00 | 0.00 | 0.00 | 81.00 | 0.00 | 13.41 | 6.33 | 2.83 | 1.02 |
| 1 | 6 | 0.00 | 0.00 | 0.00 | 0.00 | 0.00 | 81.00 | 13.41 | 4.57 | 3.54 | 1.28 |
| 2 | 1 | 40.50 | 0.00 | 0.00 | 0.00 | 0.00 | 0.00 | 13.41 | 6.66 | 2.70 | 0.97 |
| 2 | 2 | 0.00 | 40.50 | 0.00 | 0.00 | 0.00 | 0.00 | 13.41 | 5.55 | 3.15 | 1.13 |
| 2 | 3 | 0.00 | 0.00 | 40.50 | 0.00 | 0.00 | 0.00 | 13.41 | 5.36 | 3.22 | 1.16 |
| 2 | 4 | 0.00 | 0.00 | 0.00 | 40.50 | 0.00 | 0.00 | 13.41 | 4.98 | 3.37 | 1.22 |
| 2 | 5 | 0.00 | 0.00 | 0.00 | 0.00 | 40.50 | 0.00 | 13.41 | 4.82 | 3.44 | 1.24 |
| 2 | 6 | 0.00 | 0.00 | 0.00 | 0.00 | 0.00 | 40.50 | 13.41 | 3.96 | 3.78 | 1.36 |
| 3 | 1 | 81.00 | 0.00 | 0.00 | 0.00 | 0.00 | 0.00 | 13.41 | 5.70 | 3.08 | 1.11 |
| 3 | 2 | 0.00 | 81.00 | 0.00 | 0.00 | 0.00 | 0.00 | 13.41 | 7.09 | 2.53 | 0.91 |
| 3 | 3 | 0.00 | 0.00 | 81.00 | 0.00 | 0.00 | 0.00 | 13.41 | 5.72 | 3.08 | 1.11 |
| 3 | 4 | 0.00 | 0.00 | 0.00 | 81.00 | 0.00 | 0.00 | 13.41 | 6.57 | 2.74 | 0.99 |
| 3 | 5 | 0.00 | 0.00 | 0.00 | 0.00 | 81.00 | 0.00 | 13.41 | 6.40 | 2.80 | 1.01 |
| 3 | 6 | 0.00 | 0.00 | 0.00 | 0.00 | 0.00 | 81.00 | 13.41 | 6.54 | 2.75 | 0.99 |
| 4 | 1 | 40.50 | 0.00 | 0.00 | 0.00 | 0.00 | 0.00 | 13.41 | 5.36 | 3.22 | 1.16 |
| 4 | 2 | 0.00 | 40.50 | 0.00 | 0.00 | 0.00 | 0.00 | 13.41 | 6.07 | 2.94 | 1.06 |
| 4 | 3 | 0.00 | 0.00 | 40.50 | 0.00 | 0.00 | 0.00 | 13.41 | 5.51 | 3.16 | 1.14 |
| 4 | 4 | 0.00 | 0.00 | 0.00 | 40.50 | 0.00 | 0.00 | 13.41 | 4.21 | 3.68 | 1.33 |
| 4 | 5 | 0.00 | 0.00 | 0.00 | 0.00 | 40.50 | 0.00 | 13.41 | 4.96 | 3.38 | 1.22 |
| 4 | 6 | 0.00 | 0.00 | 0.00 | 0.00 | 0.00 | 40.50 | 13.41 | 4.58 | 3.53 | 1.27 |
| Polyallylamine core | | | | | | | | 13.41 | 6.48 | 2.77 | 1.00 |

Constant reactor composition (mg)

| toluene | PAA | H2O | NaOH | EPH |
|---|---|---|---|---|
| 1768.95 | 270.00 | 511.16 | 28.84 | 40.05 |

Row 1 & 2: 30 sec. sonication time
Row 3 & 4: 90 sec. sonication time

TABLE 8

| Library | Sample | Block Copolymer | BC (mmol/gr) | IC (—) |
|---|---|---|---|---|
| 100516 | 100516 A1 | 100436 A1 | 3.02 | 1.25 |
| 100516 | 100516 A2 | 100436 A2 | 3.44 | 1.43 |
| 100516 | 100516 A3 | 100436 A3 | 3.33 | 1.38 |
| 100516 | 100516 A4 | 100436 A4 | 3.01 | 1.25 |
| 100516 | 100516 A5 | 100436 A5 | 3.29 | 1.37 |
| 100516 | 100516 A6 | 100436 A6 | 3.52 | 1.46 |
| 100516 | 100516 B1 | 100436 B1 | 3.30 | 1.37 |
| 100516 | 100516 B2 | 100436 B2 | 3.60 | 1.49 |
| 100516 | 100516 B3 | 100436 B3 | 3.38 | 1.40 |
| 100516 | 100516 B4 | 100436 B4 | 3.52 | 1.46 |
| 100516 | 100516 B5 | 100436 B5 | 3.74 | 1.55 |
| 100516 | 100516 B6 | 100436 B6 | 3.32 | 1.38 |
| 100516 | 100516 C1 | 100436 C1 | 3.89 | 1.61 |
| 100516 | 100516 C2 | 100436 C2 | 3.54 | 1.47 |
| 100516 | 100516 C3 | 100436 C3 | 2.75 | 1.14 |
| 100516 | 100516 C4 | 100436 C4 | 3.57 | 1.48 |
| 100516 | 100516 C5 | 100436 C5 | 3.53 | 1.47 |
| 100516 | 100516 C6 | 100436 C6 | 2.64 | 1.09 |
| 100516 | 100516 D1 | 100436 D1 | 3.78 | 1.57 |
| 100516 | 100516 D2 | 100436 D2 | 3.57 | 1.48 |
| 100516 | 100516 D3 | 100436 D3 | 3.12 | 1.29 |
| 100516 | 100516 D4 | 100436 D4 | 3.40 | 1.41 |
| 100516 | 100516 D5 | 100436 D5 | 3.75 | 1.55 |
| Polyallylamine core | | | 2.41 | 1.00 |

Constant reactor composition (mg)

| toluene | PAA | H₂O | NaOH | EPH | Block cop. |
|---|---|---|---|---|---|
| 1768.95 | 270.00 | 511.16 | 28.84 | 40.05 | 40.05 |

30 sec. sonication time
Library 100517 is identical to 100516 with the exception that the beads were further treated with HCl 1M for 6 hrs @60° C. to deprotect the terbutylacrylate groups into acrylic acid groups.

TABLE 9

| Library | Sample | Block Copolymer | BC (mmol/gr) | IC (—) |
|---|---|---|---|---|
| 100517 | 100517 A1 | 100436 A1 | 3.04 | 1.26 |
| 100517 | 100517 A2 | 100436 A2 | 3.30 | 1.37 |
| 100517 | 100517 A3 | 100436 A3 | 3.26 | 1.35 |
| 100517 | 100517 A4 | 100436 A4 | 3.35 | 1.39 |
| 100517 | 100517 A5 | 100436 A5 | 2.86 | 1.18 |
| 100517 | 100517 B1 | 100436 B1 | 3.22 | 1.33 |
| 100517 | 100517 B2 | 100436 B2 | 3.60 | 1.49 |
| 100517 | 100517 B3 | 100436 B3 | 3.64 | 1.51 |
| 100517 | 100517 B4 | 100436 B4 | 3.58 | 1.48 |
| 100517 | 100517 B5 | 100436 B5 | 3.82 | 1.58 |
| 100517 | 100517 B6 | 100436 B6 | 3.62 | 1.50 |
| 100517 | 100517 C1 | 100436 C1 | 3.52 | 1.46 |
| 100517 | 100517 C2 | 100436 C2 | 3.37 | 1.39 |
| 100517 | 100517 C3 | 100436 C3 | 2.86 | 1.18 |
| 100517 | 100517 C4 | 100436 C4 | 3.24 | 1.34 |
| 100517 | 100517 C5 | 100436 C5 | 3.34 | 1.38 |
| 100517 | 100517 C6 | 100436 C6 | 2.22 | 0.92 |
| 100517 | 100517 D1 | 100436 D1 | 3.24 | 1.34 |
| 100517 | 100517 D2 | 100436 D2 | 3.17 | 1.31 |
| 100517 | 100517 D3 | 100436 D3 | 3.21 | 1.33 |
| 100517 | 100517 D4 | 100436 D4 | 3.32 | 1.38 |
| 100517 | 100517 D5 | 100436 D5 | 3.02 | 1.25 |
| Polyallylamine core | | | 2.42 | 1.00 |

Constant reactor composition (mg)

| toluene | PAA | H₂O | NaOH | EPH | Block cop. |
|---|---|---|---|---|---|
| 1768.95 | 270.00 | 511.16 | 28.84 | 40.05 | 40.05 |

30 sec. sonication time
Library 100517 is identical to 100516 with the exception that the beads were further treated with HCl 1M for 6 hrs @60° C. to deprotect the terbutylacrylate groups into acrylic acid groups.

B. Core/Shell Crosslinked 1,3-Diaminopropane/Epichlorohydrine Particles

Procedures described in Example 2 were implemented in a library format of 4×6 reactors, where the nature of the polymer was varied from well to well, as indicated in Tables 1'-18. Entries in the Tables correspond to the weight of chemicals used in each reaction well, and to the phosphate binding capacity measured in the meal digest fluid. A Selectivity Index (SI) was computed as described above. The SI values for the polymers are included in Tables 11-18.

Each example comprised a library of 22 core-shell materials and one core material taken as a reference. The core materials are beads prepared from crosslinked 1,3-diaminopropane/epichlorohydrine as shown in Example 2 (bead 4-s, bead 3-s, and bead 5-s). They were used either as a dry powder (bead 4-s, bead 3-s) or as a slurry in toluene (bead 5-s). The core-shell particles were prepared in semi-continuous reactors arranged in a 4×6 library format. Each reactor had a 3 ml volume, was magnetically stirred, and temperature-controlled. In a typical procedure, the beads were first dispensed, followed by the addition of the selected solvent under magnetic agitation. The reaction temperature was set to 60° C. The shell materials were then robotically dispensed for 4 hours and the 24 reactions kept another 12 hours at the set temperature. The library was then cooled down to ambient temperature and the content of the reactors transferred to 15 ml vials. The core-shell beads were then washed repeatedly with a fresh volume of the same solvent used during the shell coupling reaction, then with isopropanol, and finally with de-ionized water. The particles were finally lyophilized.

The chemical structures of the shell materials used are shown in Table 10.

TABLE 10

| Label | Name | CAS # | Structure | MW (g/mol) |
|---|---|---|---|---|
| Shell-AH-1 | POLY(METHYLVINYL ETHER-ALT-MALEIC ANHYDRIDE) | | (structure) | MW ~ 20,000 |
| Shell-AH-2 | POLY(METHYLVINYL ETHER-ALT-MALEIC ANHYDRIDE) | | (structure) | MW ~ 50,000 |
| Shell-AH-3 | POLY(METHYLVINYL ETHER-ALT-MALEIC ANHYDRIDE) | 9011-16-9 | (structure) | Mn. ~ 80,000<br>Mw. ~ 216,000 |
| Shell-AH-4 | POLY(STYRENE-MALEIC ANHYDRIDE) 50:50 (molar) | | | MW = 1600 |
| Shell-AH-5 | POLY(STYRENE-MALEIC ANHYDRIDE) 75:25 (molar) | | | MW = 1900 |
| Shell-AH-6 | POLY(STYRENE-co-MALEIC ANHYDRIDE), CUMENE TERMINATED | 26762-29-8 | | Mn = 1600 |
| Shell-AH-7 | POLY(STYRENE-co-MALEIC ANHYDRIDE), CUMENE TERMINATED | 26762-29-8 | | Mn = 1700 |
| Shell-AH-8 | POLY(STYRENE-co-MALEIC ANHYDRIDE), PARTIAL ISOCTYL ESTER, CUMENE TERMINATED | 160611-46-1 | | Mn = 2300<br>FW = 658.8 |
| Shell-AH-9 | POLY(STYRENE-co-MALEIC ANHYDRIDE), PARTIAL 2-BUTOXYETHYLESTER, CUMENE TERMINATED | 160611-50-7 | | Av. Mn = 2500 |
| Shell-AH-10 | POLY(ETHYLENE-co-ETHYL ACRYLATE-co-MALEIC ANHYDRIDE) | 41171-14-6 | | / |
| Shell-AH-11 | POLY(STYRENE-co-MALEIC ANHYDRIDE), PARTIAL PROPYL ESTER, CUMENE TERMINATED | 160611-48-3 | | Mn ~ 1900 |
| Shell-AH-12 | POLYETHYLENE-graft-MALEIC ANHYDRIDE | 106343-08-2 | | FW ~ 154.2 |
| Shell-AH-13 | POLYISOPRENE-graft-MALEIC ANHYDRIDE | 139948-75-7 | | FW = 234.3<br>Mn ~ 25000 |
| Shell-AH-14 | POLY(ETHYLENE-co- | 64652-60-4 | | FW = 268.3 |

TABLE 10-continued

| Label | Name | CAS # | Structure | MW (g/mol) |
|---|---|---|---|---|
| | BUTYL ACRYLATE-co-MALEIC ANHYDRIDE) | | | |
| Shell-Cl-1 | 2-CHLOROETHANE-SULFONIC ACID SODIUM SALT | 15484-44-3 | 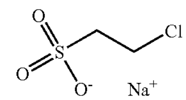 | 166.56 |
| Shell-Cl-2 | 3-CHLORO-2-HYDROXYPROPANE-SULFONIC ACID SODIUM SALT | 126-83-0 | 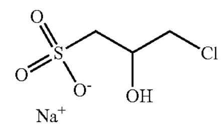 | 196.59 |
| Shell-Mc-1 | DIETHYLENE GLYCOL DIACRYLATE | 4074-88-8 | 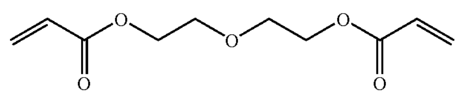 | 214.22 |
| Shell-Mc-2 | POLY(ETHYLENE GLYCOL) DIACRYLATE | 26570-49-8 | 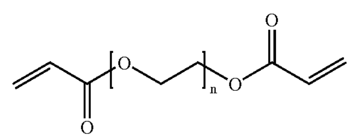 | Mn. ~ 700 |
| Shell-Mc-3 | POLY(ETHYLENE-co-METHACRYLATE-co-GLYCIDYL METHACRYLATE) | 51541-08-3 | | FW = 256.3 |
| Shell-EP-1 | 2-(3,4-EPOXYCYCLOHEXYL)-ETHYL-TRIETHOXYSILANE | | 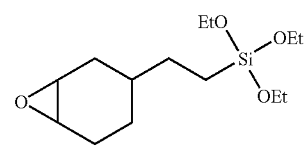 [SMILES: CCO[Si](CCC1CCC2OC2C1)(OCC)OCC] | 288.5 |
| Shell-EP-2 | POLY(ETHYL GLYCOL) DIGLYCIDYL ETHER | 26403-72-5 | 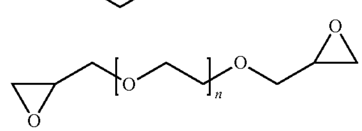 | 526.6 |
| Shell-EP-3 | POLY(ETHYL GLYCOL) (200) DIGLYCIDYL ETHER | 26403-72-5 | | 200 |
| Shell-EP-4 | POLY(ETHYL GLYCOL) (400) DIGLYCIDYL ETHER | 26403-72-5 | | 400 |
| Shell-EP-5 | POLY(ETHYL GLYCOL) (600) DIGLYCIDYL ETHER | 26403-72-5 | | 600 |
| Shell-EP-6 | POLY(ETHYL GLYCOL) (1000) DIGLYCIDYL ETHER | 26403-72-5 | | 1000 |
| Shell-EP-7 | 1,3-BUTADIENE DIEPOXIDE | 1464-53-5 | 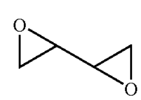 | 86.09 |
| Shell-EP-8 | 3-(1H,1H,7H-DODECAFLUORO-HEPTYLOXY)-1,2-EPOXYPROPANE | 799-34-8 | 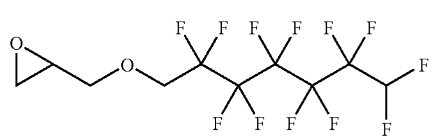 [SMILES: FC(F)C(F)(F)C(F)(F)C(F)(F)C(F)(F)C(F)(F)COCC1CO1] | 388.15 |
| Shell-EP-9 | GLYCIDYL 4-NONYLPHENYL ETHER | 6178-32-1 | 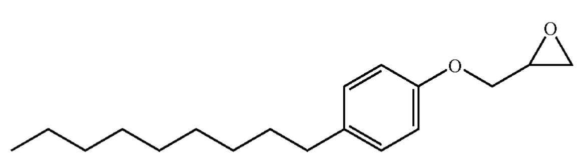 [SMILES: CCCCCCCCCc1ccc(OCC2CO2)cc1] | 276.42 |

TABLE 10-continued

| Label | Name | CAS # | Structure | MW (g/mol) |
|---|---|---|---|---|
| Shell-EP-10 | POLY(PROPYLENE GLYCOL) DIGLYCIDYL ETHER | 26142-30-3 | 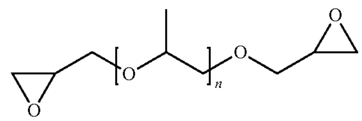 | 640 |
| Shell-EP-11 | GLYCIDYL HEXADECYL ETHER | 15965-99-8 | 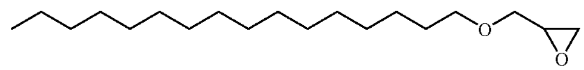 [SMILES: CCCCCCCCCCCCCCCCOCC1CO1] | 298.51 |
| Shell-EP-12bis | 2-[(4-NITROPHENOXY)METHYL] OXIRANE | 5255-75-4 | 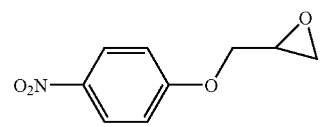 | 195.18 |
| Shell-EP-12 | POLY(BISPHENOL A-co-EPICHLOROHYDRIN), GLYCICYL END-CAPPED | 25036-25-3 | | FW = 487.0 Mn ~ 355 |
| Shell-EP-13 | POLY(BISPHENOL A-co-EPICHLOROHYDRIN), GLYCICYL END-CAPPED | | | FW = 487.0 Mn ~ 1075 |
| Shell-EP-14 | POLY(BISPHENOL A-co-EPICHLOROHYDRIN), GLYCICYL END-CAPPED | | | Mn ~ 1750 |
| Shell-EP-15 | POLY(BISPHENOL A-co-EPICHLOROHYDRIN), GLYCICYL END-CAPPED | | | / |
| Shell-EP-16 | POLY(o-CRESYL GLYCIDYL ETHER)-co-FORMALDEHYDE) | 29690-82-2 | | FW = 194.2 Mn ~ 540 |
| Shell-EP-17 | POLY(o-CRESYL GLYCIDYL ETHER)-co-FORMALDEHYDE) | 29690-82-3 | | FW = 194.2 Mn ~ 1270 |
| Shell-EP-18 | POLY(ETHYLENE-co-GLYCIDYL METHACRYLATE) | 26061-90-5 | | FW = 170.2 |
| Shell-EP-19 | BISPHENOL DIGLYCIDYL ETHER | 1675-54-3 | | |
| Shell-EP-20 | POLY(DIMETHYLSILOXANE) DIGLYCIDYL TERMINATED | 130167-23-6 | | FW = 282.5 EW ~ 490 |
| Shell-EP-21 | POLY[(PHENYL GLYCIDYL ETHER)-co-FORMALDEHYDE] | / | | FW = 180.2 Mn ~ 345 |
| Shell-EP-22 | POLY[(PHENYL GLYCIDYL ETHER)-co-FORMALDEHYDE] | 28064-14-4 | | FW = 180.2 Mn ~ 570 |
| Shell-EP-23 | POLY[(PHENYL GLYCIDYL ETHER)-co-DICYCLOPENTADIENE] | 119345-05-0 | | FW = 286.4 Mn ~ 490 |
| Shell-EP-24 | POLY(EPICHLOROHYDRIN-co ETHYLENE OXIDE-co-ALLY GLYCIDYL ETHER | 26587-37-1 | | |
| Shell-EP-25 | CASTOR OIL GLYCIDYL ETHER | 74398-71-3 | | |
| Shell-EP-26 | TETRA-PHENYLOLETHANE GLYCIDYL ETHER | / | | |
| Shell-EP-27 | EPON RESINS-828 | / | | |

Results are shown in Tables 11-18. Results collated in this series of example show that the core-shell particles of the invention display higher rate of binding for phosphate over bare, non-encapsulated particles in simulated fluid representative of the real conditions of use.

TABLE 11

| library ID | row | column | NaOH | Shell-EP-10 | Shell-EP-12 | Shell-EP-16 | Shell-Mc-3 | bead-pi-3 | bead-pi-4 | bead-pi-5 | toluene | water | BC (mmol/gr) | SI (—) |
|---|---|---|---|---|---|---|---|---|---|---|---|---|---|---|
| 100433 | A | 1 | 0.00 | | | | | 1.25 | | | | 23.75 | 0.41 | 0.76 |
| 100433 | A | 2 | 0.00 | | | | | 1.25 | | | | 23.75 | 0.46 | 0.85 |
| 100433 | A | 3 | 0.00 | | | | | 1.25 | | | | 23.75 | 0.43 | 0.81 |
| 100433 | A | 4 | 0.00 | | | | | 1.25 | | | | 23.75 | 0.40 | 0.74 |
| 100433 | A | 5 | 0.00 | | | | | 1.25 | | | | 23.75 | 0.40 | 0.75 |
| 100433 | A | 6 | 0.00 | | | | | 1.25 | | | | 23.75 | 0.48 | 0.90 |
| 100433 | B | 1 | 0.00 | | | | | 1.25 | | | | 23.75 | 0.50 | 0.93 |
| 100433 | B | 2 | 0.00 | | | | | 1.25 | | | | 23.75 | 0.51 | 0.94 |
| 100433 | B | 3 | 0.00 | | | | | 1.25 | | | | 23.75 | 0.58 | 1.07 |
| 100433 | B | 4 | 0.00 | | | | | 1.25 | | | | 23.75 | 0.64 | 1.19 |
| 100433 | B | 5 | 0.00 | | | | | 1.25 | | | | 23.75 | 0.38 | 0.70 |
| 100433 | B | 6 | 0.00 | | | | | 1.25 | | | | 23.75 | 0.35 | 0.66 |
| 100433 | C | 1 | 0.10 | | | | | 1.25 | | | | 23.66 | 0.29 | 0.55 |
| 100433 | C | 2 | 0.10 | | | | | 1.25 | | | | 23.66 | 0.60 | 1.12 |
| 100433 | C | 3 | 0.10 | | | | | 1.25 | | | | 23.66 | 0.49 | 0.91 |
| 100433 | C | 4 | 0.10 | | | | | 1.25 | | | | 23.66 | 0.70 | 1.30 |
| 100433 | C | 5 | 0.10 | | | | | 1.25 | | | | 23.66 | 0.44 | 0.82 |
| 100433 | C | 6 | | | | | | 25.00 | | | | | 0.54 | 1.00 |
| 100433 | D | 1 | | | | | | 1.25 | | | 23.75 | | 0.56 | 1.03 |
| 100433 | D | 2 | | | | | | 1.25 | | | 23.75 | | 0.63 | 1.18 |
| 100433 | D | 3 | | | | | | 1.25 | | | 23.75 | | 0.50 | 0.94 |
| 100433 | D | 4 | | | | | | 1.25 | | | 23.75 | | 0.57 | 1.06 |
| 100433 | D | 5 | | | | | | 1.25 | | | 23.75 | | 0.43 | 0.80 |
| 100461 | A | 1 | | | | | 24.00 | | | 120.00 | | 2256.00 | 1.47 | 1.08 |
| 100461 | A | 2 | | | | | 56.40 | | | 141.00 | | 2622.60 | 1.46 | 1.07 |
| 100461 | A | 3 | | | | | 95.88 | | | 159.80 | | 2940.32 | 1.45 | 1.07 |
| 100461 | A | 4 | | | | | 124.00 | | | 155.00 | | 2821.00 | 1.48 | 1.09 |
| 100461 | A | 5 | | | | | 108.60 | | | 108.60 | | 1954.80 | 1.40 | 1.03 |
| 100461 | B | 1 | | 32.92 | | | | | | 164.60 | | 3094.48 | 1.26 | 0.92 |
| 100461 | B | 2 | | 59.04 | | | | | | 147.60 | | 2745.36 | 1.51 | 1.11 |
| 100461 | B | 3 | | 96.24 | | | | | | 160.40 | | 2951.36 | 1.48 | 1.09 |
| 100461 | B | 4 | | 129.12 | | | | | | 161.40 | | 2937.48 | 1.46 | 1.07 |
| 100461 | B | 5 | | 136.10 | | | | | | 136.10 | | 2449.80 | 1.57 | 1.15 |
| 100461 | C | 1 | | | 33.18 | | | | | 165.90 | | 3118.92 | 1.38 | 1.02 |
| 100461 | C | 2 | | | 54.20 | | | | | 135.50 | | 2520.30 | 1.39 | 1.02 |
| 100461 | C | 3 | | | 90.36 | | | | | 150.60 | | 2771.04 | 1.53 | 1.13 |
| 100461 | C | 4 | | | 93.36 | | | | | 116.70 | | 2123.94 | 1.35 | 1.00 |
| 100461 | C | 5 | | | 148.70 | | | | | 148.70 | | 2676.60 | 1.52 | 1.12 |
| 100461 | C | 6 | | | | | | | | 165.10 | | | 1.36 | 1.00 |
| 100461 | D | 1 | | | | 32.56 | | | | 162.80 | | 3060.64 | 1.37 | 1.01 |
| 100461 | D | 2 | | | | 75.16 | | | | 187.90 | | 3494.94 | 1.24 | 0.91 |
| 100461 | D | 3 | | | | 65.94 | | | | 109.90 | | 2022.16 | 1.44 | 1.06 |
| 100461 | D | 4 | | | | 100.08 | | | | 125.10 | | 2276.82 | 1.49 | 1.10 |
| 100461 | D | 5 | | | | 166.30 | | | | 166.30 | | 2993.40 | 1.47 | 1.08 |
| 100462 | A | 1 | | | | | 24.21 | | 121.02 | | | 2275.23 | 1.51 | 1.13 |
| 100462 | A | 2 | | | | | 44.65 | | 111.62 | | | 2076.04 | 1.54 | 1.15 |
| 100462 | A | 3 | | | | | 64.15 | | 106.91 | | | 1967.16 | 1.45 | 1.08 |
| 100462 | A | 4 | | | | | 76.94 | | 96.18 | | | 1750.48 | 1.46 | 1.09 |
| 100462 | A | 5 | | | | | 109.49 | | 109.49 | | | 1970.89 | 1.53 | 1.14 |
| 100462 | B | 1 | | 22.44 | | | | | 112.20 | | | 2109.42 | 1.49 | 1.11 |
| 100462 | B | 2 | | 45.46 | | | | | 113.65 | | | 2113.93 | 1.41 | 1.05 |
| 100462 | B | 3 | | 67.79 | | | | | 112.98 | | | 2078.83 | 1.55 | 1.16 |
| 100462 | B | 4 | | 89.96 | | | | | 112.46 | | | 2046.68 | 1.55 | 1.16 |
| 100462 | B | 5 | | 102.12 | | | | | 102.12 | | | 1838.21 | 1.51 | 1.12 |
| 100462 | C | 1 | | | 22.22 | | | | 111.09 | | | 2088.49 | 1.69 | 1.26 |
| 100462 | C | 2 | | | 42.97 | | | | 107.44 | | | 1998.31 | 1.76 | 1.31 |
| 100462 | C | 3 | | | 59.03 | | | | 98.39 | | | 1810.28 | 1.74 | 1.30 |
| 100462 | C | 4 | | | 86.34 | | | | 107.92 | | | 1964.13 | 1.59 | 1.18 |
| 100462 | C | 5 | | | 108.15 | | | | 108.15 | | | 1946.70 | 1.48 | 1.10 |
| 100462 | C | 6 | | | | | | | 100.30 | | | 377.30 | 1.34 | 1.00 |
| 100462 | D | 1 | | | | 20.03 | | | 100.15 | | | 1882.80 | 1.60 | 1.20 |
| 100462 | D | 2 | | | | 38.24 | | | 95.59 | | | 1778.01 | 1.80 | 1.34 |
| 100462 | D | 3 | | | | 56.73 | | | 94.54 | | | 1739.57 | 1.75 | 1.31 |
| 100462 | D | 4 | | | | 85.36 | | | 106.70 | | | 1941.96 | 2.00 | 1.49 |
| 100462 | D | 5 | | | | 103.19 | | | 103.19 | | | 1857.49 | 2.06 | 1.54 |

TABLE 12

| library ID | row | column | Shell-AH-11 | Shell-AH-9 | Shell-EP-8 | Shell-IC-1 | bead-pi-5 | ethyl acetate | methanol | toluene | water | BC (mmol/gr) | SI (—) |
|---|---|---|---|---|---|---|---|---|---|---|---|---|---|
| 100468 | A | 1 | | 31.70 | | | 158.50 | 2979.80 | | | | 1.48 | 0.96 |
| 100468 | A | 2 | | 76.28 | | | 190.70 | 3547.02 | | | | 1.63 | 1.06 |
| 100468 | A | 3 | | 106.20 | | | 177.00 | 3256.80 | | | | 1.56 | 1.01 |
| 100468 | A | 4 | | 133.20 | | | 166.50 | 3030.30 | | | | 1.50 | 0.98 |
| 100468 | A | 5 | | 123.40 | | | 123.40 | 2221.20 | | | | 1.53 | 0.99 |
| 100468 | B | 1 | 28.06 | | | | 140.30 | 2637.64 | | | | 1.70 | 1.10 |
| 100468 | B | 2 | 52.48 | | | | 131.20 | 2440.32 | | | | 1.60 | 1.04 |
| 100468 | B | 3 | 84.48 | | | | 140.80 | 2590.72 | | | | 1.70 | 1.10 |
| 100468 | B | 4 | 106.00 | | | | 132.50 | 2411.50 | | | | 1.73 | 1.12 |
| 100468 | B | 5 | 146.40 | | | | 146.40 | 2635.20 | | | | 1.70 | 1.11 |
| 100468 | C | 1 | | | | 28.96 | 144.80 | | | 2722.24 | | 1.53 | 0.99 |
| 100468 | C | 2 | | | | 50.20 | 125.50 | | | 2334.30 | | 1.45 | 0.94 |
| 100468 | C | 3 | | | | 93.48 | 155.80 | | | 2866.72 | | 1.48 | 0.96 |
| 100468 | C | 4 | | | | 140.24 | 175.30 | | | 3190.46 | | 1.37 | 0.89 |
| 100468 | C | 5 | | | | 188.80 | 188.80 | | | 3398.40 | | 1.19 | 0.78 |
| 100468 | C | 6 | | | | | 221.10 | | | | | 1.54 | 1.00 |
| 100468 | D | 1 | | | 41.38 | | 206.90 | | | 3889.72 | | 1.44 | 0.94 |
| 100468 | D | 2 | | | 61.84 | | 154.60 | | | 2875.56 | | 1.49 | 0.97 |
| 100468 | D | 3 | | | 109.62 | | 182.70 | | | 3361.68 | | 1.46 | 0.95 |
| 100468 | D | 4 | | | 117.04 | | 146.30 | | | 2662.66 | | 1.45 | 0.94 |
| 100468 | D | 5 | | | 148.20 | | 148.20 | | | 2667.60 | | 1.46 | 0.95 |

TABLE 13

| library ID | row | column | Shell-EP-1 | Shell-EP-10 | Shell-EP-12bis | Shell-EP-13 | Shell-Mc-2 | bead-pi-5 | ethyl acetate | toluene | BC (mmol/gr) | SI (—) |
|---|---|---|---|---|---|---|---|---|---|---|---|---|
| 100473 | A | 1 | | 94.02 | | | | 156.70 | | 2883.28 | 1.68 | 1.10 |
| 100473 | A | 2 | | 89.82 | | | | 149.70 | | 2754.48 | 1.52 | 0.99 |
| 100473 | A | 3 | | 114.12 | | | | 190.20 | | 3499.68 | 1.57 | 1.02 |
| 100473 | A | 4 | | 95.76 | | | | 159.60 | | 2936.64 | 1.47 | 0.96 |
| 100473 | A | 5 | | 81.12 | | | | 135.20 | | 2487.68 | 1.47 | 0.96 |
| 100473 | B | 1 | | 98.52 | | | | 164.20 | | 3021.28 | 1.49 | 0.97 |
| 100473 | B | 2 | | 98.76 | | | | 164.60 | | 3028.64 | 1.44 | 0.94 |
| 100473 | B | 3 | | 109.80 | | | | 183.00 | | 3367.20 | 1.37 | 0.89 |
| 100473 | B | 4 | | 92.70 | | | | 154.50 | | 2842.80 | 1.41 | 0.92 |
| 100473 | B | 5 | | 114.24 | | | | 190.40 | | 3503.36 | 1.46 | 0.96 |
| 100473 | C | 1 | | 90.18 | | | | 150.30 | | 2765.52 | 1.46 | 0.95 |
| 100473 | C | 2 | | 90.00 | | | | 150.00 | | 2760.00 | 1.43 | 0.94 |
| 100473 | C | 3 | | 82.74 | | | | 137.90 | | 2537.36 | 1.41 | 0.92 |
| 100473 | C | 4 | | 99.12 | | | | 165.20 | | 3039.68 | 1.35 | 0.88 |
| 100473 | C | 5 | | 106.32 | | | | 177.20 | | 3260.48 | 1.36 | 0.89 |
| 100473 | C | 6 | | | | | | 212.40 | | | 1.53 | 1.00 |
| 100473 | D | 1 | | 90.84 | | | | 151.40 | | 2785.76 | 1.24 | 0.81 |
| 100473 | D | 2 | | 100.68 | | | | 167.80 | | 3087.52 | 1.42 | 0.93 |
| 100473 | D | 3 | | 113.82 | | | | 189.70 | | 3490.48 | 1.45 | 0.95 |
| 100473 | D | 4 | | 105.36 | | | | 175.60 | | 3231.04 | 1.46 | 0.95 |
| 100473 | D | 5 | | 90.30 | | | | 150.50 | | 2769.20 | 1.51 | 0.99 |
| 100474 | A | 1 | | 90.18 | | | | 150.30 | | 2765.52 | 1.64 | 1.19 |
| 100474 | A | 2 | | 86.88 | | | | 144.80 | | 2664.32 | 1.42 | 1.03 |
| 100474 | A | 3 | | 101.94 | | | | 169.90 | | 3126.16 | 1.26 | 0.91 |
| 100474 | A | 4 | | 100.92 | | | | 168.20 | | 3094.88 | 1.36 | 0.99 |
| 100474 | A | 5 | | 94.32 | | | | 157.20 | | 2892.48 | 1.47 | 1.07 |
| 100474 | B | 1 | | 88.02 | | | | 146.70 | | 2699.28 | 1.36 | 0.98 |
| 100474 | B | 2 | | 95.70 | | | | 159.50 | | 2934.80 | 1.37 | 0.99 |
| 100474 | B | 3 | | 89.88 | | | | 149.80 | | 2756.32 | 1.48 | 1.07 |
| 100474 | B | 4 | | 109.02 | | | | 181.70 | | 3343.28 | 1.40 | 1.02 |
| 100474 | B | 5 | | 86.46 | | | | 144.10 | | 2651.44 | 1.43 | 1.04 |
| 100474 | C | 1 | | 84.60 | | | | 141.00 | | 2594.40 | 1.42 | 1.03 |
| 100474 | C | 2 | | 89.52 | | | | 149.20 | | 2745.28 | 1.45 | 1.05 |
| 100474 | C | 3 | | 84.72 | | | | 141.20 | | 2598.08 | 1.48 | 1.07 |
| 100474 | C | 4 | | 112.02 | | | | 186.70 | | 3435.28 | 1.44 | 1.04 |
| 100474 | C | 5 | | 104.58 | | | | 174.30 | | 3207.12 | 1.42 | 1.03 |
| 100474 | C | 6 | | | | | | 216.20 | | | 1.38 | 1.00 |
| 100474 | D | 1 | | 94.50 | | | | 157.50 | | 2898.00 | 1.48 | 1.07 |
| 100474 | D | 2 | | 110.40 | | | | 184.00 | | 3385.60 | 1.42 | 1.03 |
| 100474 | D | 3 | | 102.18 | | | | 170.30 | | 3133.52 | 1.72 | 1.25 |
| 100474 | D | 4 | | 87.84 | | | | 146.40 | | 2693.76 | 1.54 | 1.12 |
| 100474 | D | 5 | | 97.86 | | | | 163.10 | | 3001.04 | 1.53 | 1.11 |
| 100480 | A | 1 | | | 29.76 | | | 148.80 | 2797.44 | | 1.32 | 0.95 |
| 100480 | A | 2 | | | 77.96 | | | 194.90 | 3625.14 | | 1.18 | 0.85 |
| 100480 | A | 3 | | | 102.24 | | | 170.40 | 3135.36 | | 0.95 | 0.68 |
| 100480 | A | 4 | | | 133.28 | | | 166.60 | 3032.12 | | 0.79 | 0.57 |
| 100480 | A | 5 | | | 143.90 | | | 143.90 | 2590.20 | | 0.80 | 0.57 |

TABLE 13-continued

| library ID | row | column | Shell-EP-1 | Shell-EP-10 | Shell-EP-12bis | Shell-EP-13 | Shell-Mc-2 | bead-pi-5 | ethyl acetate | toluene | BC (mmol/gr) | SI (—) |
|---|---|---|---|---|---|---|---|---|---|---|---|---|
| 100480 | B | 1 | | | | 32.08 | | 160.40 | 3015.52 | | 0.99 | 0.71 |
| 100480 | B | 2 | | | | 69.20 | | 173.00 | 3217.80 | | 1.14 | 0.82 |
| 100480 | B | 3 | | | | 112.20 | | 187.00 | 3440.80 | | 1.24 | 0.89 |
| 100480 | B | 4 | | | | 130.72 | | 163.40 | 2973.88 | | 1.35 | 0.96 |
| 100480 | B | 5 | | | | 155.80 | | 155.80 | 2804.40 | | 1.12 | 0.80 |
| 100480 | C | 1 | 31.16 | | | | | 155.80 | | 2929.04 | 1.25 | 0.90 |
| 100480 | C | 2 | 56.00 | | | | | 140.00 | | 2604.00 | 1.30 | 0.93 |
| 100480 | C | 3 | 95.16 | | | | | 158.60 | | 2918.24 | 1.45 | 1.03 |
| 100480 | C | 4 | 157.76 | | | | | 197.20 | | 3589.04 | 1.56 | 1.12 |
| 100480 | C | 5 | 162.60 | | | | | 162.60 | | 2926.80 | 1.55 | 1.11 |
| 100480 | C | 6 | | | | | | 149.00 | | | 1.40 | 1.00 |
| 100480 | D | 1 | | | | | 29.76 | 148.80 | | 2797.44 | 1.44 | 1.03 |
| 100480 | D | 2 | | | | | 73.68 | 184.20 | | 3426.12 | 1.39 | 0.99 |
| 100480 | D | 3 | | | | | 93.78 | 156.30 | | 2875.92 | 1.39 | 1.00 |
| 100480 | D | 4 | | | | | 131.36 | 164.20 | | 2988.44 | 1.34 | 0.96 |
| 100480 | D | 5 | | | | | 145.10 | 145.10 | | 2611.80 | 1.31 | 0.94 |

TABLE 14

| library ID | row | column | Shell-EP-11 | Shell-EP-12 bis | Shell-EP-8 | Shell-EP-9 | bead-pi-4 | bead-pi-5 | ethyl acetate | methanol | toluene | BC (mmol/gr) | SI (—) |
|---|---|---|---|---|---|---|---|---|---|---|---|---|---|
| 100484 | A | 1 | | 3.41 | | | | 170.70 | 3239.89 | | | 1.89 | 1.36 |
| 100484 | A | 2 | | 10.50 | | | | 161.50 | 3058.00 | | | 1.78 | 1.29 |
| 100484 | A | 3 | | 20.14 | | | | 183.10 | 3458.76 | | | 1.82 | 1.31 |
| 100484 | A | 4 | | 21.39 | | | | 138.00 | 2600.61 | | | 1.36 | 0.98 |
| 100484 | A | 5 | | 32.66 | | | | 163.30 | 3070.04 | | | 1.29 | 0.93 |
| 100484 | B | 1 | | | 3.17 | | | 158.30 | | | 3004.53 | 1.85 | 1.33 |
| 100484 | B | 2 | | | 10.22 | | | 157.20 | | | 2976.58 | 1.93 | 1.39 |
| 100484 | B | 3 | | | 19.91 | | | 181.00 | | | 3419.09 | 1.83 | 1.32 |
| 100484 | B | 4 | | | 25.05 | | | 161.60 | | | 3045.35 | 1.89 | 1.36 |
| 100484 | B | 5 | | | 29.72 | | | 148.60 | | | 2793.68 | 1.91 | 1.38 |
| 100484 | C | 1 | | | | 2.99 | | 149.50 | | | 2837.51 | 2.09 | 1.51 |
| 100484 | C | 2 | | | | 10.04 | | 154.40 | | | 2923.56 | 1.95 | 1.41 |
| 100484 | C | 3 | | | | 19.93 | | 181.20 | | | 3422.87 | 1.83 | 1.32 |
| 100484 | C | 4 | | | | 25.76 | | 166.20 | | | 3132.04 | 1.80 | 1.30 |
| 100484 | C | 5 | | | | 30.60 | | 153.00 | | | 2876.40 | 1.85 | 1.33 |
| 100484 | C | 6 | | | | | | 211.50 | | | | 1.39 | 1.00 |
| 100484 | D | 1 | 3.07 | | | | | 153.30 | | | 2909.63 | 1.39 | 1.00 |
| 100484 | D | 2 | 12.33 | | | | | 189.70 | | | 3591.97 | 1.88 | 1.35 |
| 100484 | D | 3 | 18.22 | | | | | 165.60 | | | 3128.18 | 1.76 | 1.27 |
| 100484 | D | 4 | 27.27 | | | | | 175.90 | | | 3314.84 | 1.77 | 1.27 |
| 100484 | D | 5 | 32.16 | | | | | 160.80 | | | 3023.04 | 1.83 | 1.32 |
| 100485 | A | 1 | | | 3.05 | | 152.36 | | 2318.55 | 573.15 | | 1.29 | 0.92 |
| 100485 | A | 2 | | | 9.71 | | 149.33 | | 2265.81 | 561.77 | | 1.03 | 0.73 |
| 100485 | A | 3 | | | 17.53 | | 159.33 | | 2410.31 | 599.37 | | 1.04 | 0.74 |
| 100485 | A | 4 | | | 25.50 | | 164.51 | | 2481.38 | 618.89 | | | |
| 100485 | A | 5 | | | 35.53 | | 177.66 | | 2671.67 | 668.34 | | 0.89 | 0.63 |
| 100485 | B | 1 | | | | 3.34 | 167.03 | | | | 3170.31 | 1.39 | 0.98 |
| 100485 | B | 2 | | | | 8.54 | 131.44 | | | | 2488.80 | 0.69 | 0.49 |
| 100485 | B | 3 | | | | 16.87 | 153.38 | | | | 2897.42 | 1.12 | 0.80 |
| 100485 | B | 4 | | | | 23.64 | 152.48 | | | | 2873.50 | 1.49 | 1.06 |
| 100485 | B | 5 | | | | 33.68 | 168.42 | | | | 3166.30 | 1.55 | 1.10 |
| 100485 | C | 1 | | | | | 3.06 | 152.78 | | | 2899.67 | 1.31 | 0.93 |
| 100485 | C | 2 | | | | | 9.44 | 145.19 | | | 2749.25 | 1.50 | 1.06 |
| 100485 | C | 3 | | | | | 16.51 | 150.09 | | | 2835.14 | 1.49 | 1.05 |
| 100485 | C | 4 | | | | | 24.86 | 160.40 | | | 3022.70 | 1.42 | 1.01 |
| 100485 | C | 5 | | | | | 28.96 | 144.82 | | | 2722.54 | 1.36 | 0.96 |
| 100485 | C | 6 | | | | | | 139.29 | | | 524.01 | 1.41 | 1.00 |
| 100485 | D | 1 | 3.02 | | | | | 150.99 | | | 2865.79 | 1.45 | 1.03 |
| 100485 | D | 2 | 10.35 | | | | | 159.29 | | | 3016.06 | 1.48 | 1.05 |
| 100485 | D | 3 | 22.61 | | | | | 205.53 | | | 3882.41 | 1.02 | 0.73 |
| 100485 | D | 4 | 23.91 | | | | | 154.29 | | | 2907.54 | 1.24 | 0.88 |
| 100485 | D | 5 | 28.81 | | | | | 144.06 | | | 2708.33 | 0.82 | 0.58 |

TABLE 15

Library: Plate1 (ID: 100500) Unit: mg

| Row | Col | bead-pi-4 | toluene | Shell-EP-12 | BC (mmol/gr) | SI (—) |
|---|---|---|---|---|---|---|
| 1.00 | 1.00 | 171.99 | 3233.41 | 34.40 | 1.31 | 1.26 |
| 1.00 | 2.00 | 144.02 | 2678.73 | 57.61 | 0.93 | 0.90 |
| 1.00 | 3.00 | 152.57 | 2807.20 | 91.54 | 1.15 | 1.10 |
| 1.00 | 4.00 | 156.60 | 2850.07 | 125.28 | 0.71 | 0.68 |
| 1.00 | 5.00 | 156.32 | 2813.83 | 156.32 | 0.78 | 0.75 |
| 2.00 | 1.00 | 156.72 | 2946.39 | 31.34 | 1.39 | 1.33 |
| 2.00 | 2.00 | 156.74 | 2915.44 | 62.70 | 1.61 | 1.54 |
| 2.00 | 3.00 | 154.35 | 2840.04 | 92.61 | 2.08 | 1.99 |
| 2.00 | 4.00 | 154.35 | 2809.17 | 123.48 | 0.53 | 0.50 |
| 2.00 | 5.00 | 153.59 | 2764.69 | 153.59 | 0.60 | 0.57 |
| 2.00 | 6.00 | 140.87 | 529.93 | 0.00 | 0.89 | 0.86 |
| 3.00 | 1.00 | 140.18 | 2635.29 | 28.04 | 1.15 | 1.11 |
| 3.00 | 2.00 | 148.66 | 2765.06 | 59.46 | 1.84 | 1.77 |
| 3.00 | 3.00 | 142.44 | 2620.95 | 85.47 | 1.72 | 1.65 |
| 3.00 | 4.00 | 149.00 | 2711.71 | 119.20 | 2.27 | 2.18 |
| 3.00 | 5.00 | 137.05 | 2466.83 | 137.05 | 0.73 | 0.70 |
| 3.00 | 6.00 | 153.03 | 575.67 | 0.00 | 1.04 | 1.00 |
| 4.00 | 1.00 | 141.54 | 2660.95 | 28.31 | 1.24 | 1.19 |
| 4.00 | 2.00 | 148.47 | 2761.54 | 59.39 | 1.60 | 1.54 |
| 4.00 | 3.00 | 130.16 | 2394.19 | 78.09 | 1.17 | 1.12 |
| 4.00 | 4.00 | 137.76 | 2507.23 | 110.21 | 1.37 | 1.31 |
| 4.00 | 5.00 | 140.22 | 2523.91 | 140.22 | 0.96 | 0.93 |

TABLE 16

Library: Plate2 (ID: 100501) Unit: mg

| Row | Col | bead-pi-4 | toluene | Shell-EP-16 | BC (mmol/gr) | SI (—) |
|---|---|---|---|---|---|---|
| 1.00 | 1.00 | 150.72 | 2833.48 | 30.14 | 0.94 | 0.87 |
| 1.00 | 2.00 | 150.15 | 2792.79 | 60.06 | 1.22 | 1.12 |
| 1.00 | 3.00 | 143.91 | 2648.00 | 86.35 | 1.33 | 1.23 |
| 1.00 | 4.00 | 153.43 | 2792.35 | 122.74 | 1.81 | 1.67 |
| 1.00 | 5.00 | 154.94 | 2788.88 | 154.94 | 1.01 | 0.94 |
| 2.00 | 1.00 | 150.32 | 2825.98 | 30.06 | 1.00 | 0.93 |
| 2.00 | 2.00 | 149.12 | 2773.65 | 59.65 | 1.44 | 1.33 |
| 2.00 | 3.00 | 149.18 | 2744.99 | 89.51 | 1.93 | 1.78 |
| 2.00 | 4.00 | 147.19 | 2678.84 | 117.75 | 1.49 | 1.38 |
| 2.00 | 5.00 | 147.82 | 2660.74 | 147.82 | 0.92 | 0.85 |
| 2.00 | 6.00 | 147.27 | 554.03 | 0.00 | 0.92 | 0.85 |
| 3.00 | 1.00 | 140.45 | 2640.42 | 28.09 | 0.96 | 0.88 |
| 3.00 | 2.00 | 141.39 | 2629.91 | 56.56 | 1.50 | 1.39 |
| 3.00 | 3.00 | 140.51 | 2585.40 | 84.31 | 0.96 | 0.89 |
| 3.00 | 4.00 | 149.00 | 2711.71 | 119.20 | 1.76 | 1.63 |
| 3.00 | 5.00 | 131.23 | 2362.12 | 131.23 |  | 0.00 |
| 3.00 | 6.00 | 150.21 | 565.09 | 0.00 | 1.08 | 1.00 |
| 4.00 | 1.00 | 149.21 | 2805.05 | 29.84 | 0.98 | 0.91 |
| 4.00 | 2.00 | 151.98 | 2826.77 | 60.79 | 1.33 | 1.23 |
| 4.00 | 3.00 | 155.36 | 2858.59 | 93.21 | 1.40 | 1.30 |
| 4.00 | 4.00 | 173.78 | 3162.71 | 139.02 | 2.00 | 1.85 |
| 4.00 | 5.00 | 144.52 | 2601.40 | 144.52 | 2.10 | 1.94 |

TABLE 17

Library: Plate2 (ID: 100487) Unit: mg

| Row | Col | bead-pi-4 | toluene | Shell-EP-9 | Shell-EP-2 | Shell-EP-14 | ethyl acetate | BC (mmol/gr) | SI (—) |
|---|---|---|---|---|---|---|---|---|---|
| 1.00 | 1.00 | 164.43 | 3091.28 | 8.22 | 24.66 | 0.00 | 0.00 | 0.66 | 0.87 |
| 1.00 | 2.00 | 145.70 | 2709.98 | 14.57 | 43.71 | 0.00 | 0.00 | 0.27 | 0.36 |
| 1.00 | 3.00 | 147.57 | 2715.23 | 22.14 | 66.41 | 0.00 | 0.00 | 0.26 | 0.35 |
| 1.00 | 4.00 | 149.25 | 2716.30 | 29.85 | 89.55 | 0.00 | 0.00 | 0.54 | 0.71 |
| 1.00 | 5.00 | 150.19 | 2703.46 | 37.55 | 112.64 | 0.00 | 0.00 | 0.46 | 0.60 |
| 2.00 | 1.00 | 143.43 | 2696.48 | 9.56 | 19.12 | 0.00 | 0.00 | 0.57 | 0.76 |
| 2.00 | 2.00 | 134.19 | 2495.93 | 17.89 | 35.78 | 0.00 | 0.00 | 0.57 | 0.76 |
| 2.00 | 3.00 | 137.07 | 2522.03 | 27.41 | 54.83 | 0.00 | 0.00 | 0.56 | 0.74 |
| 2.00 | 4.00 | 134.36 | 2445.32 | 35.83 | 71.66 | 0.00 | 0.00 | 0.53 | 0.70 |
| 2.00 | 5.00 | 133.22 | 2398.03 | 44.41 | 88.82 | 0.00 | 0.00 | 0.51 | 0.68 |
| 3.00 | 1.00 | 136.77 | 2386.69 | 6.84 | 0.00 | 20.52 | 184.64 | 0.50 | 0.66 |
| 3.00 | 2.00 | 151.94 | 2415.77 | 15.19 | 0.00 | 45.58 | 410.22 | 1.14 | 1.52 |
| 3.00 | 3.00 | 150.82 | 2164.30 | 22.62 | 0.00 | 67.87 | 610.83 | 1.50 | 1.98 |
| 3.00 | 4.00 | 155.74 | 1993.42 | 31.15 | 0.00 | 93.44 | 840.97 | 1.12 | 1.48 |
| 3.00 | 5.00 | 157.73 | 1774.47 | 39.43 | 0.00 | 118.30 | 1064.68 | 0.94 | 1.24 |
| 3.00 | 6.00 | 153.01 | 575.59 | 0.00 | 0.00 | 0.00 | 0.00 | 0.75 | 1.00 |
| 4.00 | 1.00 | 155.30 | 2733.19 | 10.35 | 0.00 | 20.71 | 186.35 | 0.50 | 0.67 |
| 4.00 | 2.00 | 150.36 | 2435.83 | 20.05 | 0.00 | 40.10 | 360.86 | 1.03 | 1.36 |
| 4.00 | 3.00 | 153.95 | 2278.47 | 30.79 | 0.00 | 61.58 | 554.22 | 1.36 | 1.80 |
| 4.00 | 4.00 | 151.60 | 2031.43 | 40.43 | 0.00 | 80.85 | 727.68 | 1.38 | 1.83 |
| 4.00 | 5.00 | 151.56 | 1818.68 | 50.52 | 0.00 | 101.04 | 909.34 | 1.24 | 1.64 |

TABLE 18

Library: Plate1 (ID: 100486) Unit: mg

| Row | Col | bead-pi-4 | toluene | Shell-EP-9 | Shell-EP-11 | Shell-EP-2 | Shell-EP-14 | ethyl acetate | BC (mmol/gr) | SI (—) |
|---|---|---|---|---|---|---|---|---|---|---|
| 1.00 | 1.00 | 138.29 | 2599.76 | 27.66 | 0.00 | 0.00 | 0.00 | 0.00 | 0.69 | 0.95 |
| 1.00 | 2.00 | 150.40 | 2797.48 | 60.16 | 0.00 | 0.00 | 0.00 | 0.00 | 0.62 | 0.85 |
| 1.00 | 3.00 | 152.42 | 2804.49 | 91.45 | 0.00 | 0.00 | 0.00 | 0.00 | 0.59 | 0.82 |
| 1.00 | 4.00 | 157.56 | 2867.65 | 126.05 | 0.00 | 0.00 | 0.00 | 0.00 | 0.44 | 0.61 |
| 1.00 | 5.00 | 140.22 | 2523.91 | 140.22 | 0.00 | 0.00 | 0.00 | 0.00 | 0.40 | 0.56 |
| 2.00 | 1.00 | 153.01 | 2876.51 | 0.00 | 30.60 | 0.00 | 0.00 | 0.00 | 0.40 | 0.55 |
| 2.00 | 2.00 | 154.37 | 2871.30 | 0.00 | 61.75 | 0.00 | 0.00 | 0.00 | 0.32 | 0.44 |
| 2.00 | 3.00 | 162.50 | 2989.96 | 0.00 | 97.50 | 0.00 | 0.00 | 0.00 | 0.43 | 0.60 |
| 2.00 | 4.00 | 150.26 | 2734.64 | 0.00 | 120.20 | 0.00 | 0.00 | 0.00 | 0.36 | 0.49 |
| 2.00 | 5.00 | 139.04 | 2502.74 | 0.00 | 139.04 | 0.00 | 0.00 | 0.00 | 0.44 | 0.61 |
| 3.00 | 1.00 | 157.29 | 2957.05 | 0.00 | 0.00 | 31.46 | 0.00 | 0.00 | 0.29 | 0.40 |
| 3.00 | 2.00 | 153.91 | 2862.71 | 0.00 | 0.00 | 61.56 | 0.00 | 0.00 | 0.33 | 0.45 |
| 3.00 | 3.00 | 150.84 | 2775.51 | 0.00 | 0.00 | 90.51 | 0.00 | 0.00 | 0.40 | 0.55 |

TABLE 18-continued

Library: Plate1 (ID: 100486) Unit: mg

| Row | Col | bead-pi-4 | toluene | Shell-EP-9 | Shell-EP-11 | Shell-EP-2 | Shell-EP-14 | ethyl acetate | BC (mmol/gr) | SI (—) |
|---|---|---|---|---|---|---|---|---|---|---|
| 3.00 | 4.00 | 162.02 | 2948.67 | 0.00 | 0.00 | 129.61 | 0.00 | 0.00 | 0.35 | 0.49 |
| 3.00 | 5.00 | 154.41 | 2779.43 | 0.00 | 0.00 | 154.41 | 0.00 | 0.00 | 0.38 | 0.53 |
| 3.00 | 6.00 | 161.45 | 607.35 | 0.00 | 0.00 | 0.00 | 0.00 | 0.00 | 0.72 | 1.00 |
| 4.00 | 1.00 | 156.49 | 2660.36 | 0.00 | 0.00 | 0.00 | 31.30 | 281.69 | 0.60 | 0.83 |
| 4.00 | 2.00 | 157.65 | 2364.71 | 0.00 | 0.00 | 0.00 | 63.06 | 567.53 | 1.38 | 1.91 |
| 4.00 | 3.00 | 157.12 | 2042.59 | 0.00 | 0.00 | 0.00 | 94.27 | 848.46 | 1.46 | 2.02 |
| 4.00 | 4.00 | 153.24 | 1685.61 | 0.00 | 0.00 | 0.00 | 122.59 | 1103.31 | 1.37 | 1.89 |
| 4.00 | 5.00 | 155.00 | 1395.01 | 0.00 | 0.00 | 0.00 | 155.00 | 1395.01 | 1.20 | 1.66 |

Example 5

Binding Capacity Measurements in a Non Interfering Buffer

An aliquot of dried resin of weight P(gr), is mixed under gentle agitation with a fixed volume, V(ml), of a phosphate ion solution of concentration $C_{start}$(mM) buffered at pH 6.5. After resin equilibration, the solution is decanted by centrifugation and the supernatant analyzed for residual phosphate concentration by ionic chromatography, $C_{eq}$(mM). The binding capacity is calculated as BC (mmol/gr)=V. $(C_{start}-C_{eq})$/P.

Binding Capacity in a Ex-Vivo Aspirates

In this example healthy patients are given a meal of the same composition as the one prepared for the digestion mimic and aliquots of chyme are then sampled using a tube placed in the lumen of the small intestine.

Normal subjects are intubated with a double lumen polyvinyl tube, with a mercury weighted bag attached to the end of the tube to facilitate movement of the tube into the small intestine. One aspiration aperture of the double lumen tube is located in the stomach and the other aperture is at the Ligament of Treitz (in the upper jejunum). Placement takes place with the use of fluoroscopy.

After correct tube is placed, 550 mL of a liquid standard test meal (supplemented with a marker, polyethylene glycol (PEG)-2 g/550 mL) is infused into the stomach through the gastric aperture at a rate of 22 mL per minute. It requires approximately 25 minutes for the entire meal to reach the stomach. This rate of ingestion simulates the duration of time required to eat normal meals.

Jejunal chyme is aspirated from the tube whose lumen is located at the Ligament of Treitz. This fluid is collected continuously during 30-minute intervals for a two and a half hour period. This results in 5 specimens that are mixed, measured for volume, and lyophilized.

The phosphate binding procedure is identical to the one described earlier with the non-interfering buffer experiment, except that the ex-vivo aspirate liquid is used (after reconstitution of the freeze-dried material in the proper amount of de-ionized water). The binding capacity in the ex-vivo aspirate (VA) is calculated in the same way. Core-shell compositions bind more phosphate than the corresponding core component.

Example 6

Method of Selection of Semi-Permeable Membrane with High Potassium Binding Selectivity Over Magnesium and Calcium This protocol describes a method to optimize polymeric materials with regards to their ion permselectivity characteristics, which then can be used as the shell component for the making of potassium selective core-shell ion-exchange particles.

Polymer Synthesis and Membrane Preparation:

Polymeric membrane materials with different compositions were prepared by radical copolymerization of DBA (N,N'-dibutyl acrylamide) and DEAEMA (N,N'-diethylaminoethylmethacrylate) in a glove box using miniaturized reactors in a library format. AIBN was used as the initiator and ethanol as the solvent. Polymers were isolated by precipitation into water, freeze-dried, and characterized by GPC and H-NMR. The composition of the polymer (DBA mol %) ranges from 30% to 70% and molecular weight ranges from 200K to 300K as shown below:

TABLE 19

| | Polymer ID 101224 | | | | | |
|---|---|---|---|---|---|---|
| | D1 | D2 | D3 | D4 | D5 | D6 |
| Mn (×10³) | 327 | 326 | 322 | 285 | 240 | 217 |
| Mw (×10³) | 584 | 563 | 520 | 467 | 411 | 340 |
| PDI | 1.78 | 1.73 | 1.61 | 1.64 | 1.71 | 1.56 |
| Composition (DBA, mol %) | 31.2 | 37.1 | 48.5 | 56.1 | 64.4 | 68.5 |

Polymer membranes were prepared by casting a 2-wt % toluene solution of DBA-co-DEAEMA onto a regenerated cellulose dialysis membrane (RC membrane with MWCO of 14 K). After toluene was evaporated, a polymer membrane was formed on the top of dialysis membrane. A composite membrane of polymer membrane and RC membrane was thus prepared.

Permeability Study on Cations

Figure 3:
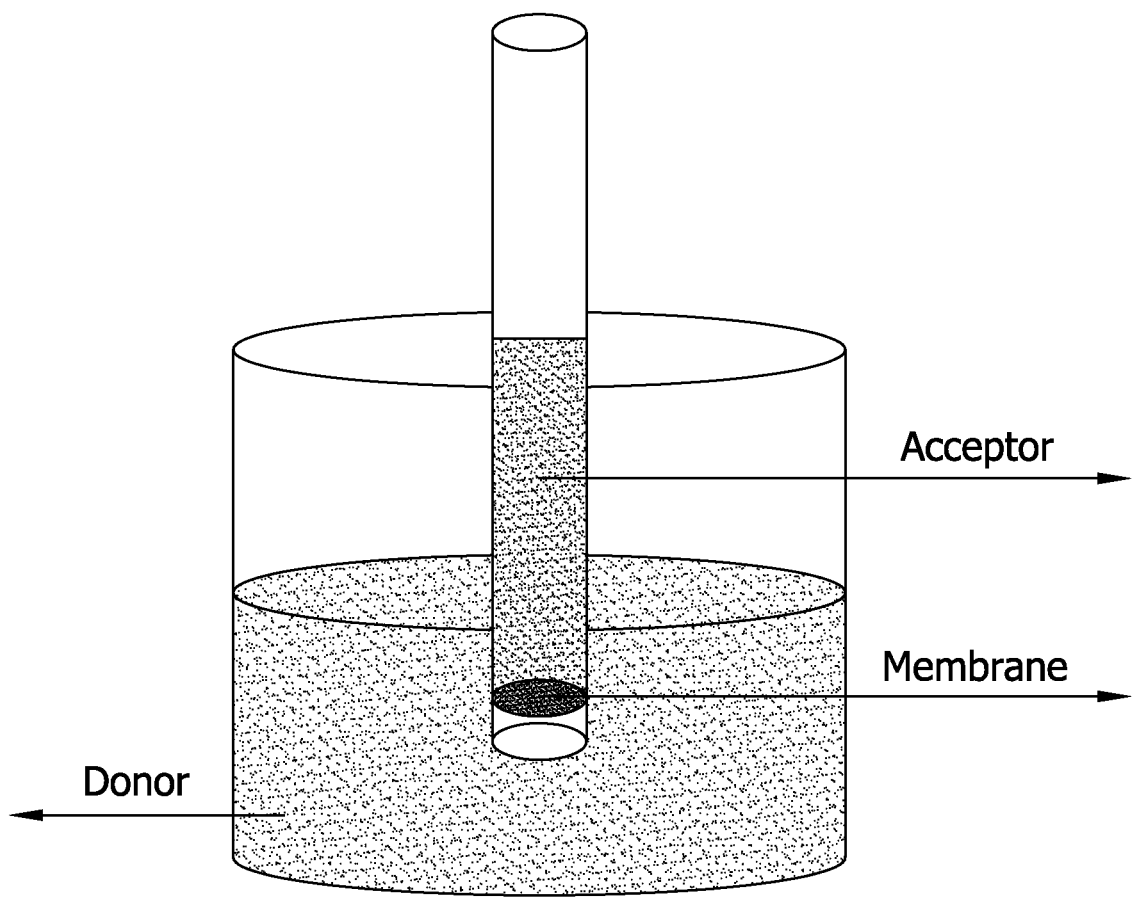
FIG. 3 depicts the membrane preparation for determination of ion permeability.

The composite membrane was first clamped onto a glass tube with diameter of 13 mm, and then immersed into a 2 L of donor solution of cations. The tube was filled with 10 ml of acceptor solution (lactose solution with the same osmolality as the donor solution (240 mM)). The acceptor solution was sampled at a specified time interval and analyzed by ion chromatography. See FIG. 3.

Donor solution was prepared by mixing the aqueous solution of NaCl, KCl, $CaCl_2.2H_2O$, and $MgSO_4.7H_2O$. The solution was buffered to pH 6 by using 14 mM of MES (2-[N-morpholine]ethanesulfonic acid] solution. The concentrations of different cations determined by IC were as follows: [$Na^+$], 40.46 mM; [$K^+$], 31.44 mM; [$Mg^{2+}$], 33.25 mM; [$Ca^{2+}$], 22.324 mM.

Determination of the permeability coefficient (P) of different cations: As mentioned in the measurement set-up, the acceptor solution was sampled at a specific time interval and analyzed by IC. Assuming a Fick's first law of diffusion, P is readily obtained by linearization of the data, following a method of calculation reported in equation 1 in G. Van den Mooter, C. Samyn, and R. Kinget, International Journal of Pharmaceutics, 111, 127-136 (1994). The permeability coefficients of different cations were thus calculated from the slope from this linear relationship.

$$-\ln\left(\frac{C_o - C_a}{C_o}\right) = \frac{PS}{V_a}t \qquad \text{Equation 1}$$

Where $C_o$ is the initial concentration of the solute in the donor compartment and $C_a$ the concentration in the acceptor compartment at time t, Va is the volume of the acceptor compartment, and S the surface of the membrane.

Permselectivity: As described above, the permeability coefficient was calculated for each cation. By normalizing the permeability coefficient of $Na^+$ as 1, the permselectivity for cations M1 and M2 can be calculated as follows: $P_{M1}^{M1}$=P(M2)/P(M1)

Permeability Coefficients of Different Cations Through Different Membranes:

Table 14 shows the permeability coefficients of different cations at different membranes. When polymers are more hydrophilic (Polymer D3 and D4 with DBA % 48.5 and 56.1%, respectively), all cations, such as $Na^+$, $K^+$, $Mg^{2+}$, and $Ca^{2+}$, are more permeable and their permeability coefficients are comparable to those through a blank dialysis membrane (RC membrane) and reflect the self-diffusivity of the cations. However, with the increasing DBA content in polymer membrane (See Table 20 for D5 and D6), the permeability coefficients of different cations decreased as compared with blank membrane, which means that the hydrophobic nature of polymer membrane could make cations less permeable through the hydrophobic barrier.

TABLE 20

Permeability coefficients of cations at different membranes

| Polymer ID | DBA (mol %) | $PNa^+$ (cm/sec) | $PK^+$ (cm/sec) | $PMg^{2+}$ (cm/sec) | $PCa^{2+}$ (cm/sec) |
|---|---|---|---|---|---|
| D3 | 48.5 | 2.41 (±0.26)E−4 | 3.11 (±0.34)E−4 | 6.50 (±0.08)E−5 | 6.0 (±0.07)E−5 |
| D4 | 56.1 | 4.28 (±0.44)E−5 | 6.11 (±0.61)E−4 | 1.13 (±0.11)E−5 | 1.04 (±0.05)E−5 |
| D5 | 64.4 | 4.32 (±0.20)E−6 | 5.79 (±3.59)E−6 | 5.42 (±4.11)E−7 | 3.32 (±3.33)E−7 |
| D6 | 68.5 | 1.50 (±0.05)E−7 | — | — | — |

Another characteristic for the permeability of different cations is their permselectivity. By normalizing the value of $P_{Na}^+$ as 1, the permselectivity for other cations can be calculated and the results are shown in Table 21. The permselectivity of $P_{Mg}/P_{Na}$ and $P_{Ca}/P_{Na}$ decreases with the increasing DBA content in polymer membranes, which implies that more hydrophobic polymer membranes may have better selectivity for different cations. For a better selectivity for different cations, two factors should be considered—the charge density and the membrane hydrophobicity.

TABLE 21

| Polymer ID | DBA (%) | $P(K^+)/P(Na^+)$ | $P(Ca^{2+})/P(Na^+)$ | $P(Mg^{2+})/P(Na^+)$ | $P(K^+)/P(Mg^{2+})$ |
|---|---|---|---|---|---|
| D3 | 48.5 | 1.29 | 0.27 | 0.25 | 5.16 |
| D4 | 56.1 | 1.43 | 0.26 | 0.24 | 5.96 |
| D5 | 64.4 | 1.34 | 0.13 | 0.08 | 16.75 |

Example 7

Synthesis of poly-2-fluoroacrylic Acid Beads

Beads are prepared by a direct suspension process where a mixture of 2-fluoroacrylic methyl ester/divinylbenzene/benzoyl peroxide in a weight ratio 90/9/1 are dispersed in water under high shear with polyvinylalcohol as a suspending agent. The suspension is stirred and heated at 80° C. for 10 hours. The residual monomer is eliminated by steam stripping. The beads are then filtered and treated with aqueous 3M NaOH to hydrolyze the polymer, then washed, treated with HCL, water-washed, and finally dried to form the desired polyα-fluoroacrylic acid particles. The average bead diameter is 250 microns as measured by Master Sizer (Malvern UK).

Example 8

Preparation of poly-2-fluoroacrylic Acid/Core-(DBA-DEAEMA)/Shell Particles

The core-shell particles are prepared by forming a coating of polymer D2 on the poly-2-fluoroacrylic acid beads prepared in example 5 using a Wurster coater. The shell polymer prepared in example 4 is first dissolved at 20 wt-% in toluene, and the thus obtained solution then dispersed in water in a 1:4 weight ratio with 2 wt-% based on the organic phase of CTAB (Hexadecyltrimethyl-Ammonium Bromide) as a surfactant, using a Ultra-Turrax high-shear homogenizer. The toluene is then driven off by evaporation under reduced pressure. The average diameter of the dispersion particles is 0.3 micrometer, as measured by Dynamic Light Scattering. The poly-2-fluoroacrylic acid beads are spray-coated with the shell polymer dispersion using a Wurster fluid bed coater 2"-4"/6" Portable Unit. The fluidized bed unit is operated so that an average 5 microns thick coating is deposited on the core particles.

Example 9

Preparation of Polystyrene Sulfonate/Core-Polyethyleneimine Shell Particles with $Na^+$ and $K^+$ Selective-Binding Properties Procedure for Coating PEI on Dowex Beads PEI (poly(ethyleneimine), Mw 10,000) and Dowex beads (H-form, X4-200) were purchased from commercial sources. PEI aqueous solutions with different concentrations were prepared by dissolving PEI directly into nanopure water.

Weighed dried Dowex beads were mixed with PEI aqueous solution in library format glass tubes. After a specified reaction time, the tubes were sealed and centrifuged at 1000 rpm for 15 minutes, the supernatant solutions were then decanted off. To the beads in each tube was added nanopure water to a total volume of 10 ml and all tubes were sealed and tumbled for 30 minutes. The same tumbling-centrifuging was repeated 3 times. The beads were freeze-dried and weighted until a constant weight was obtained.

The reaction solution composition and gel weight increase are displayed in Table 22.

TABLE 22

Conditions for coating PEI on Dowex beads

| Dowex Bead Weight (gm) | PEI Conc. (wt %) | PEI volume (ml) | Reaction time (hours) | Coated bead ID | Weight increase (Δwt %) |
|---|---|---|---|---|---|
| 0.1274 | 2.5 | 10 | 1 | DOWEX (2.5 wt-1 h) | * |
| 0.2223 | 2.5 | 10 | 6 | DOWEX (2.5 wt-6 h) | 3.1 |
| 0.1609 | 1.5 | 10 | 1 | DOWEX (2.5 wt-1 h) | * |
| 0.2407 | 1.5 | 10 | 6 | DOWEX (2.5 wt-6 h) | 0.9 |
| 0.2016 | 0.5 | 10 | 1 | DOWEX (2.5 wt-1 h) | * |
| 0.2347 | 0.5 | 10 | 6 | DOWEX (2.5 wt-6 h) | * |

* No weight increase was observed.

Method for Binding Study

A mixture of NaCl, KCl, $MgCl_2$, and $CaCl_2$ was dissolved in a MES buffer (pH6.0) (MES, 2-[N-morpholine]ethanesulfonic acid]. The concentration for each cation was determined by IC. The concentrations for $Na^+$, $K^+$, $Mg^{2+}$, and $Ca^{2+}$ are 26.4 mM, 9.75 mM, 4.75 mM and 4.16 mM respectively.

Figure 4:
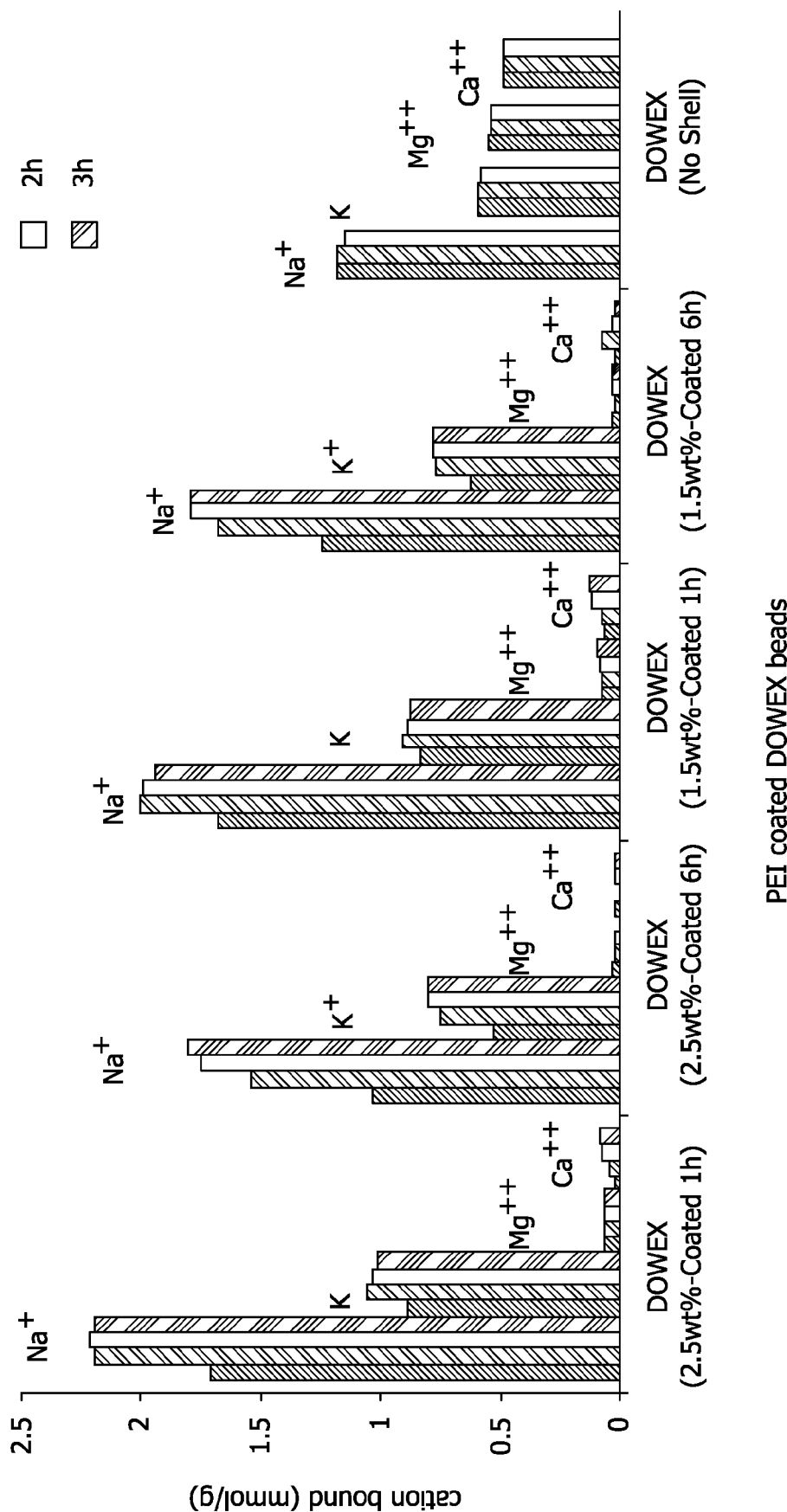
FIG. 4 depicts the binding data of different polyethyleneimine coated beads for different cations.

Weighed dried PEI-coated bead was put into a tube which contains 5-ml of MES buffer solution of NaCl, KCl, $MgCl_2$, and $CaCl_2$. The tube was sealed and tumbled. After a certain period of time as indicated in FIG. 4, the tube was centrifuged. 100 microliter of solution was then taken out from the supernatant for IC analysis. The binding amount of PEI coated beads for different cations were calculated from the concentration change in the solution.
The calculation is as follows:

$$\text{Ion bound in beads(mmol/g)} = [V \times (C_0 - C_t)/\{[\text{weight of beads}] \times 1000\}$$

$C_0$: initial concentration of metal ion (in mM)
$C_t$: concentration of metal ion after bead binding at a certain time (t hrs) (in mM)
V: solution volume (5 ml)
Weight of Beads (gm)

The binding data of different PEI coated beads for different cations are shown in FIG. 4. PEI coated Dowex beads show higher $Na^+$ and $K^+$ binding than the uncoated beads (bare beads). The coated beads show much more selective binding than bare beads. The thicker the PEI coating (e.g. Dowex (2.5 wt-6 h), coated from 2.5 wt % PEI solution for 6 hours), the more selective for the different cations. The binding kinetic study shows that the binding of cations equilibrates faster for the thinner coated beads and bare beads.

Example 10

Polystyrene Sulfonate Beads with EUDRAGIT Shell

Shell material: EUDRAGIT RL100 (Rohm), a copolymer of acrylic and methacrylic acid esters with 8.85-11.96% cationic ammonio methacrylate units, 10 wt % in ethanol and 10 wt % triacetin. Core: Lewatit (cross-linked polystyrene sulfonate in sodium form), size—300 μm.

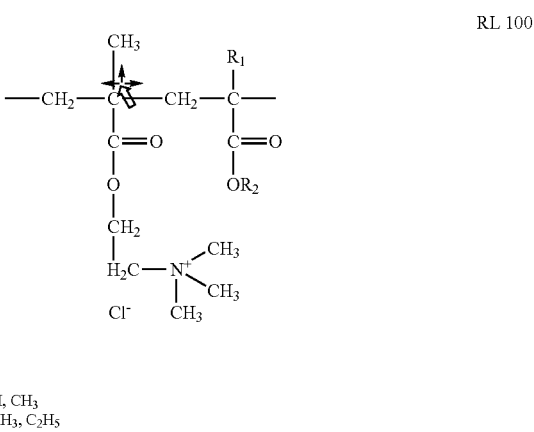

$R_1 = H, CH_3$
$R_2 = CH_3, C_2H_5$

The shell was applied using a FluidAir Wurster coater.

Binding was measured under following conditions:

Donor solution: 50 mM KCl and 50 mM $MgCl_2$

Bead concentration: 4 mg/ml

Duration: 6 hours

Figure 5:
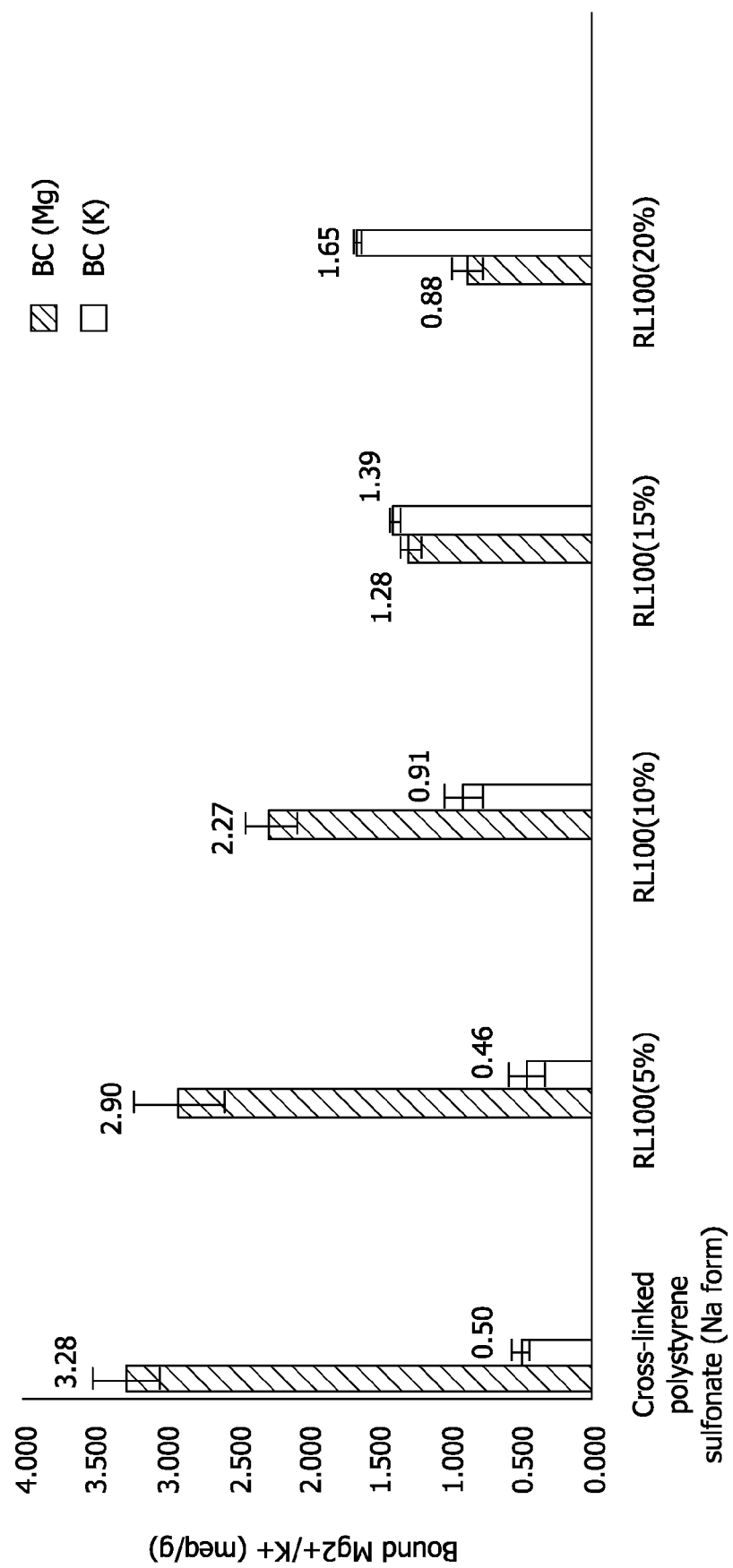
FIG. 5 depicts the effect of a Eudragit RL 100 shell on magnesium and potassium binding.

FIG. 5 shows the effect of the shell on $Mg^{2+}$ and $K^+$ binding. With increasing ratio of shell to core, $Mg^{2+}$ binding decreased and $K^+$ binding increased. 20 wt % shell coating gave a $K^+$ binding capacity of 1.65 meq/gm, which is about 3 times higher than for uncoated Dowex.

Example 11

Polystyrene Sulfonate Beads with Benzylated Polyethylene Imine Shell

Synthesis of Benzylated Polyethyleneimine (PEI)

To a 250 ml of round bottom flask were charged 15.6 g of PEI (363 mmol of —$NH_2$) and 125 ml of ethanol, this mixture was magnetically stirred until PEI was completely dissolved, then 30 g of $NaHCO_3$ (FW, 84; 256 mmol) and 40 ml of benzyl chloride (363 mmol) were subsequently added. The above mixture was reacted at 55° C. under nitrogen atmosphere overnight. Dichloromomethane was added to the slurry reaction mixture, followed by filtration to remove inorganic salt. The solvent in filtrate was removed by vacuum. Dichloromethane was used again to re-dissolve the reaction product; inorganic salt was further removed by filtration. The solvent in the filtrate was removed again under vacuum. Finally, the product was triturated in hexane, filtered and washed with hexane, and dried under vacuum. The benzylation degree was 84% as determined by $^1H$ NMR. Similar materials with various degree of benzylation (respectively 20% and 40% for Ben(20) and Ben(40)) were prepared by adjusting the benzyl chloride to PEI ratio.

Benzylated polyethylene imine (Ben-PEI) was coated onto Dowex beads.

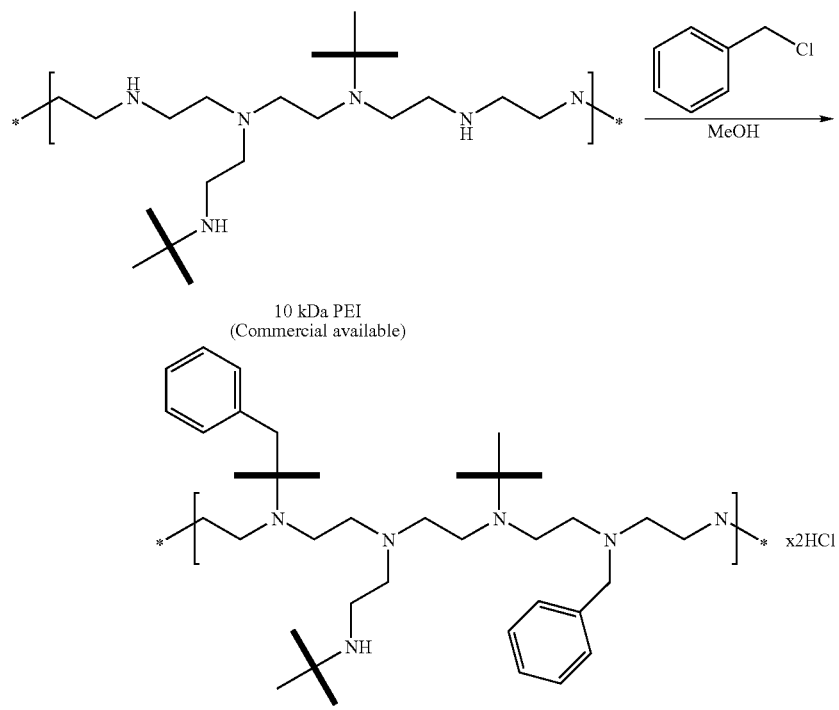

The shell was coated using solvent coacervation. The shell Ben(84)-PEI was dissolved in methanol and water mixture (3:1) at pH of 3. Shell and core were mixed for 5 minutes and methanol was removed by rotovap (40 minutes), isolated, washed, and dried.

Figure 6:
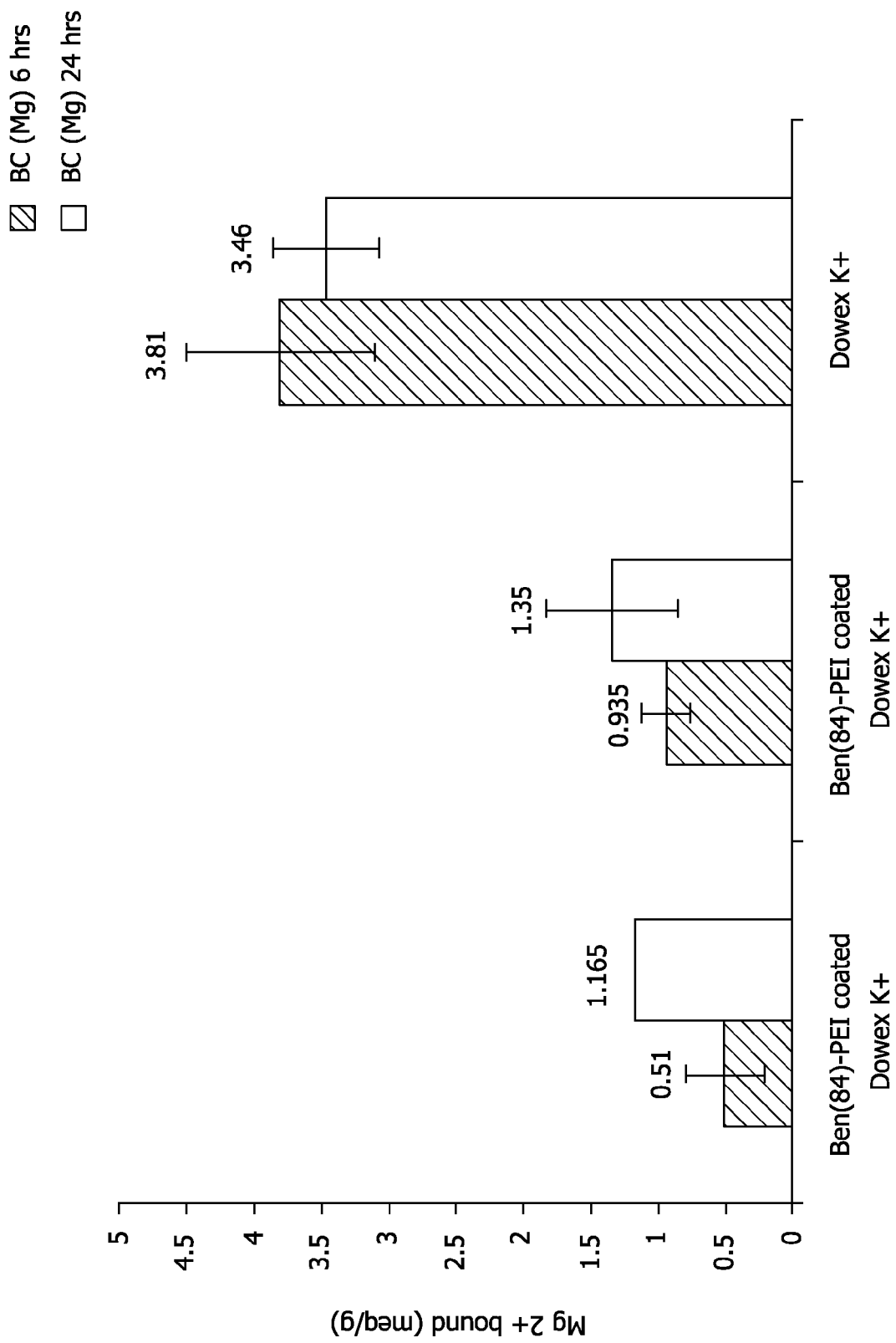
FIG. 6 depicts binding of magnesium on benzylated polyethyleneimine coated Dowex (K) beads.

Binding was measured under following conditions:
Donor solutions: 50 mM KCl and 50 mM $MgCl_2$
Bead concentration: 4 mg/ml
Duration: 6 and 24 hours Results of the binding measurements are shown in FIG. 6. Ben(84)-PEI showed selective binding for potassium after 6 and 24 hours as revealed by lower $Mg^{2+}$ binding compared to naked beads.

Figure 7:
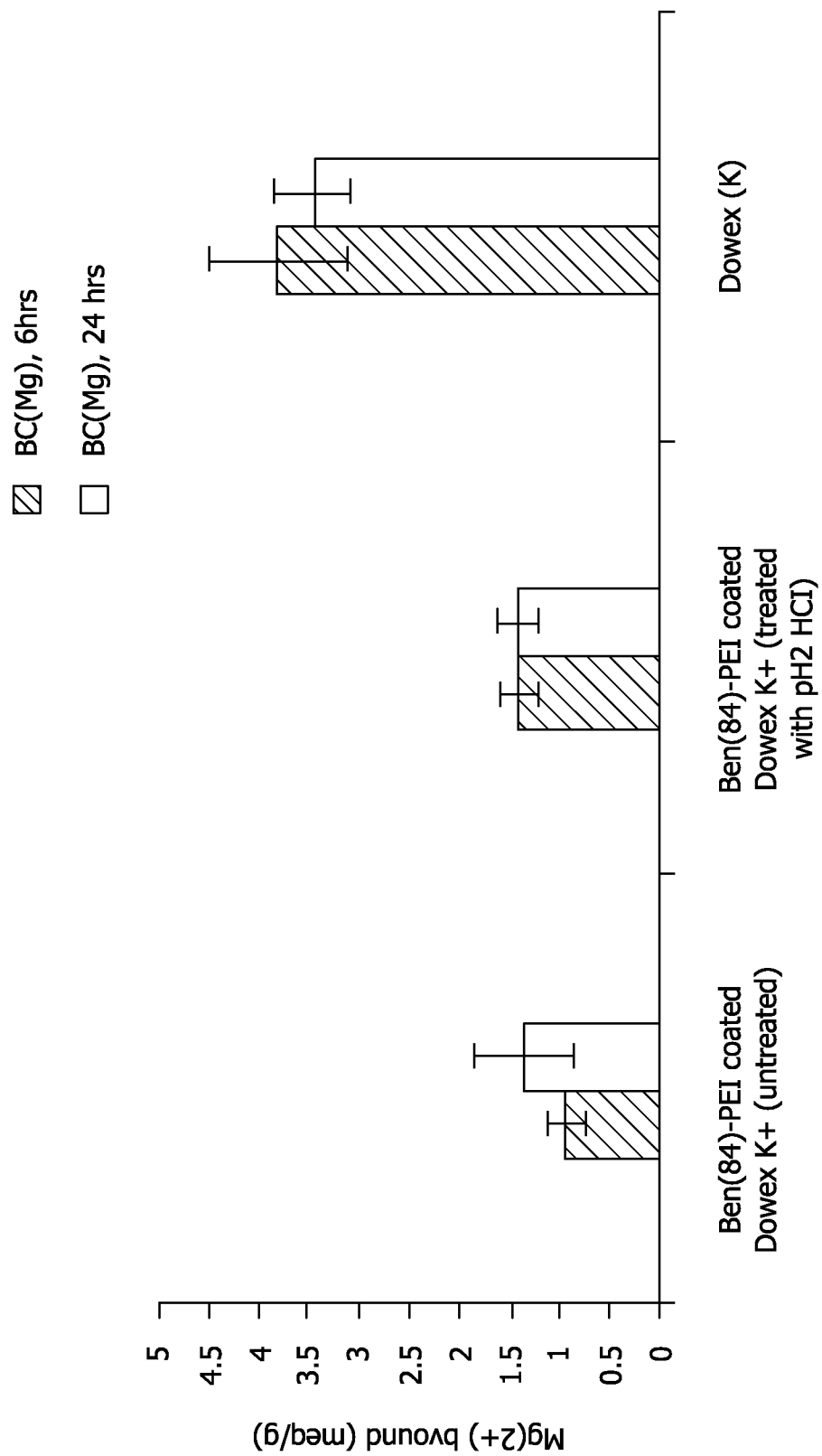
FIG. 7 depicts the stability of Ben(84)-PEI coated Dowex (K) beads under acid conditions representative of the acidic conditions in the stomach.

FIG. 7 depicts the stability of Ben(84)-PEI coated Dowex (K) beads under acid conditions representative of the acidic conditions in the stomach. The beads were exposed to pH 2HCl for 6 hours, isolated, and dried. Binding selectivity was tested for the post-treated beads. Binding conditions were as follows:
Donor solutions: 50 mM KCl and 50 mM $MgCl_2$
Bead concentration: 4 mg/ml
Duration: 6 and 24 hours The coating was stable and binding selectivity was maintained at 6 and 24 hours.

Example 12

FAA Beads with Benzylated Polyethylene Imine Shell

The shell was applied on the FAA core by the process of solvent coacervation. The shell, Ben(84)-PEI, was dissolved in methanol and water mixture (3:1) at pH of 4.5. The shell and core were mixed for 5 minutes and methanol was removed by rotovap (40 minutes), isolated, washed, and dried.

Figure 8:
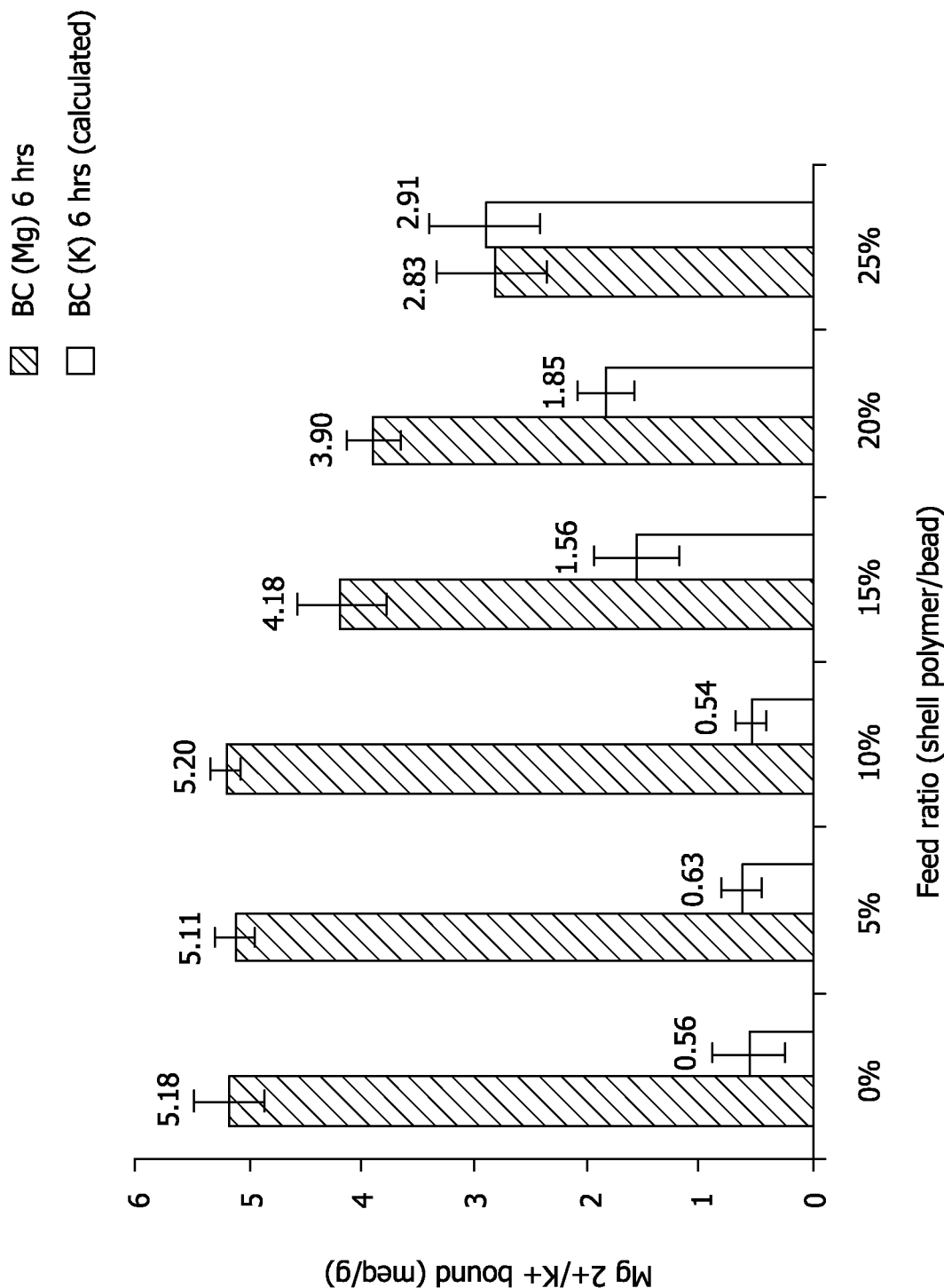
FIG. 8 depicts potassium and magnesium binding by Dowex beads coated with benzylated polyethyleneimine.

Binding was measured under following conditions:
Donor solutions: 50 mM KCl and 50 mM $MgCl_2$
Bead concentration: 4 mg/ml
Duration: 6 hours The potassium binding was calculated from actual magnesium uptake and overall binding capacity of polymer which was 5.74 meq/gm. The results are shown in FIG. 8. Increasing the ratio of shell/core caused a decrease in magnesium binding which indicates an increase in potassium binding.

Example 13

Coating by Controlled Precipitation Induced by pH Change

The shell comprised of Benzylated PEI, Ben (~20%); and Ben (~40%) on a Dowex(K) core. Binding was measured in 50 mM KCl and 50 mM $MgCl_2$.

Figure 9:
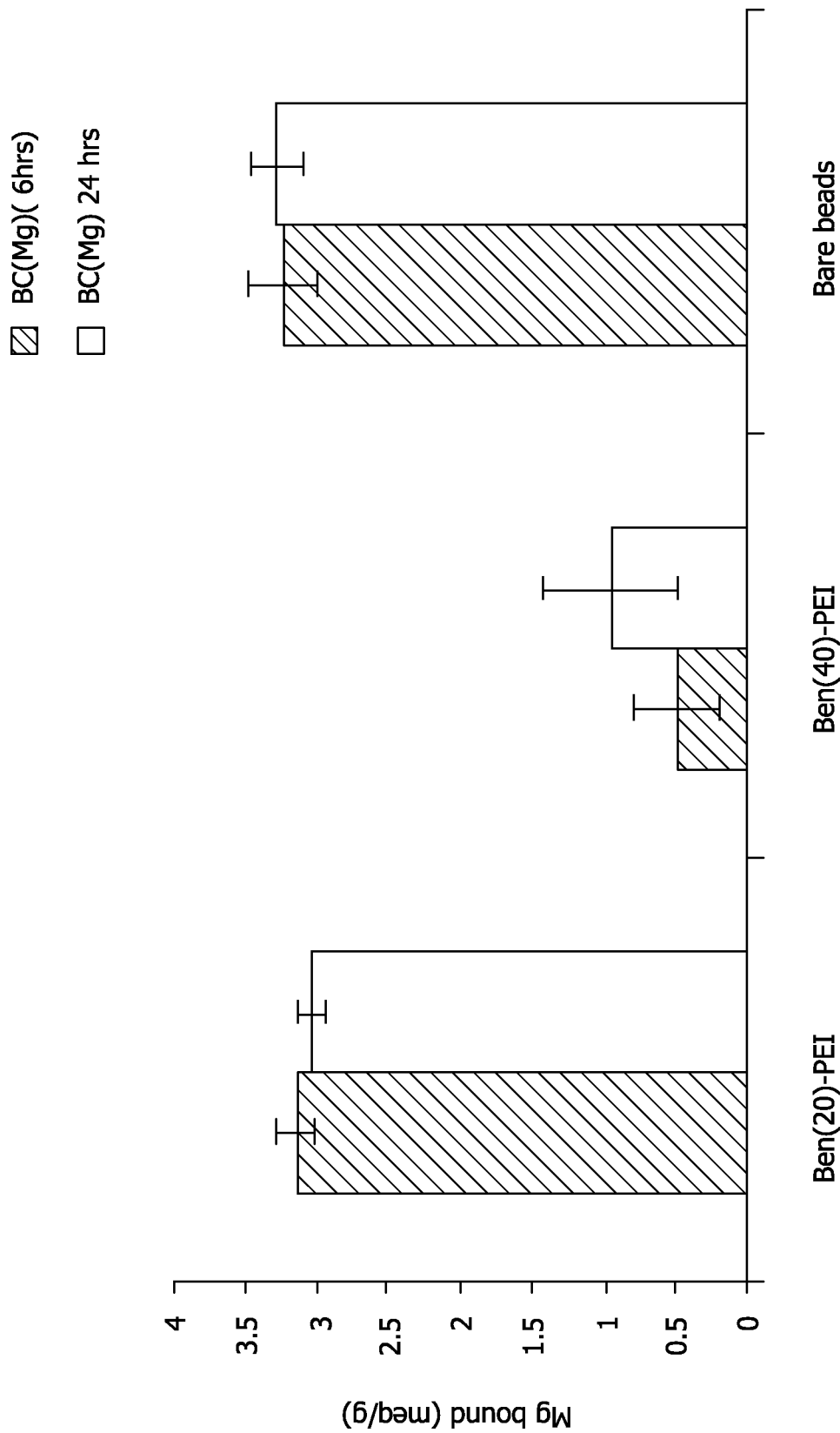
FIG. 9 depicts magnesium binding by fluoroacrylic acid beads with benzylated polyethylene imine shell.

FIG. 9 shows the results of the binding experiments. Controlled precipitation method for 40% benzylated PEI shows better coating and this combination of coating method and materials gives higher binding selectivity.

Example 14

Membrane Screening of Shell Polymers

Figure 10:
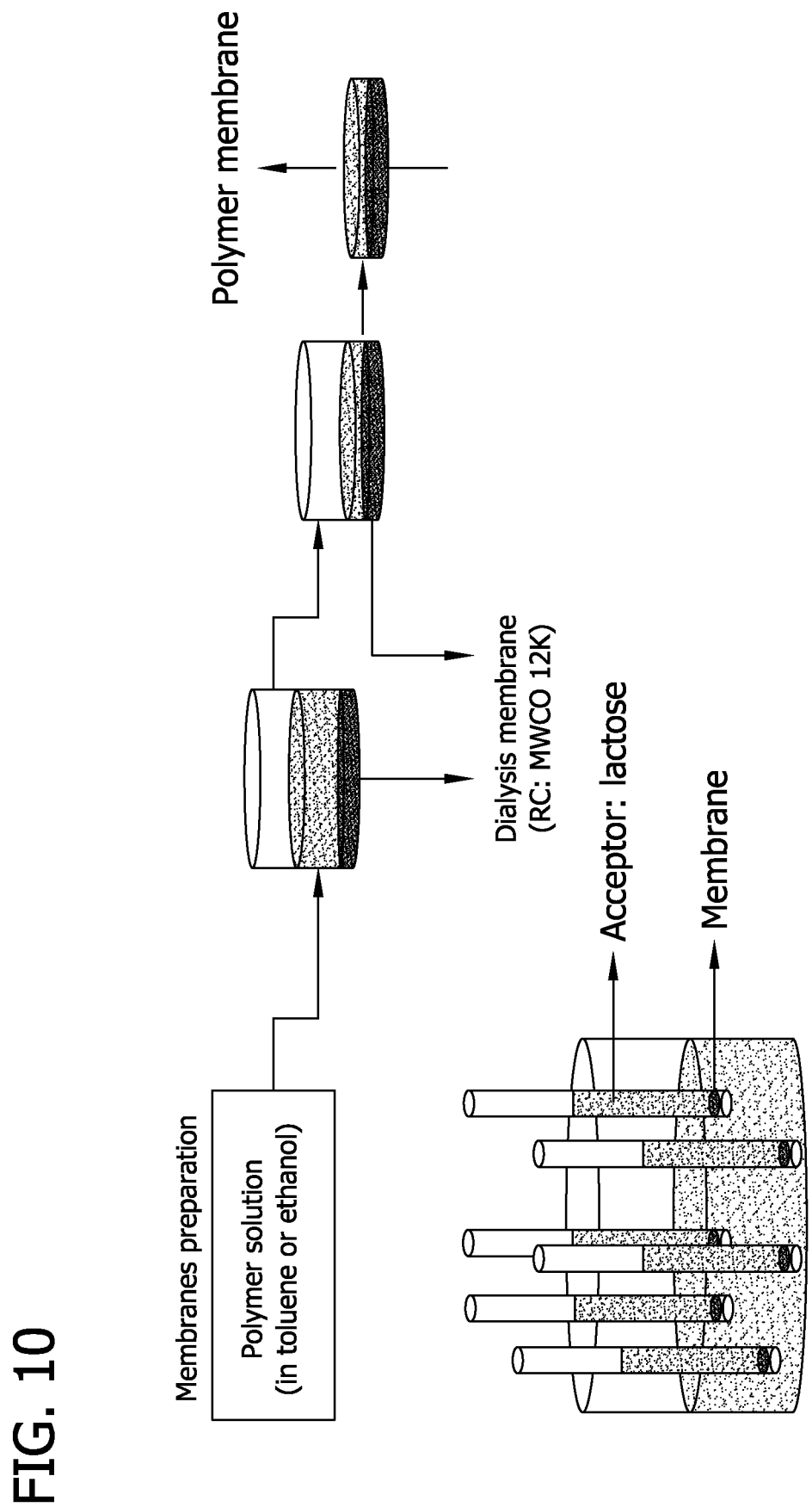
FIG. 10 depicts a setup for determining membrane permeability.

Shell polymers were screened by coating a flat membrane via solvent casting and using the coated membrane as the barrier in a diffusion cell, as depicted in FIG. 10. Donor solution was 50 mM 2-[N-morpholino]ethane sulfonic acid (MES) buffer at pH6.5 with 50 mM $K^+$ and $Mg^{2+}$. Permeability coefficient was calculated as described in Example 4 above. Cross-linked B-PEI was tested using this method.

Figure 11:
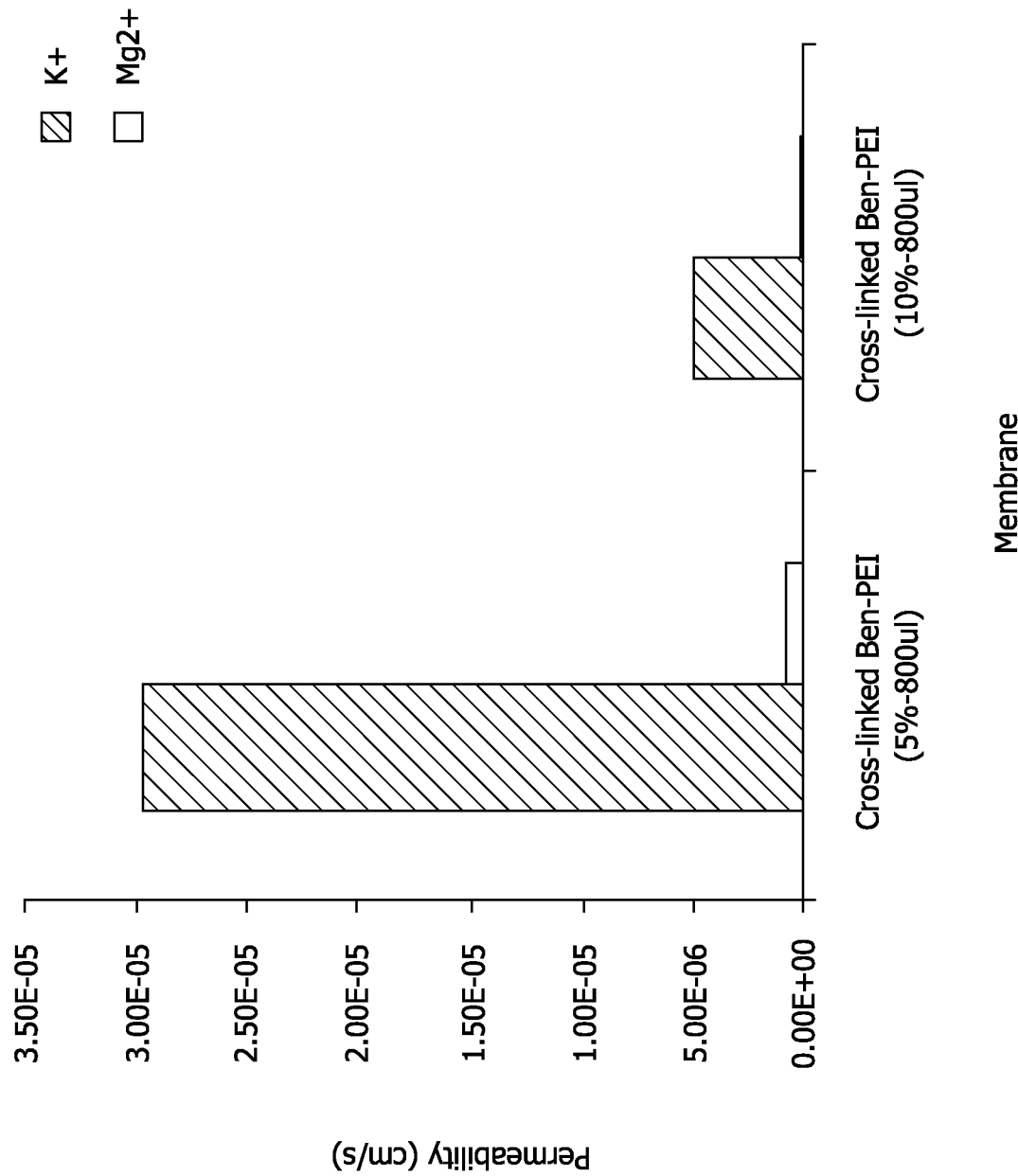
FIG. 11 depicts the permeability of benzylated polyethyleneimine membrane.

B-PEI (35 mol %) was cross-linked with 1,4-butanediol diacrylate. The cross-linker was reacted on the top of dried B-PEI for 4 hours. The screening was performed in 50 mM KCl and 50 mM $MgCl_2$ in 50 mM MES buffer. Cross-linker (diacrylate) reacted with B-PEI (35 mol %) membrane. As shown in FIG. 11, addition of the cross-linker reduced permeability coefficient and also showed good selectivity.

Figure 12:
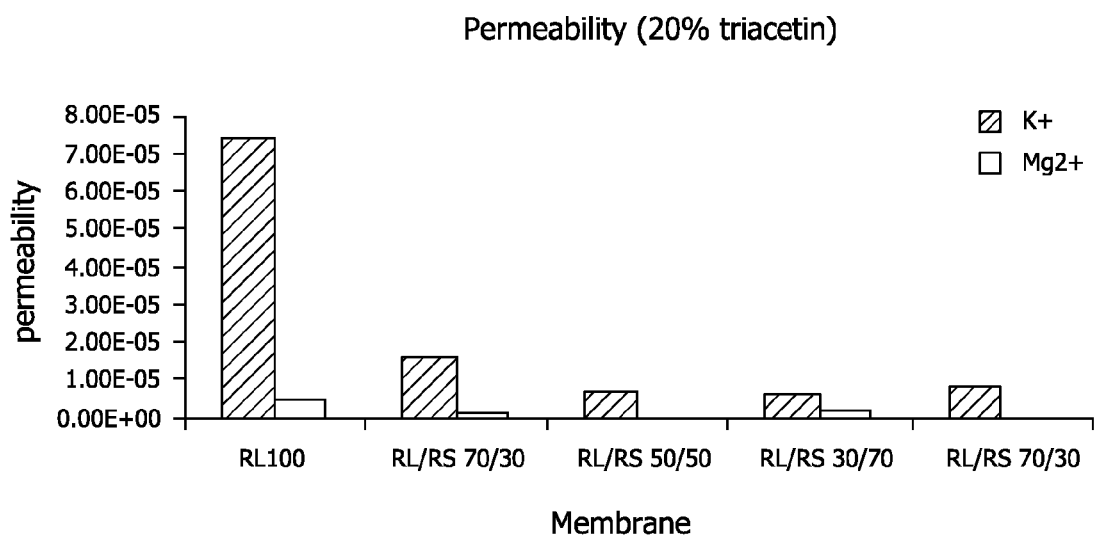
FIG. 12 depicts the permeability and permselectivity of membranes comprising of mixtures of Eudragit RL 100 and Eudragit RS 100.
Figure 12:
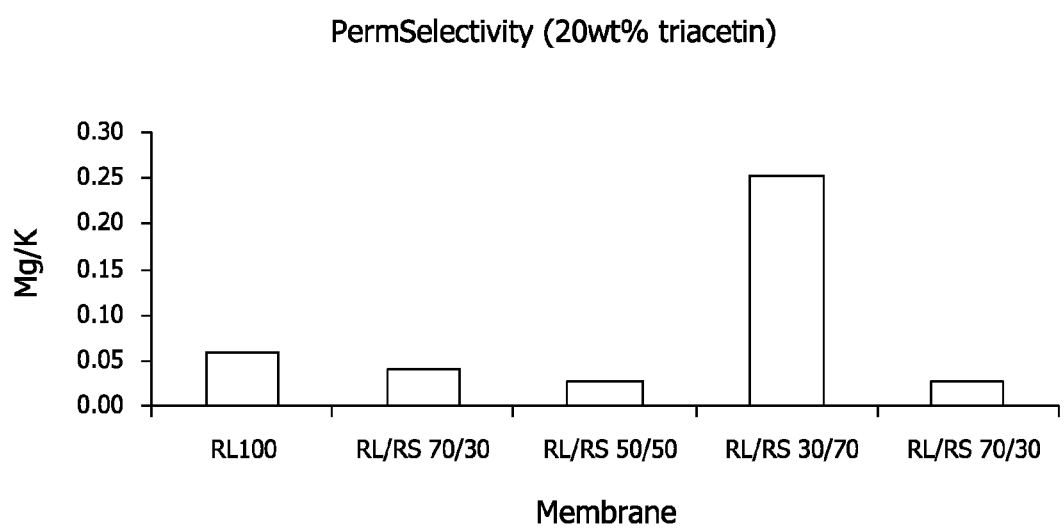

Blends of Eudragit RL 100 and RS 100 were also evaluated using the method of FIG. 10. The results are shown in FIG. 12. Adding RS 100 into RL 100 can reduce the permeability and the permselectivity stays in the same range. Membranes with more than 50 wt % of RS100 lost selectivity ([$K^+$] in the same scale, but [$Mg^{2+}$] much higher than other composites).

Example 15

Effects of Bile Acids on $K^+$ Binding

Figure 13:
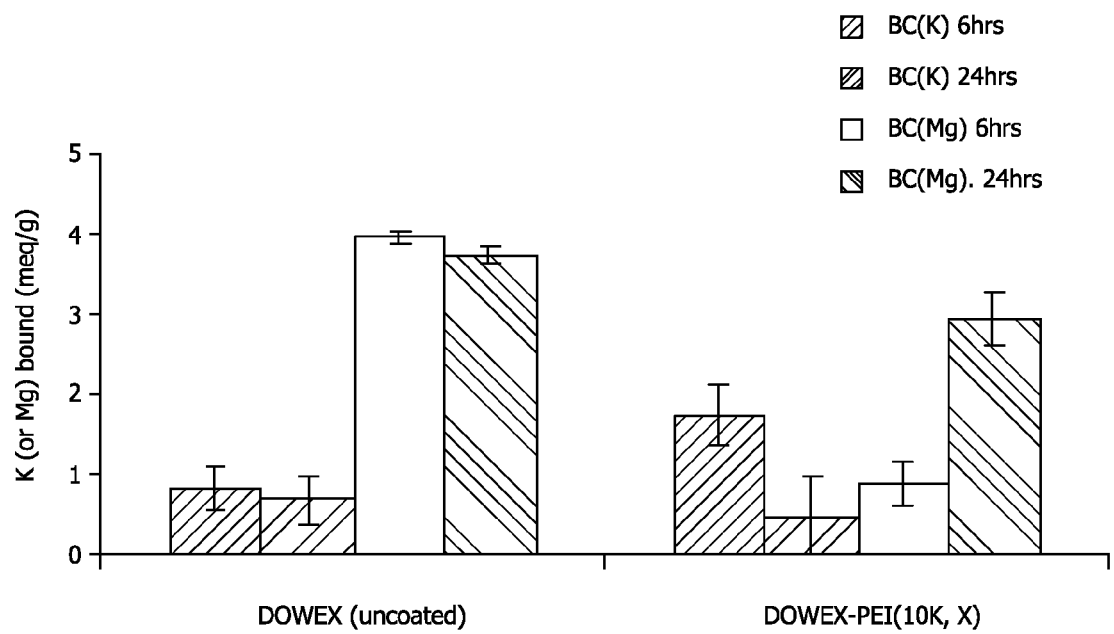
FIG. 13 depicts the effects of bile acids on potassium binding by Dowex(Li) coated with polyethyleneimine.
Figure 13:
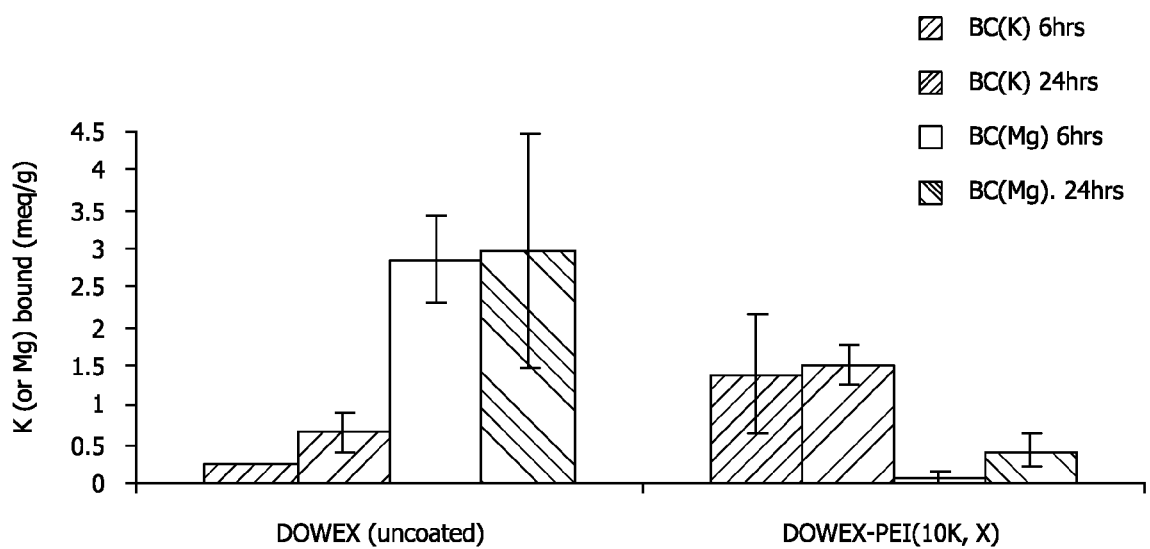

Dowex(Li) (~100 μm) was first coated with PEI aqueous solution. The supernatant was removed and the coat was further crosslinked with 1,2-Bis-(2-iodoethoxy)-ethane (BIEE). Binding was measured in 50 mM KCl and 50 mM of MgCl2, MES buffer, pH 6.5. Bile acids extract used was 2 mg/ml (bile extract porcine with 60% bile acids and 40% unknowns, i.e., free fatty acids, phospholipids, etc.). Time: 6 and 24 hrs and Bead content: 4 mg/ml. Results are shown in FIG. 13. Enhanced performance of the shell was observed in the presence of bile acids, fatty acids, and lipids.

All publications and patent applications mentioned in this specification are herein incorporated by reference to the same extent as if each individual publication or patent application was specifically and individually indicated to be incorporated by reference.

It will be apparent to one of ordinary skill in the art that many changes and modifications can be made thereto without departing from the spirit or scope of the appended claims.

The invention claimed is:

1. A method for removing potassium from an animal subject in need thereof comprising administering core-shell particles comprising a core component encapsulated in a shell component to the animal subject, said core component comprising a potassium binding polymer, said shell component comprising a crosslinked amine functional polymer alkylated with hydrophobic agent(s).

2. The method of claim 1 wherein said core-shell particles have a capacity for binding potassium ion in a gastrointestinal tract of said animal subject.

3. The method of claim 2 wherein said core-shell particles retain a significant amount of said bound potassium ion during a period of residence of the core-shell particles in the gastrointestinal tract of said animal subject.

4. The method of claim 1 wherein the core component comprises crosslinked carboxylate, phosphonate, sulfate, sulfonate, sulfamate polymers or combinations thereof.

5. The method of claim 1 wherein the alkylating agents have the formula RX where R is a $C_1$-$C_{20}$ alkyl, $C_1$-$C_{20}$ hydroxy-alkyl, $C_6$-$C_{20}$ aralkyl, $C_1$-$C_{20}$ alkylammonium, or $C_1$-$C_{20}$ alkylamido group and X comprises one or more electrophilic groups.

6. The method of claim 1 wherein the alkylating agent is an alkyl or alkylaryl group carrying an amine-reactive electrophile.

7. The method of claim 1 wherein the alkylating agent is selected from the group consisting of benzyl halide and dodecyl halide.

8. The method of claim 1 wherein the alkylating agent includes at least two electrophilic groups X.

9. The method of claim 8 wherein the alkylating agent is selected from the group consisting of di-haloalkane, dihalopolyethylene glycol, and epichlorohydrin.

10. The method of claim 1 wherein the shell thickness is from about 0.002 μm to about 50 μm.

11. The method of claim 1 wherein the shell to core weight ratio is 0.01% to 50%.

12. The method of claim 1 wherein the size of the core-shell particle is from about 200 nm to about 2 mm.

13. The method of claim 1 wherein the animal subject suffers from hyperkalemia, depressed renal synthesis of calcitriol, renal insufficiency, hypertension, chronic heart failure, end stage renal disease, fluid overload, or anabolic metabolism.

14. The method of claim 1 wherein the animal subject patient suffers from hyperkalemia.

15. A method of removing potassium from a patient in need thereof comprising administering core-shell particles to the patient, said core-shell particles comprising a core component encapsulated in a shell component, said core component comprising a crosslinked potassium binding polymer, said shell component comprising a crosslinked amine functional polymer alkylated with an alkyl or alkylaryl group.

16. The method of claim 15, the core component comprising crosslinked carboxylate, phosphonate, sulfate, sulfonate, sulfamate polymers or combinations thereof.

17. The method of claim 15 wherein the shell thickness is from about 0.002 μm to about 50 μm.

18. The method of claim 15 wherein the alkylating agent is a benzyl halide.

19. The method of claim 15 wherein the size of the core-shell particle is from about 200 nm to about 2 mm.

20. The method of claim 19 wherein the alkylating agent is a benzyl halide.

21. The method of claim 15 wherein the patient suffers from hyperkalemia, depressed renal synthesis of calcitriol, renal insufficiency, hypertension, chronic heart failure, end stage renal disease, fluid overload, or anabolic metabolism.

22. The method of claim 15 wherein the patient suffers from hyperkalemia.

\* \* \* \* \*